(12) United States Patent
Watanabe et al.

(10) Patent No.: US 8,039,128 B2
(45) Date of Patent: Oct. 18, 2011

(54) FLUORENE COMPOUND, ORGANIC LIGHT EMITTING DEVICE AND DISPLAY DEVICE USING THE FLUORENE COMPOUND

(75) Inventors: Taiki Watanabe, Akishima (JP); Kazunori Ueno, Glen Waverly (AU); Koichi Suzuki, Yokohama (JP); Yohei Iwasaki, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 217 days.

(21) Appl. No.: 12/516,867

(22) PCT Filed: May 21, 2008

(86) PCT No.: PCT/JP2008/059762
§ 371 (c)(1),
(2), (4) Date: May 29, 2009

(87) PCT Pub. No.: WO2008/146825
PCT Pub. Date: Dec. 4, 2008

(65) Prior Publication Data
US 2010/0072885 A1    Mar. 25, 2010

(30) Foreign Application Priority Data
May 28, 2007   (JP) .................................. 2007-140160

(51) Int. Cl.
*H01L 51/54* (2006.01)
(52) U.S. Cl. ........ 428/690; 313/504; 313/505; 313/506; 428/917; 570/129
(58) Field of Classification Search .................. 428/690, 428/917; 313/504, 505, 506; 570/129
See application file for complete search history.

(56) References Cited

U.S. PATENT DOCUMENTS
5,708,130 A   1/1998   Woo et al. ..................... 528/397
(Continued)

FOREIGN PATENT DOCUMENTS
JP    11-273863    10/1999
(Continued)

OTHER PUBLICATIONS
International Preliminary Report on Patentability issued on PCT/JP2008/059762 on Dec. 10, 2009, 7 pages.
(Continued)

*Primary Examiner* — D. Lawrence Tarazano
*Assistant Examiner* — Gregory Clark
(74) *Attorney, Agent, or Firm* — Fitzpatrick, Cella, Harper & Scinto

(57) ABSTRACT

An organic light emitting device having a high efficiency and durability is provided. The organic light emitting device includes an anode, a cathode and a layer formed of an organic compound interposed between the anode and the cathode, and contains at least one kind of the fluorene compound represented by the following general formula (I) or (II):

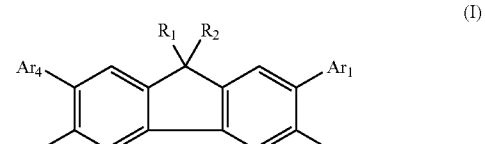

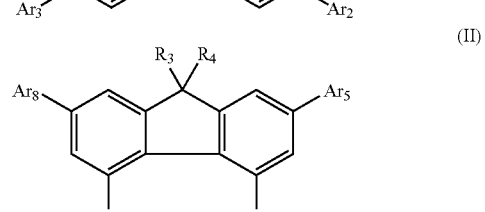

wherein $R_1$ to $R_4$ each represent an alkyl group, a fluorinated alkyl group, a substituted or unsubstituted aralkyl group, or a substituted or unsubstituted aryl group; and $Ar_1$ to $Ar_8$ represent a substituted or unsubstituted aryl group or a substituted or unsubstituted polycondensed aromatic group.

5 Claims, 3 Drawing Sheets

U.S. PATENT DOCUMENTS

| | | | |
|---|---|---|---|
| 6,097,147 A | 8/2000 | Baldo et al. | 313/506 |
| 6,303,231 B1 | 10/2001 | Sawada et al. | 428/470 |
| 6,683,017 B2 | 1/2004 | Gao et al. | 502/126 |
| 6,733,905 B2 | 5/2004 | Takiguchi et al. | 428/690 |
| 6,797,980 B2 | 9/2004 | Takiguchi et al. | 257/40 |
| 6,991,857 B2 | 1/2006 | Tsuboyama et al. | 428/690 |
| 7,229,702 B2 | 6/2007 | Saitoh et al. | 428/690 |
| 7,241,513 B2 | 7/2007 | Suzuki et al. | 428/690 |
| 2001/0040296 A1 | 11/2001 | Hiromatsu | 257/774 |
| 2002/0064966 A1* | 5/2002 | Seki et al. | 438/780 |
| 2003/0039838 A1* | 2/2003 | Chen et al. | 428/411.1 |
| 2005/0236977 A1 | 10/2005 | Yamada et al. | 313/504 |
| 2006/0121312 A1 | 6/2006 | Yamada et al. | 428/690 |
| 2007/0111029 A1 | 5/2007 | Yamada et al. | 428/690 |
| 2007/0257603 A1 | 11/2007 | Suzuki et al. | 313/504 |
| 2008/0220289 A1 | 9/2008 | Shioya et al. | 428/691 |

FOREIGN PATENT DOCUMENTS

| | | | |
|---|---|---|---|
| JP | 2000-033561 | | 2/2000 |
| JP | 2001-033684 | | 2/2001 |
| JP | 2001-219909 | | 8/2001 |
| JP | 2001-239281 | | 9/2001 |
| JP | 2001-247859 | | 9/2001 |
| JP | 2001-248165 | | 9/2001 |
| JP | 2001-298470 | | 10/2001 |
| JP | 2002-173674 | | 6/2002 |
| JP | 2002-203678 | | 7/2002 |
| JP | 2002-203679 | | 7/2002 |
| JP | 2003-055275 | | 2/2003 |
| JP | 2003-277305 | | 10/2003 |
| JP | 2004-083481 | * | 3/2004 |
| JP | 2004-277368 | | 10/2004 |
| JP | 2007-291058 | | 11/2007 |
| WO | WO 00/57676 | | 9/2000 |
| WO | WO 00/70655 | | 11/2000 |
| WO | WO 01/08230 A1 | | 2/2001 |
| WO | WO 01/39234 A2 | | 5/2001 |
| WO | WO 01/41512 A1 | | 6/2001 |
| WO | WO 02/02714 A2 | | 1/2002 |
| WO | WO 02/15645 A1 | | 2/2002 |

OTHER PUBLICATIONS

Miyaura, Norio et al., "Palladium-Catlyzed Cross-Coupling Reactions of Organoboron Compounds," Chemical Review, pp. 2457-2483, vol. 95, No. 7, 1995.

Yamamoto, Takakazu et al., "A Novel Type of Polycondensation Utilizing Transition Metal-Catalyzed C-C Coupling—I. Preparation of Thermostable Polyphenylene Type Polymers," Bulletin of the Chemical Society of Japan, pp. 2091-2097, vol. 51, No. 7, 1978.

Burrows, Hugh D., "Characterization of the Triplet State of Tris(8-hydroxyquinoline;aluminium(III) in Benzene Solution," Journal of the American Society, pp. 15310-15311, vol. 125, 2003.

Yamamoto, Akio et al., "Organic metal, base and application," pp. 150 and 232, 1982 (English translation included).

Yersin, H., "Photochemistry and Photophysics of Coordination Compound," pp. 71-77 and 135-146, 1987 (English Translation included).

Akiyama, Shinji, "Recent Result and Future Challenges of Blue Phosphorescent Materials," Mitsubishi Chemical Group, Science and Technology Research Center, Inc. pp. 25 to 31.

Baldo, M.A., et al., "Highly Efficient Phosphorescent Emission From Organic Electroluminescent Device," Letter to Nature, vol. 395, pp. 151-154, Sep. 1998.

Baldo, M.A., et al., "Very High-Efficiency Green Organic Light-Emitting Devices Based on Electrophosphorescence," Applied Physics Letters, vol. 75, No. 1, pp. 4-6, Jul. 5, 1999.

Djurovich, Peter I. et al., "Ir(II) Cyclometalated Complexes As Efficient Phosphorescent Emitters in Polymer Blend and Organic LEDs," Polymer Preprints, vol. 41, No. 1, pp. 770-771, 2000.

Lamansky, Sergey et al., "Highly Phosphorescent Bis-Cyclometalated Iridium Complexes: Synthesis, Photophysical Characterization, and Use in Organic Light Emitting Diodes," Journal of The American Society, vol. 123, pp. 4304-4312, 2001.

Adachi, Chihaya et al., : "Endothermic Energy Transfer: A Mechanism for Generating Very Efficient High-Energy Phosphorescent Emission in Organic Materials," Applied Physics Letters, vol. 79, No. 13, pp. 2082-2084.

* cited by examiner

FLUORENE COMPOUND, ORGANIC LIGHT EMITTING DEVICE AND DISPLAY DEVICE USING THE FLUORENE COMPOUND

TECHNICAL FIELD

The present invention relates to a novel fluorene compound, an organic light emitting device and a display device using the fluorene compound.

BACKGROUND ART

An organic light emitting device is a device in which a thin film including a fluorescent organic compound or a phosphorescent organic compound is interposed between an anode and a cathode. Further, electrons and holes are injected from the respective electrodes to generate exciton, whereby the organic light emitting device emits light when the exciton return to a ground state.

Recently, an organic light emitting device using a fluorene compound as a light emitting material has been extensively studied. For example, a fluorene compound disclosed in Japanese Patent Application Laid-Open No. H11-273863 and a trimer of 9,9-dimethyl-fluorene disclosed in Japanese Patent Application Laid-Open No. 2003-55275 are included. Further, according to Japanese Patent Application Laid-Open No. H11-273863 and Japanese Patent Application Laid-Open No. 2003-55275, it is described that a light emitting device using a fluorene compound has a high efficiency, and the utility of a compound containing a fluorene skeleton in a molecule is being recognized. However, there are no fluorene compounds that satisfy both a high efficiency and high durability for practical use, so there is a demand for a light emitting material based on a fluorene skeleton that leads to further higher luminance and longer life of a device.

DISCLOSURE OF THE INVENTION

An object of the present invention is to provide a novel fluorene compound. Another object of the present invention is to provide an organic light emitting device having a high efficiency and high durability. Still another object of the present invention is to provide an organic light emitting device that can be produced easily and can be produced even by relatively inexpensive coating.

The inventors of the present invention have earnestly studied so as to solve the above problem, thereby achieving the present invention. That is, a fluorene compound of the present invention is represented by the following general formula (I) or (II).

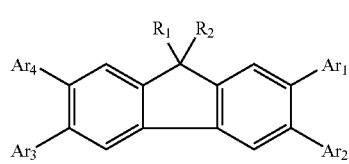
(I)

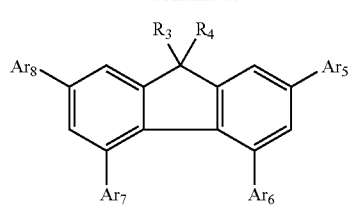
(II)

In the formulae (I) and (II), $R_1$ to $R_4$ each represent an alkyl group, a fluorinated alkyl group, a substituted or unsubstituted aralkyl group, or a substituted or unsubstituted aryl group. $Ar_1$ to $Ar_8$ represent a substituted or unsubstituted aryl group or a substituted or unsubstituted polycondensed aromatic group.

Further, a fluorene compound of the present invention is represented by the following general formula (III) or (IV).

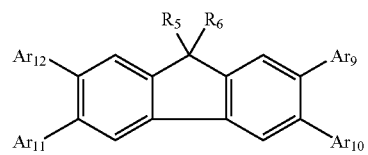
(III)

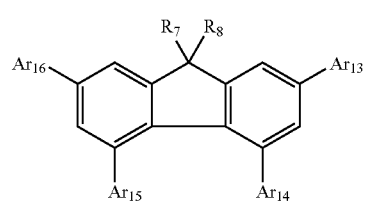
(IV)

In the formula (III) or (IV), among $Ar_9$ to $Ar_{16}$, at least one represents a substituent represented by the following general formula (V).

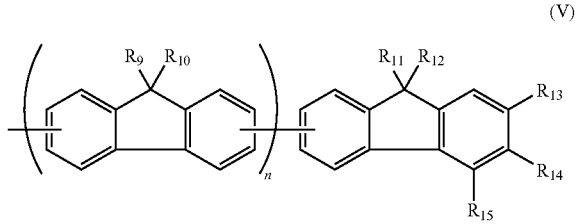
(V)

In the formula (V), $R_9$ to $R_{12}$ each represent an alkyl group, a fluorinated alkyl group, a substituted or unsubstituted aralkyl group, or a substituted or unsubstituted aryl group. $R_{13}$ to $R_{15}$ each represent a hydrogen atom, an alkyl group, a substituted or unsubstituted aralkyl group, a substituted or unsubstituted aryl group, a substituted or unsubstituted polycondensed aromatic group, or an amino group. N represents an integer of 0 to 10.

$R_5$ to $R_8$ each represent an alkyl group, a fluorinated alkyl group, a substituted or unsubstituted aralkyl group, and a substituted or unsubstituted aryl group. Among $Ar_9$ to $Ar_{16}$, those which are not a substituent represented by the general formula (V) each represent a substituted or unsubstituted aryl group, or a substituted or unsubstituted polycondensed aromatic group.

According to the present invention, a novel fluorene compound can be provided. Further, according to the present invention, an organic light emitting device having a high efficiency and high durability can be provided. Further, according to the present invention, an organic light emitting device that can be produced easily and can be produced even by relatively inexpensive coating.

BRIEF DESCRIPTION OF THE DRAWINGS

FIG. 1A is a cross-sectional view illustrating a first embodiment, FIG. 1B is a cross-sectional view illustrating a second embodiment, and FIG. 1C is a cross-sectional view illustrating a third embodiment.

BEST MODE FOR CARRYING OUT THE INVENTION

Figure 1A:
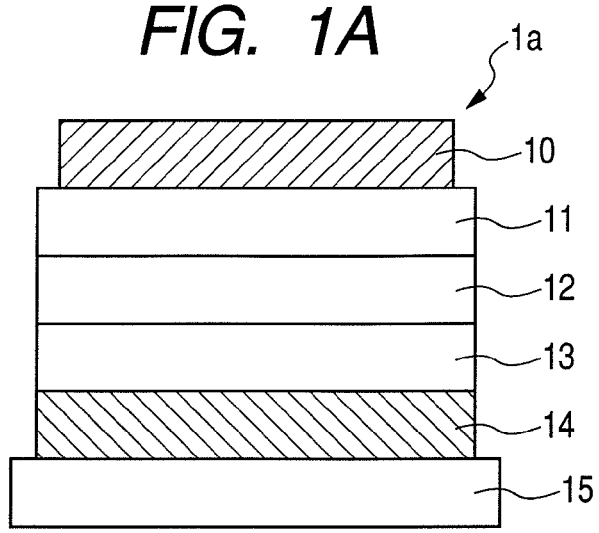
FIGS. 1A, 1B, and 1C are cross-sectional views illustrating examples of embodiments of an organic light emitting device of the present invention.

Hereinafter, the present invention will be described in detail.

First, a fluorene compound of the present invention will be described.

As a first embodiment of the fluorene compound of the present invention, there are fluorene compounds represented by the following general formulae (I) and (II).

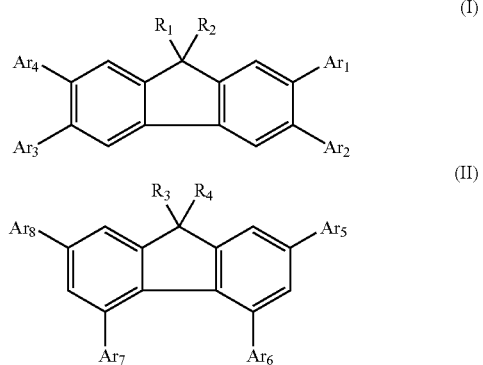

In the formulae (I) and (II), $R_1$ to $R_4$ each represent an alkyl group, a fluorinated alkyl group, a substituted or unsubstituted aralkyl group, or a substituted or unsubstituted aryl group.

Examples of the alkyl group represented by $R_1$ to $R_4$ include a methyl group, an ethyl group, a propyl group, an isopropyl group, a butyl group, an isobutyl group, a secondary butyl group, a tertiary butyl group, a pentyl group, a hexyl group, a cyclopropyl group, a cyclopentyl group, and a cyclohexyl group.

Examples of the fluorinated alkyl group represented by $R_1$ to $R_4$ include a trifluoromethyl group and a pentafluoroethyl group.

Examples of the aralkyl group represented by $R_1$ to $R_4$ include a benzyl group, a phenethyl group, a naphthyl methyl group, and a naphthyl ethyl group.

Examples of the aryl group represented by $R_1$ to $R_4$ include a phenyl group, a biphenyl group, and a terphenyl group.

Examples of the substituents that the aralkyl group and aryl group may have include: alkyl groups such as a methyl group, an ethyl group, and an n-propyl group; fluorinated alkyl groups such as a trifluoromethyl group and a pentafluoroethyl group; aralkyl groups such as a benzyl group and a phenethyl group; aryl groups such as a phenyl group, a biphenyl group, and a terphenyl group; heterocyclic groups such as a thienyl group, a pyrrolyl group, a pyridyl group, a bipyridyl group, an oxazolyl group, an oxadiazolyl group, a thiazolyl group, and a thiadiazolyl group; polycondensed aromatic groups such as a naphthyl group and a phenanthryl group; polycondensed heterocyclic groups such as a quinolyl group, a carbazolyl group, an acridinyl group, and a phenanthrolyl group; aryloxy groups such as a phenoxyl group and a naphthoxyl group; substituted amino groups such as a dimethylamino group, a diethylamino group, a diphenylamino group, a ditolylamino group, a dianisolylamino group, a 9,9-dimethyl-9H-fluorenyl phenylamino group, a difluorenyl group, a naphthylphenylamino group, and a dinaphthylamino group; substituted boryl groups such as a diphenylboryl group and a dimesitylboryl group; substituted silyl groups such as a trimethylsilyl group and a triphenylsilyl group; substituted germyl groups such as trimethyl germyl group and a triphenyl germyl group; halogen atoms such as fluorine, chlorine, bromine, and iodine and deuterium.

In the formulae (I) and (II), $Ar_1$ to $Ar_8$ each represent a substituted or unsubstituted aryl group or a substituted or unsubstituted polycondensed aromatic group.

Examples of the aryl group represented by $Ar_1$ to $Ar_8$ include a phenyl group, a biphenyl group, and a terphenyl group.

Examples of the polycondensed aromatic group include a naphthyl group, a phenanthryl group, a tolyl group, a xylyl group, a methylnaphthyl group, an anthryl group, a fluoranthenyl group, a pyrenyl group, and a benzofluorenyl group.

Examples of the substituents that the above aryl group and polycondensed aromatic group may have include: alkyl groups such as a methyl group, an ethyl group, an n-propyl group, and a tert-butyl group; fluorinated alkyl groups such as a trifluoromethyl group and a pentafluoroethyl group; aralkyl groups such as a benzyl group and a phenethyl group; aryl groups such as a phenyl group, a biphenyl group, and a terphenyl group; heterocyclic groups such as a thienyl group, a pyrrolyl group, a pyridyl group, a bipyridyl group, an oxazolyl group, an oxadiazolyl group, a thiazolyl group, and a thiadiazolyl group; polycondensed aromatic groups such as a naphthyl group and a phenanthryl group; polycondensed heterocyclic groups such as a quinolyl group, a carbazolyl group, an acridinyl group, and a phenanthrolyl group; aryloxy groups such as a phenoxyl group and a naphthoxyl group; substituted amino groups such as a dimethylamino group, a diethylamino group, a diphenylamino group, a ditolylamino group, a dianisolylamino group, a 9,9-dimethyl-9H-fluorenylphenylamino group, a difluorenyl group, a naphthylphenylamino group, and a dinaphthylamino group; substituted boryl groups such as a diphenylboryl group and a dimesitylboryl group; substituted silyl groups such as a trimethylsilyl group and a triphenylsilyl group; substituted germyl groups such as a trimethyl germyl group and a triphenyl germyl group; halogen atoms such as fluorine, chlorine, bromine, and iodine and deuterium.

As a second embodiment of the fluorene compound of the present invention, the following general formula (III) or (IV) represents a branched oligofluorene compound.

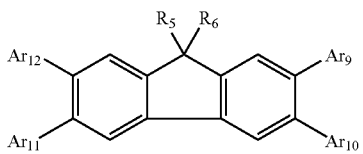

(III)

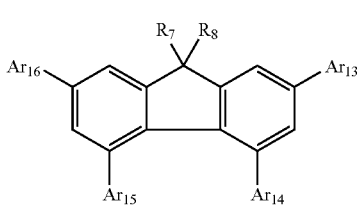

(IV)

In the formulae (III) and (IV), among $Ar_9$ to $Ar_{16}$, at least one represents a substituent represented by the following general formula (V).

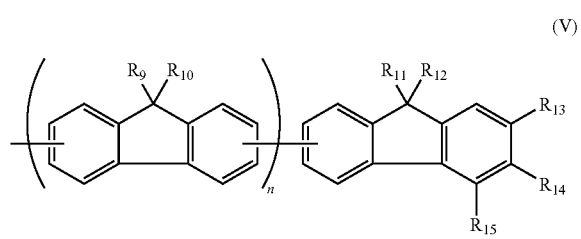

(V)

In the formula (V), $R_9$ to $R_{12}$ each represent an alkyl group, a fluorinated alkyl group, a substituted or unsubstituted aralkyl group, or a substituted or unsubstituted aryl group.

Specific examples of the alkyl group, fluorinated alkyl group, aralkyl group, and aryl group that are represented by $R_9$ to $R_{12}$, and substituents that the aralkyl group and aryl group may have are the same those as in the case of $R_1$ to $R_4$ in the formulae (I) and (II).

In the formula (V), $R_{13}$ to $R_{15}$ each represent a hydrogen atom, an alkyl group, a substituted or unsubstituted aralkyl group, a substituted or unsubstituted aryl group, a substituted or unsubstituted polycondensed aromatic group, or an amino group.

Specific examples of the alkyl group, fluorinated alkyl group, aralkyl group, and aryl group that are represented by $R_{13}$ to $R_{15}$, and substituents that the aralkyl group and aryl group may have are the same those as in the case of $R_1$ to $R_4$ in the formulae (I) and (II).

Examples of the polycondensed aromatic group represented by $R_{13}$ to $R_{15}$ include a naphthyl group, a phenanthryl group, a tolyl group, a xylyl group, a methylnaphthyl group, an anthryl group, and the substituent represented below.

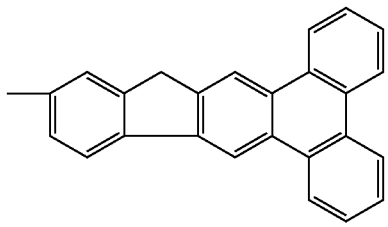

Examples of the amino group represented by $R_{13}$ to $R_{15}$ include a diphenylamino group, a ditolylamino group, a di-(4-t-butylphenyl)amino group, a di-(2-fluorenyl)amino group, a di-(3-fluorenyl)amino group, a di-(4-fluorenyl)amino group, a di-(biphenyl)amino group, a di-(β-naphthyl)amino group, and a di-(α-naphthyl)amino group.

Examples of the substituents that the polycondensed aromatic group may have include: alkyl groups such as a methyl group, an ethyl group, and an n-propyl group; fluorinated alkyl groups such as a trifluoromethyl group and a pentafluoroethyl group; aralkyl groups such as a benzyl group and a phenethyl group; aryl groups such as a phenyl group, a biphenyl group, and a terphenyl group; heterocyclic groups such as a thienyl group, a pyrrolyl group, a pyridyl group, a bipyridyl group, an oxazolyl group, an oxadiazolyl group, a thiazolyl group, and a thiadiazolyl group; polycondensed aromatic groups such as a naphthyl group and a phenanthryl group; polycondensed heterocyclic groups such as a quinolyl group, a carbazolyl group, an acridinyl group, and a phenanthrolyl group; aryloxy groups such as a phenoxyl group and a naphthoxyl group; substituted amino groups such as a dimethylamino group, a diethylamino group, a diphenylamino group, a ditolylamino group, a dianisolylamino group, a 9,9-dimethyl-9H-fluorenylphenylamino group, a difluorenyl group, a naphthylphenylamino group, and a dinaphthylamino group; substituted boryl groups such as a diphenylboryl group and a dimesitylboryl group; substituted silyl groups such as a trimethylsilyl group and a triphenylsilyl group; substituted germyl groups such as a trimethyl germyl group and a triphenyl germyl group; halogen atoms such as fluorine, chlorine, bromine, and iodine and deuterium.

In the formula (V), n represents an integer of 0 to 10.

In the formulae (III) and (IV), $R_5$ to $R_8$ each represent an alkyl group, a fluorinated alkyl group, a substituted or unsubstituted aralkyl group, or a substituted or unsubstituted aryl group.

Specific examples of an alkyl group, a fluorinated alkyl group, an aralkyl group, and an aryl group, and a substituent which an aralkyl group and an aryl group may have, represented by $R_5$ to $R_8$, are similar to $R_1$ to $R_4$ in the formulae (I) and (II).

In the formulae (III) and (IV), among $Ar_9$ to $Ar_{16}$, those which are not a substituent represented by the general formula (V) each represent substituted or unsubstituted aryl group or substituted or unsubstituted polycondensed aromatic group.

Specific examples of an aryl group, a polycondensed aromatic group, and an aryl group, and a substituent which an aryl group and a polycondensed aromatic group may have, represented by $Ar_9$ to $Ar_{16}$, are similar to $Ar_1$ to $Ar_8$ in the formulae (I) and (II).

The fluorene compound of the present invention contains at least one substituent which is presented by the formula (V). More preferably, the fluorene compound of the present invention contains a substituent represented by the formula (V) in all the four substituents.

In the fluorene compound of the present invention, a bulky aryl group and polycondensed aromatic group are introduced into a fluorene skeleton. Therefore, the flatness of the entire molecules is suppressed. Thus, according to the fluorene compound of the present invention, when a thin film is formed by vacuum vapor deposition or solution coating, the formed thin film is unlikely to be crystallized or the like, and is excellent in stability with the passage of time.

Next, specific configurations of typical examples of the fluorene compound of the present invention will be shown. It should be noted that the present invention is not limited thereto.

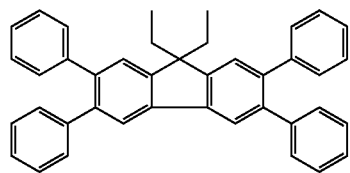

(No. 1)

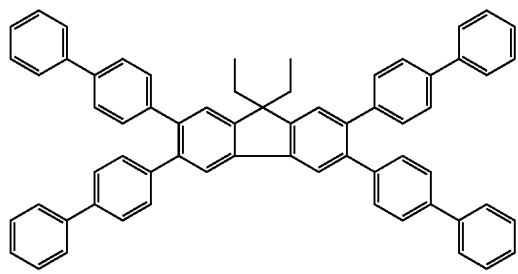

(No. 2)

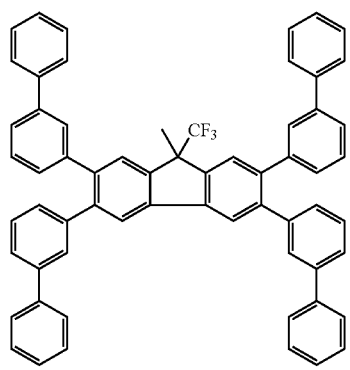

(No. 3)

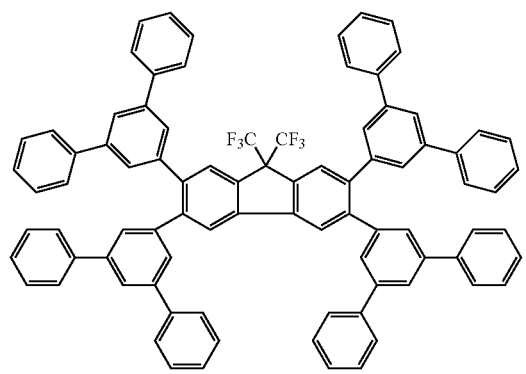

(No. 4)

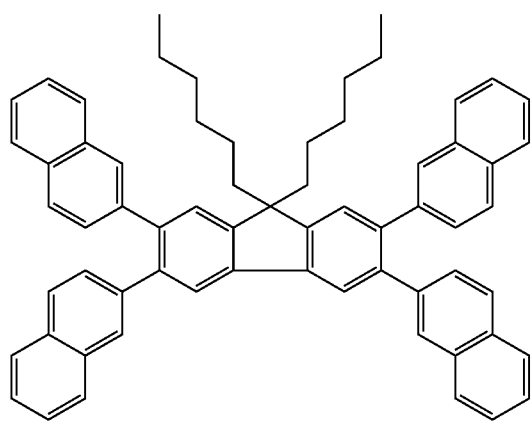

(No. 5)

(No. 6)
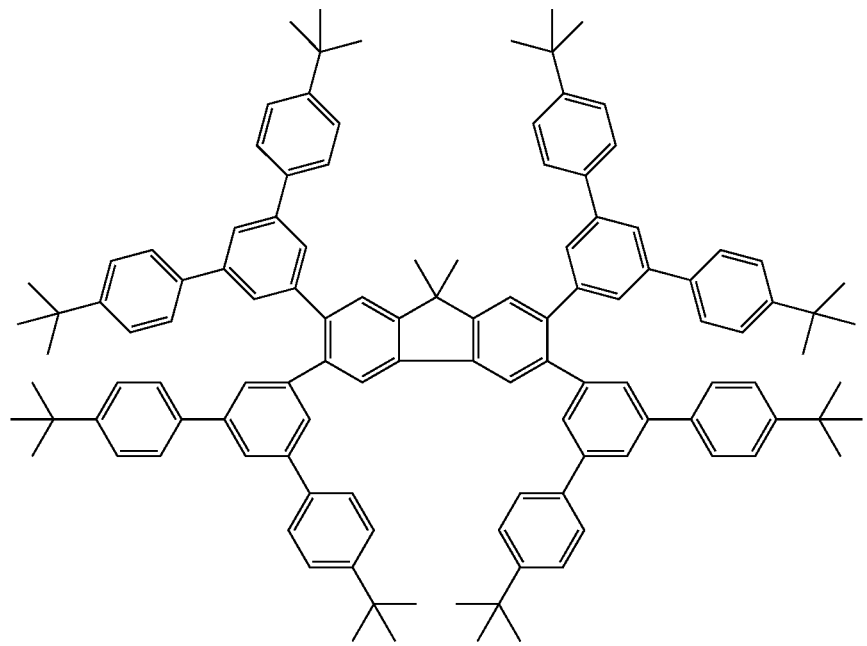
(No. 7)
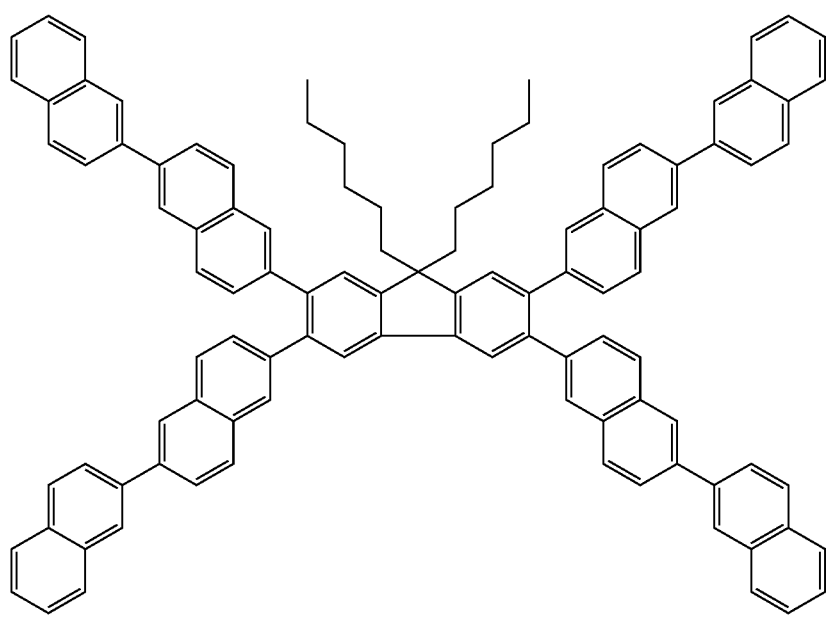
(No. 8)
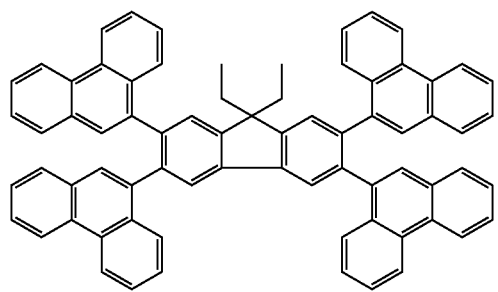
(No. 9)
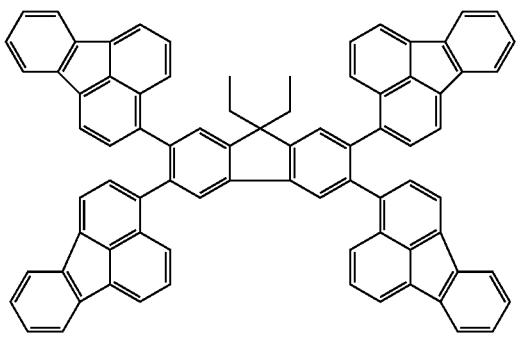

(No. 10)
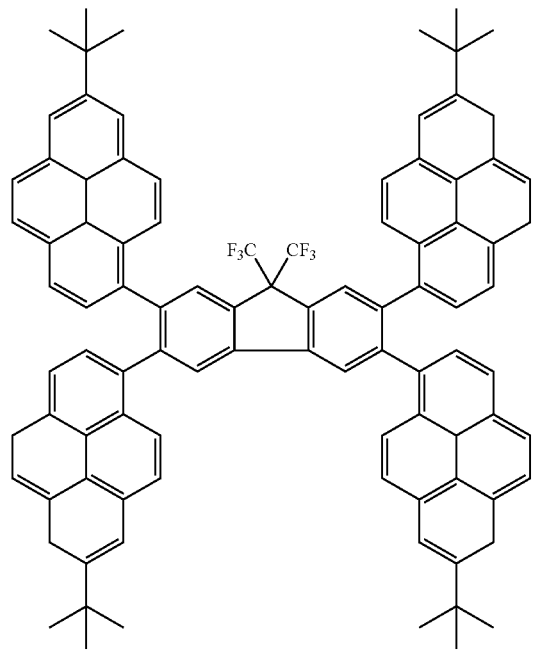
(No. 11)
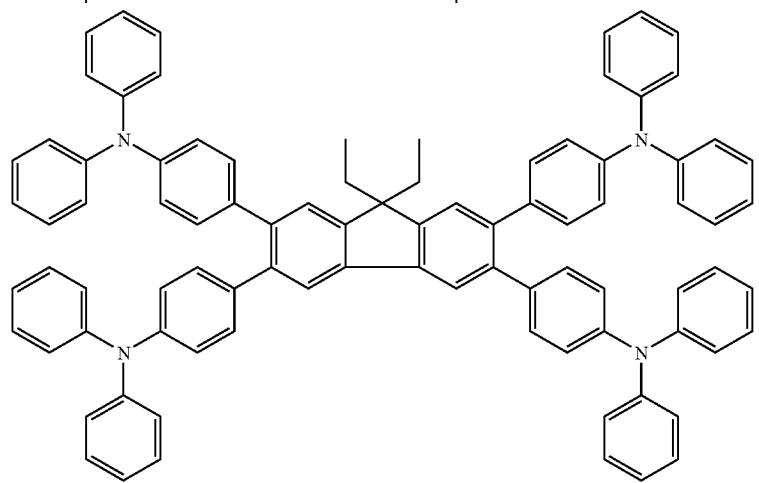
(No. 12)
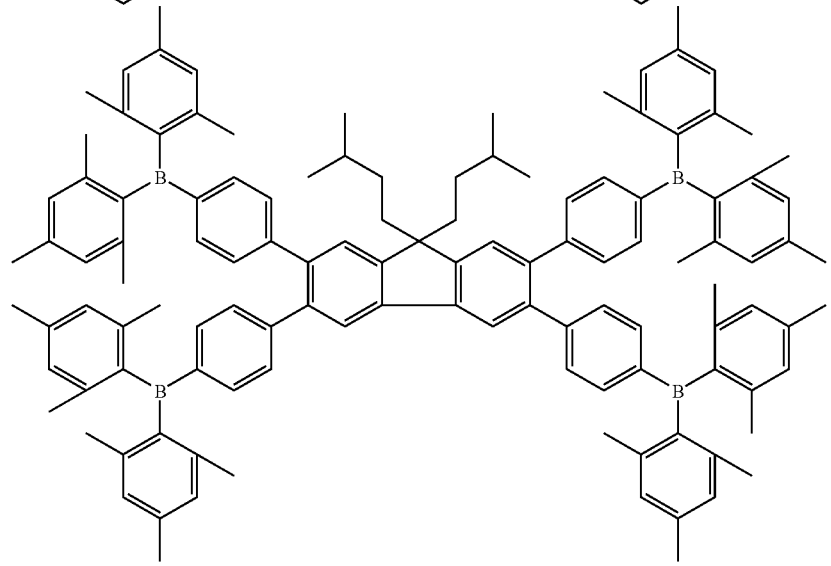

-continued
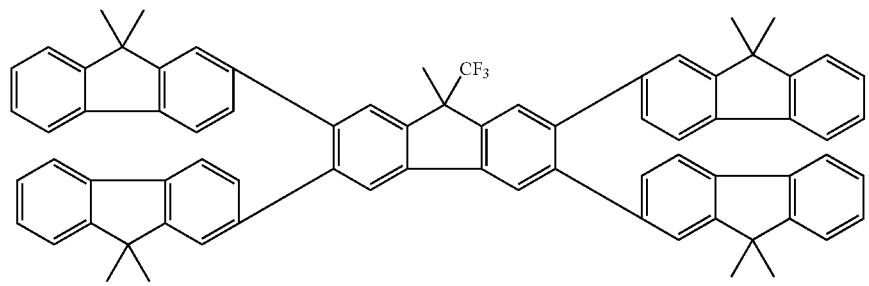
(No. 13)
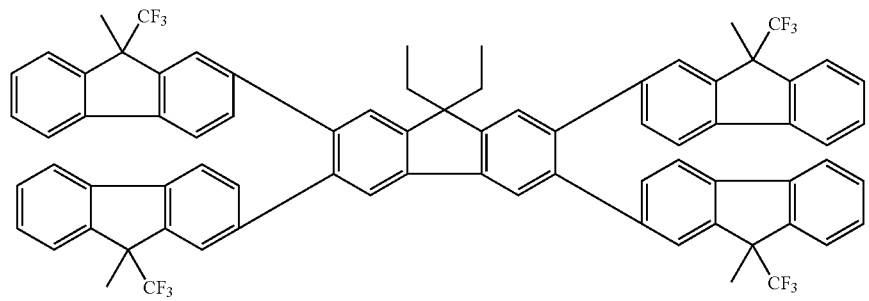
(No. 14)
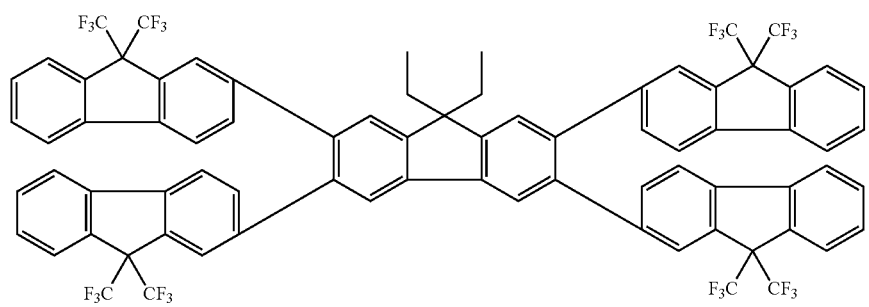
(No. 15)
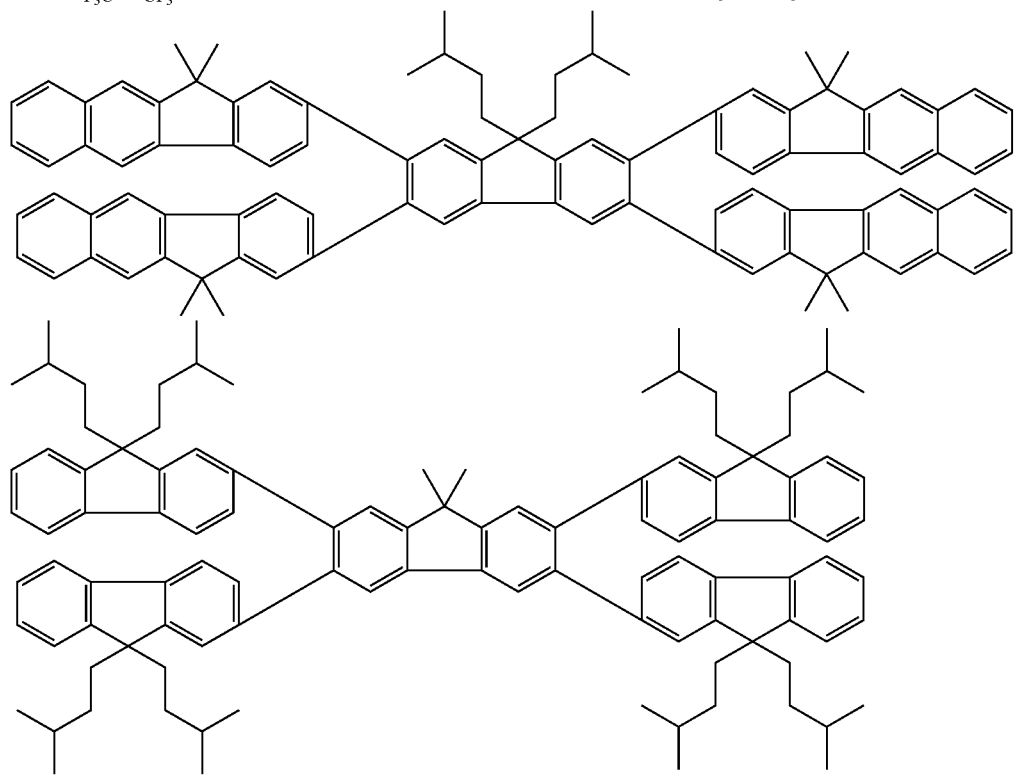
(No. 16)
(No. 17)

(No. 18)
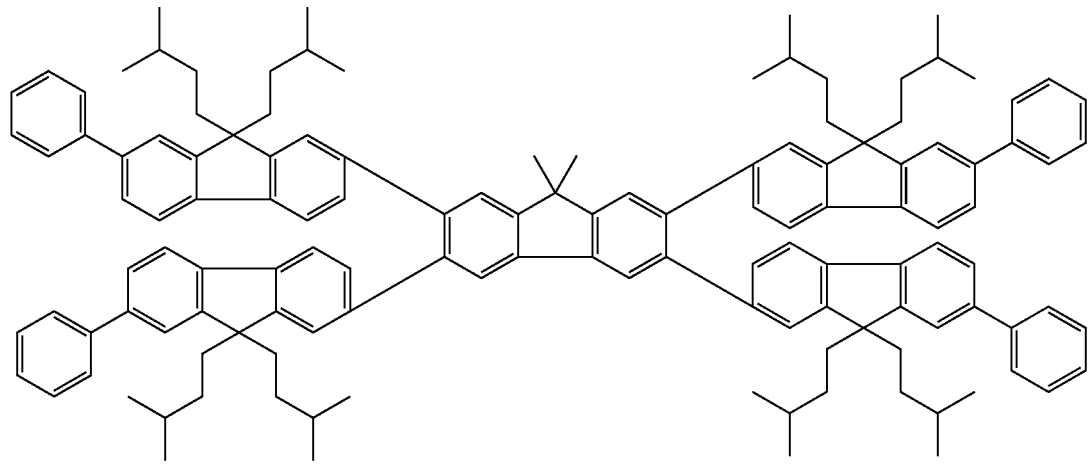
(No. 19)
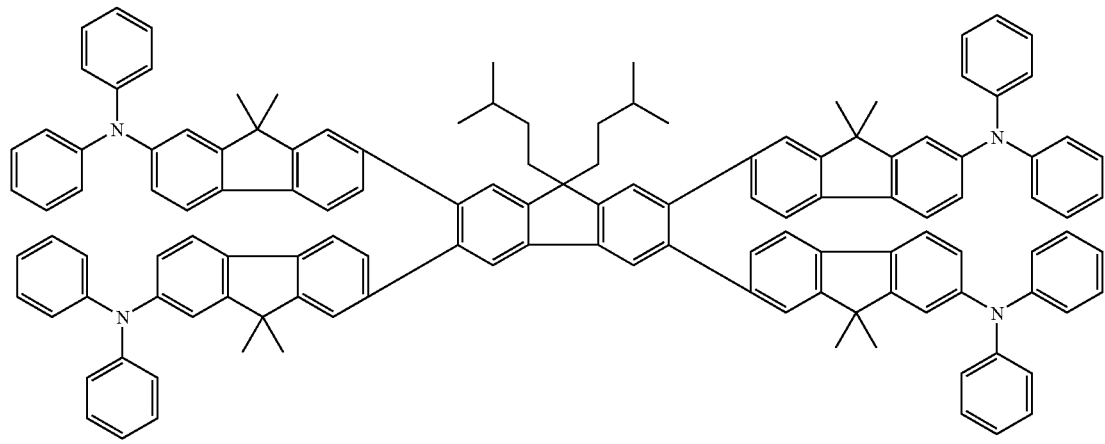
(No. 20)
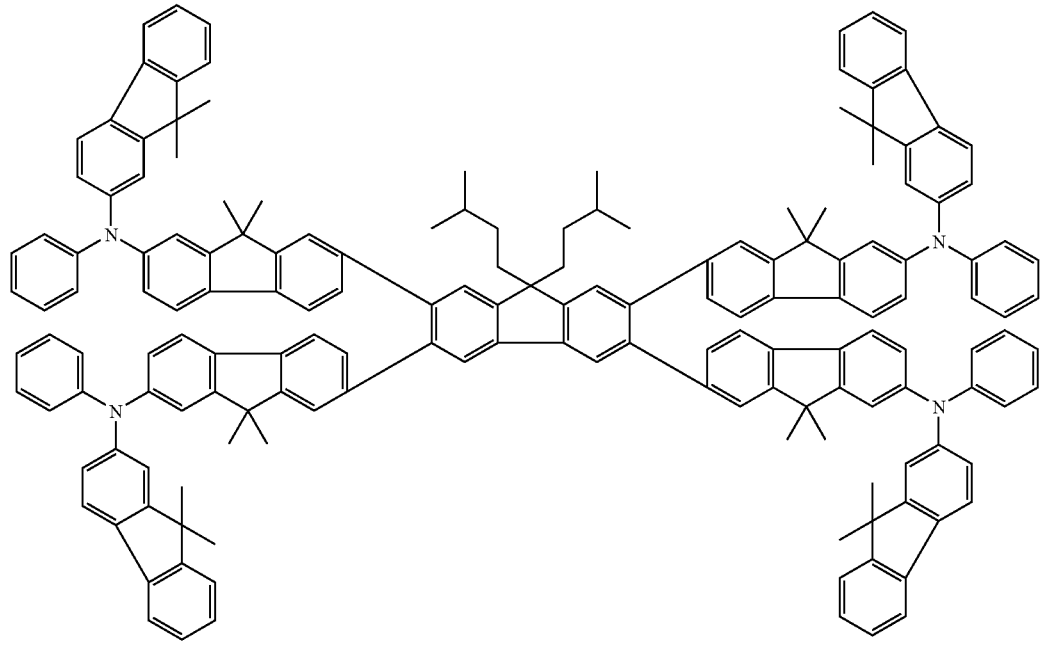

(No. 21)
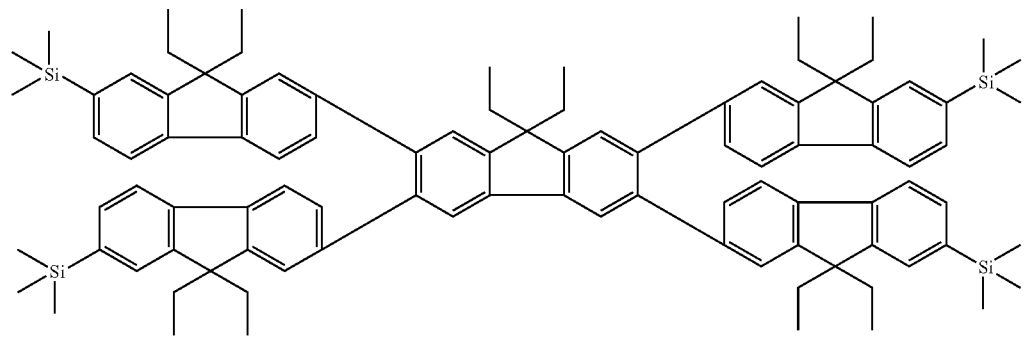
(No. 22)
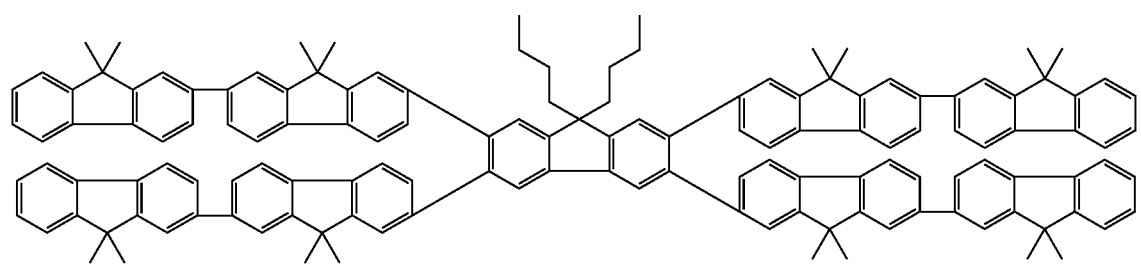
(No. 23)
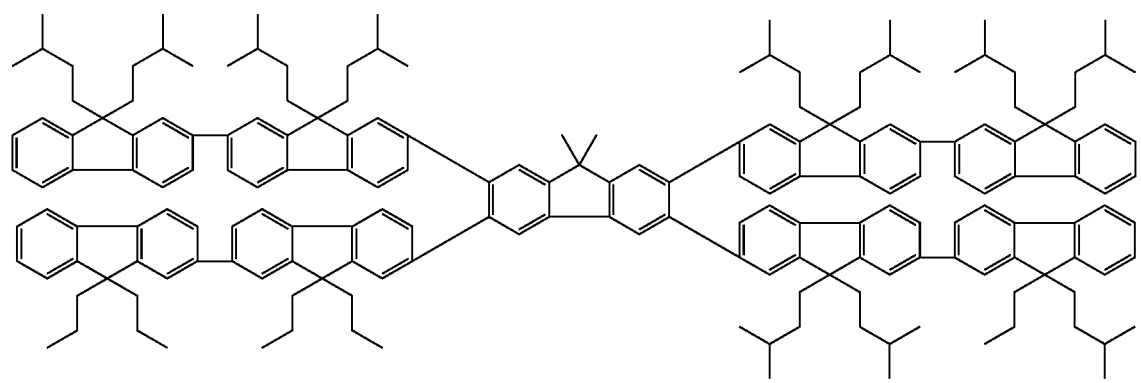
(No. 24)
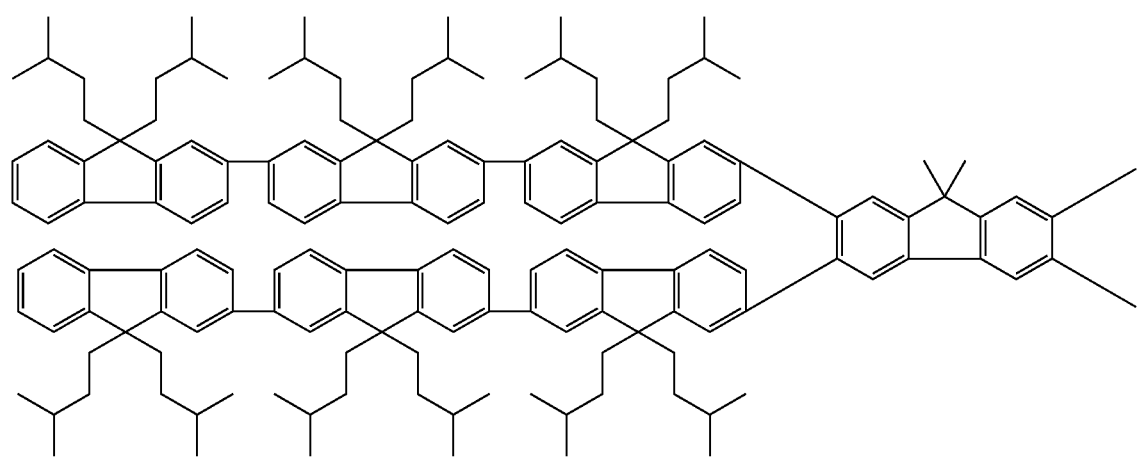

-continued
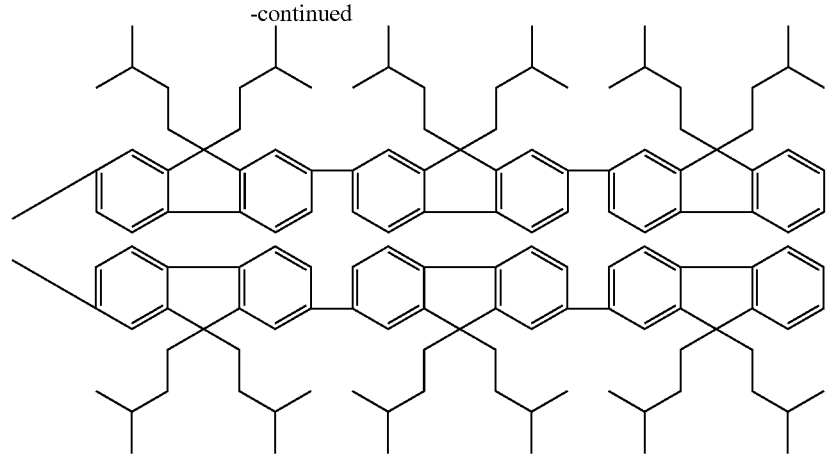
(No. 25)
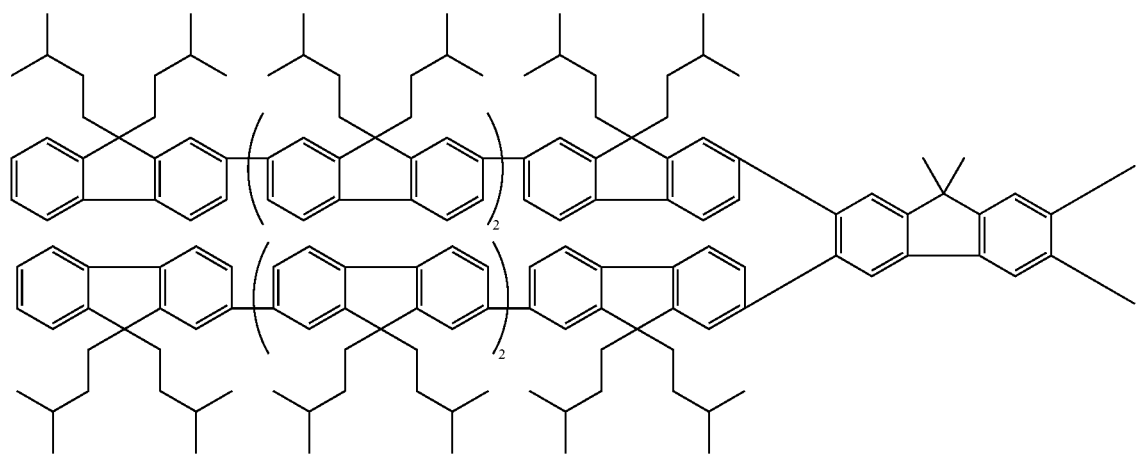
(No. 26)
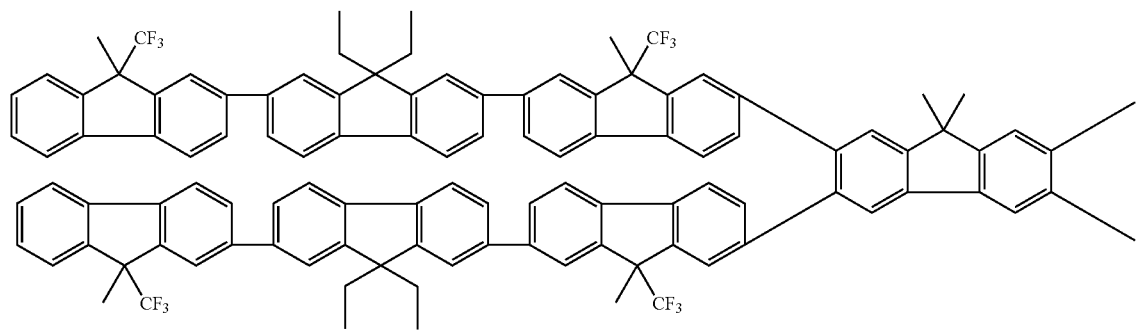

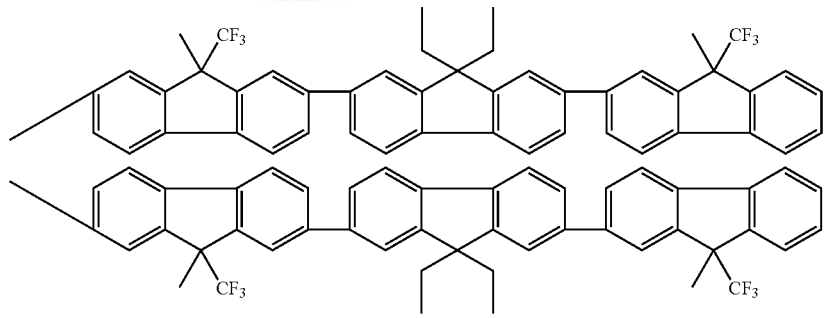
(No. 27)
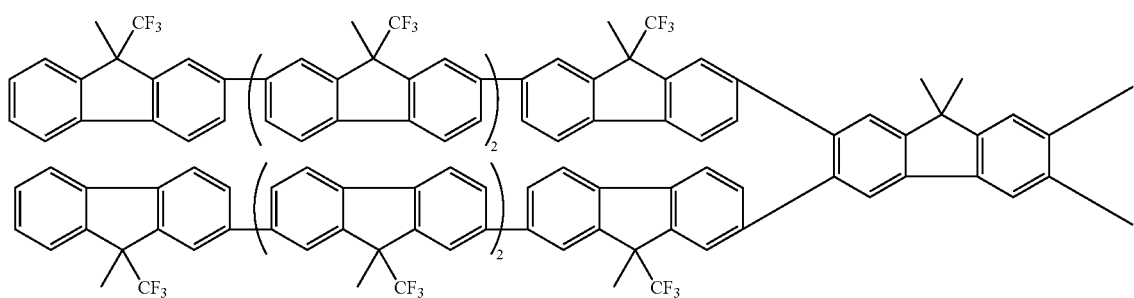
(No. 29)
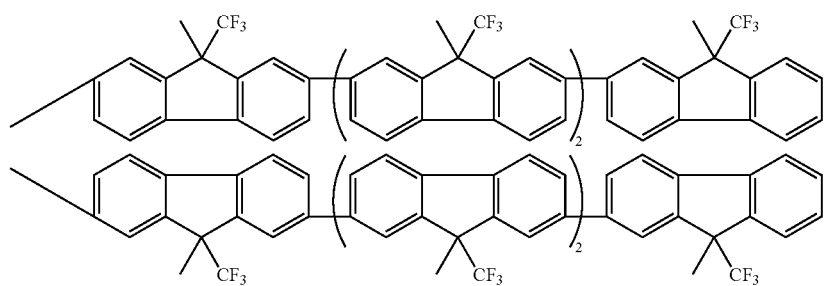
(No. 30)
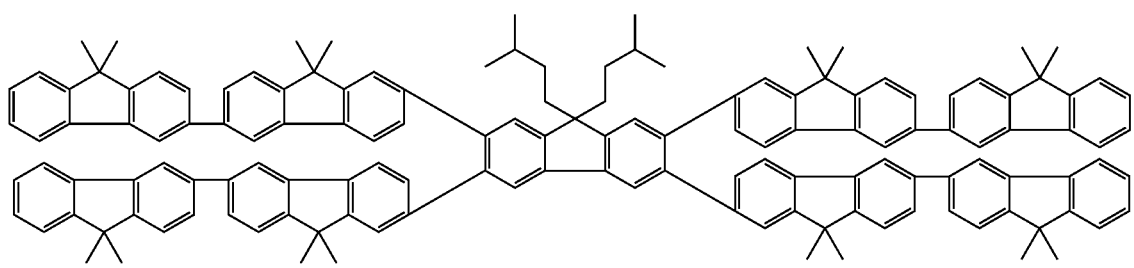
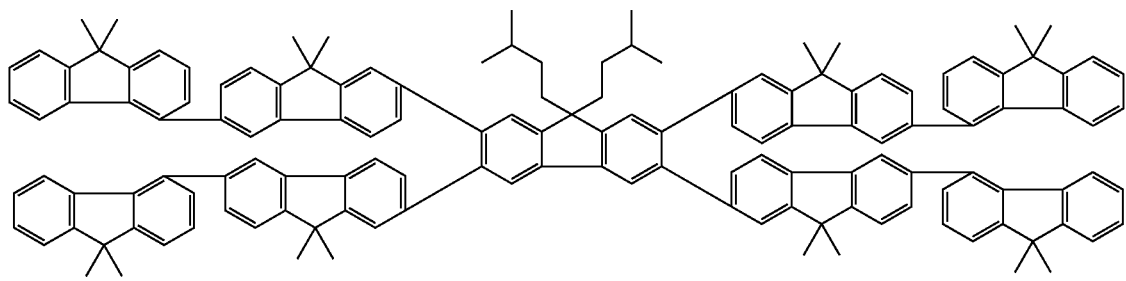

(No. 31)
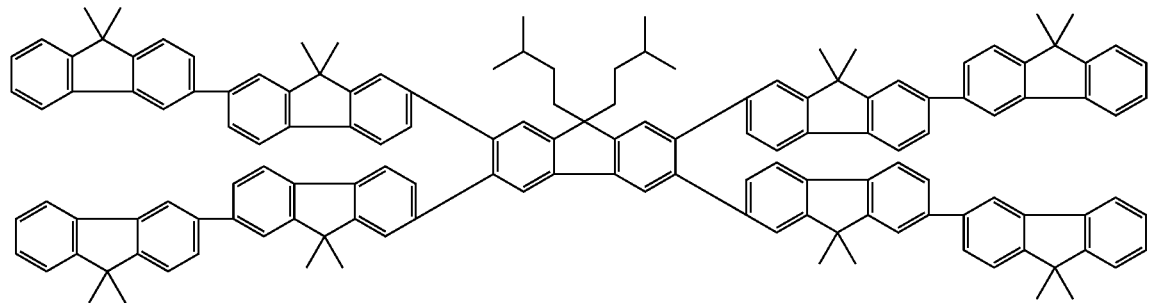
(No. 32)
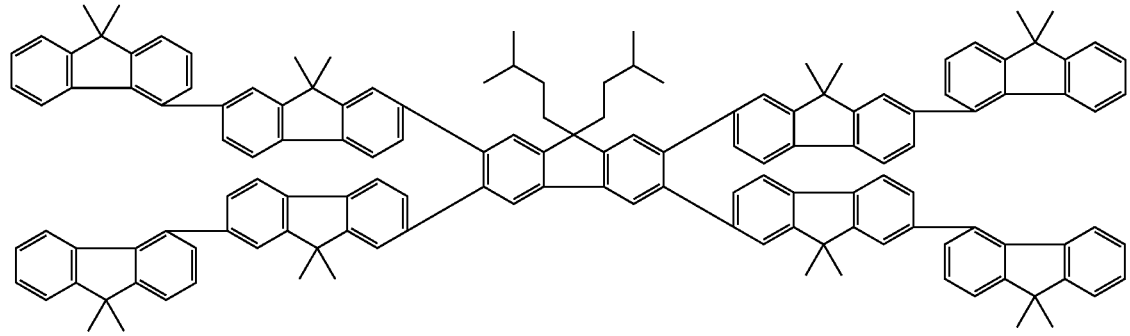
(No. 33)
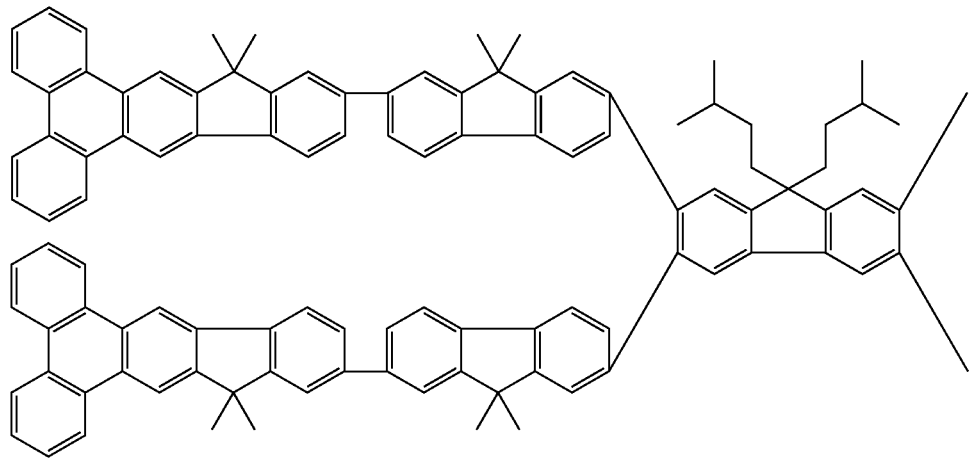
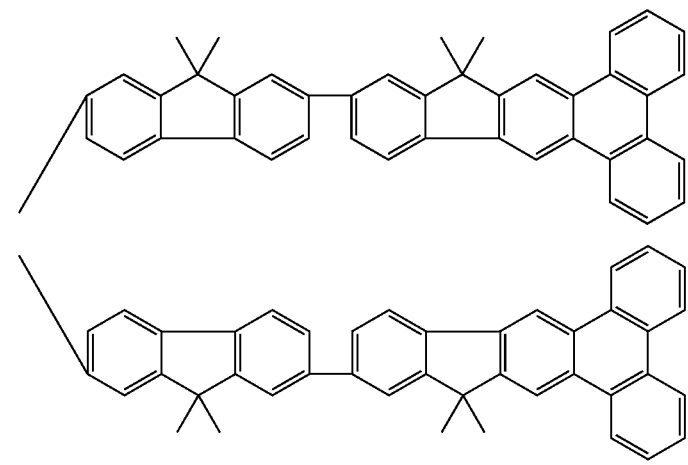

-continued
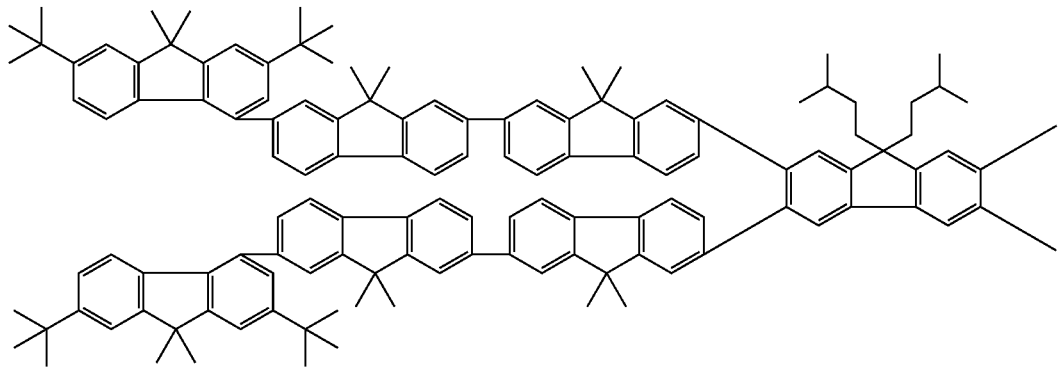
(No. 34)
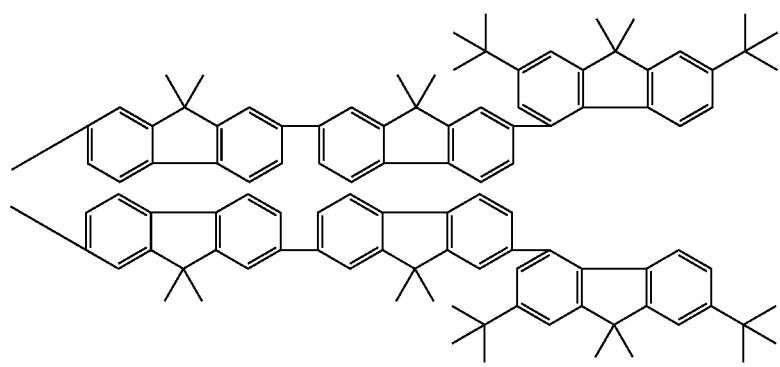
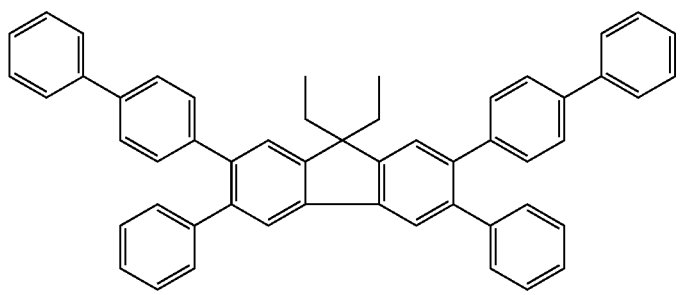
(No. 35)
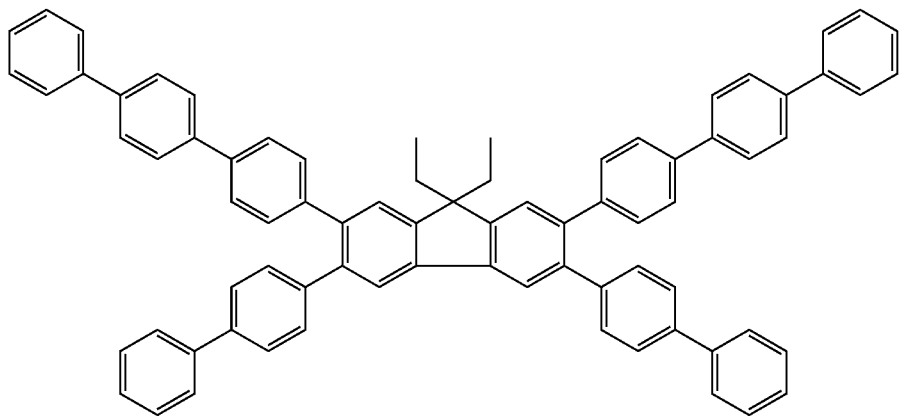
(No. 36)

-continued
(No. 37)
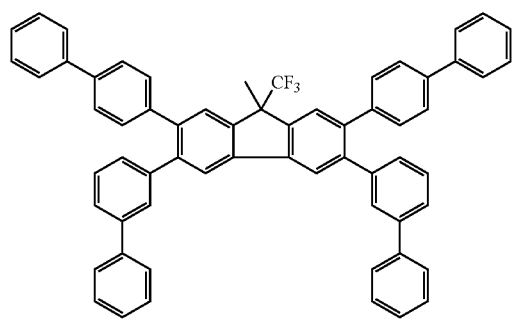
(No. 38)
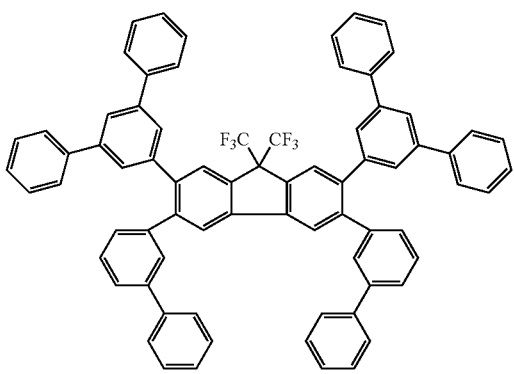
(No. 39)
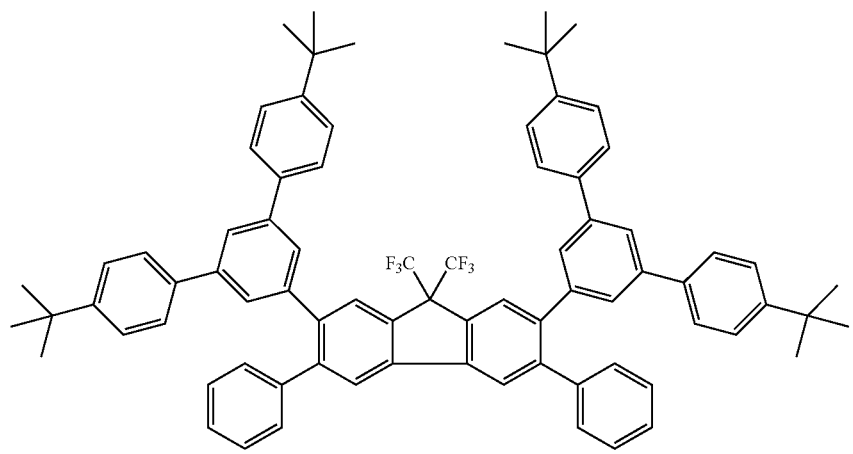
(No. 40)
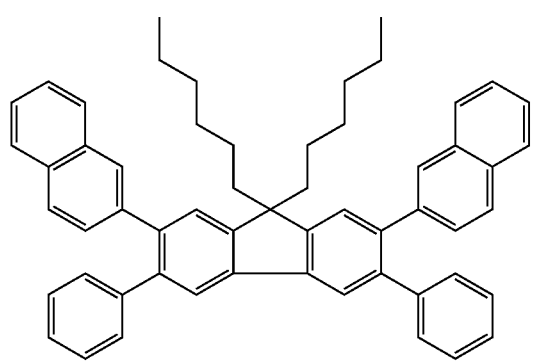
(No. 41)
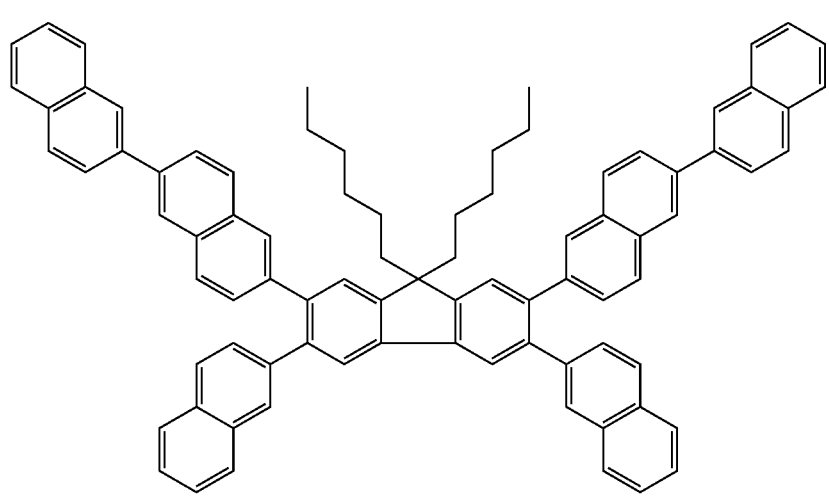

-continued
(No. 42)
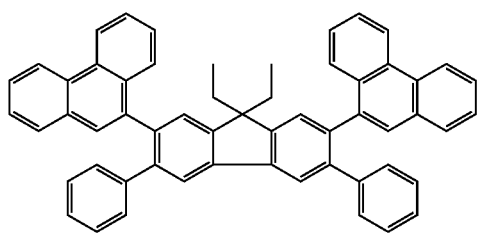
(No. 43)
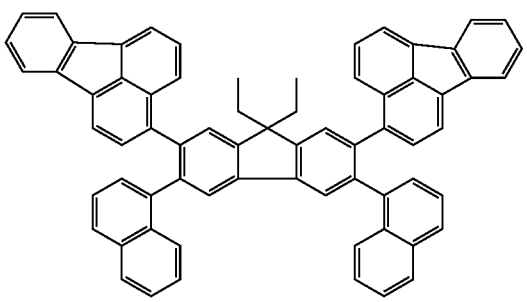
(No. 44)
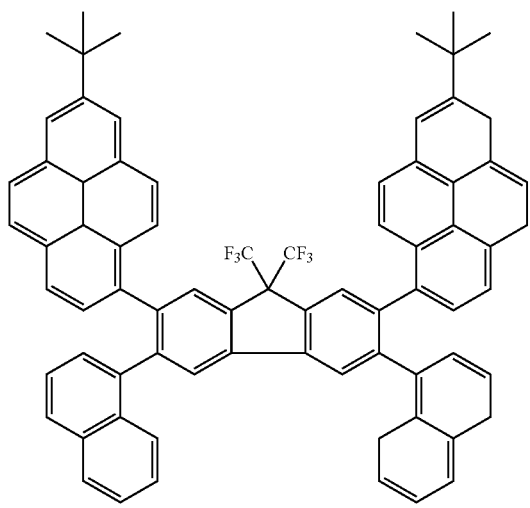
(No. 45)
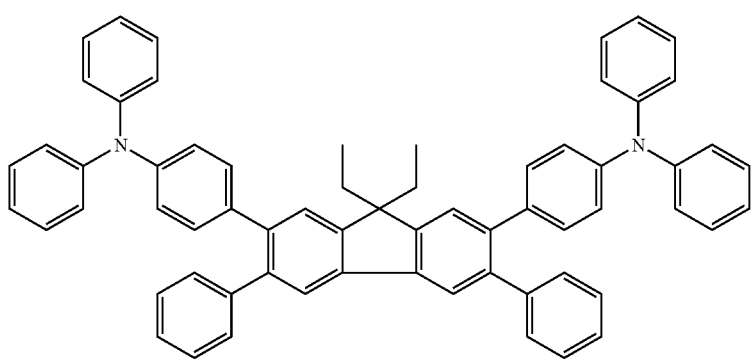
(No. 46)
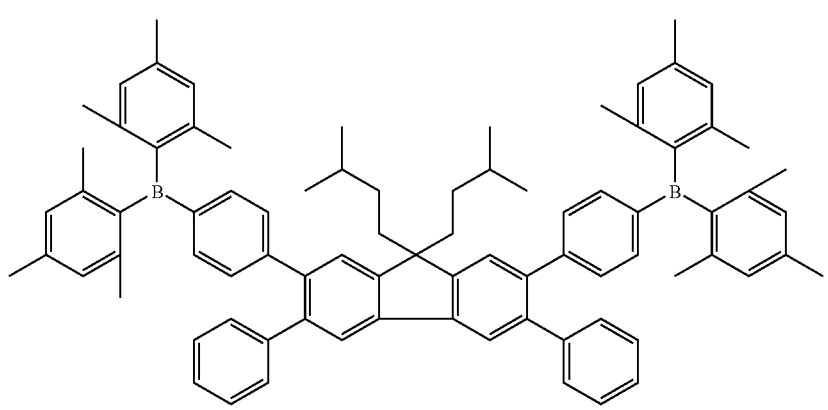

-continued
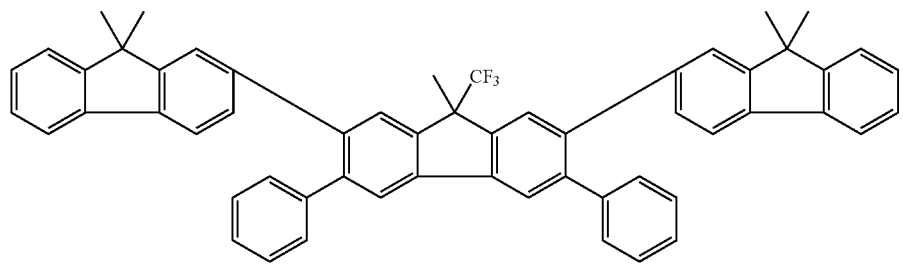
(No. 47)
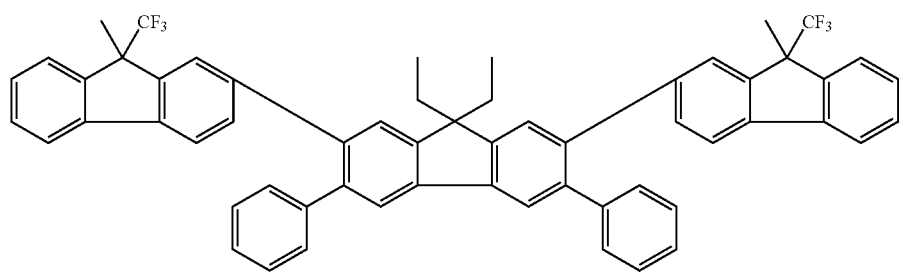
(No. 48)
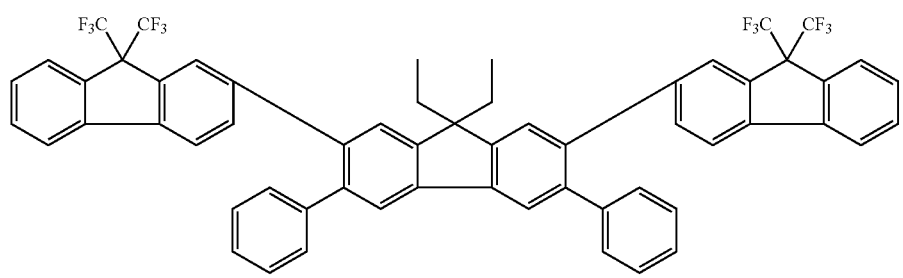
(No. 49)
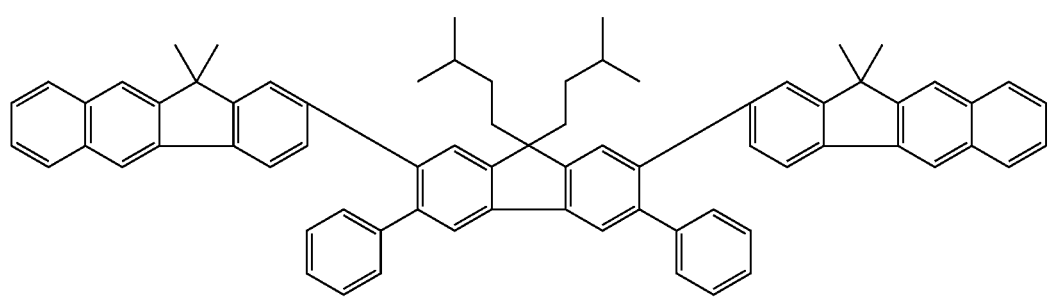
(No. 50)
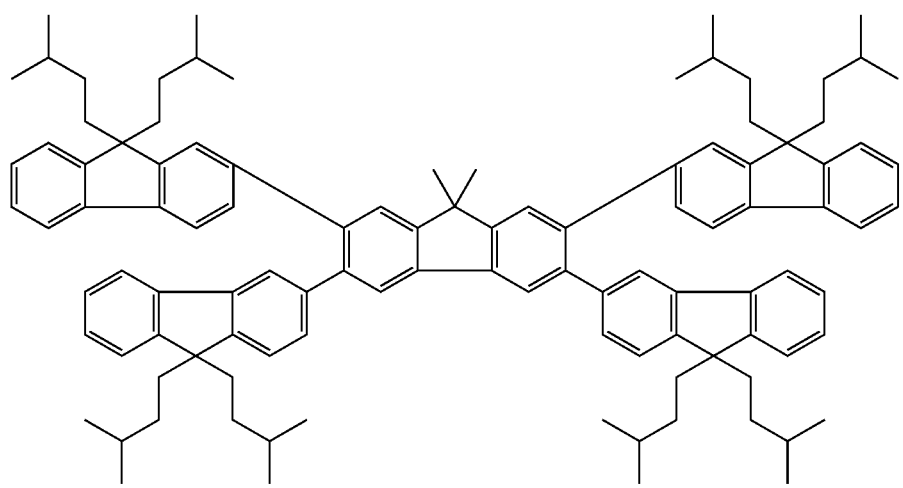
(No. 51)

(No. 52)
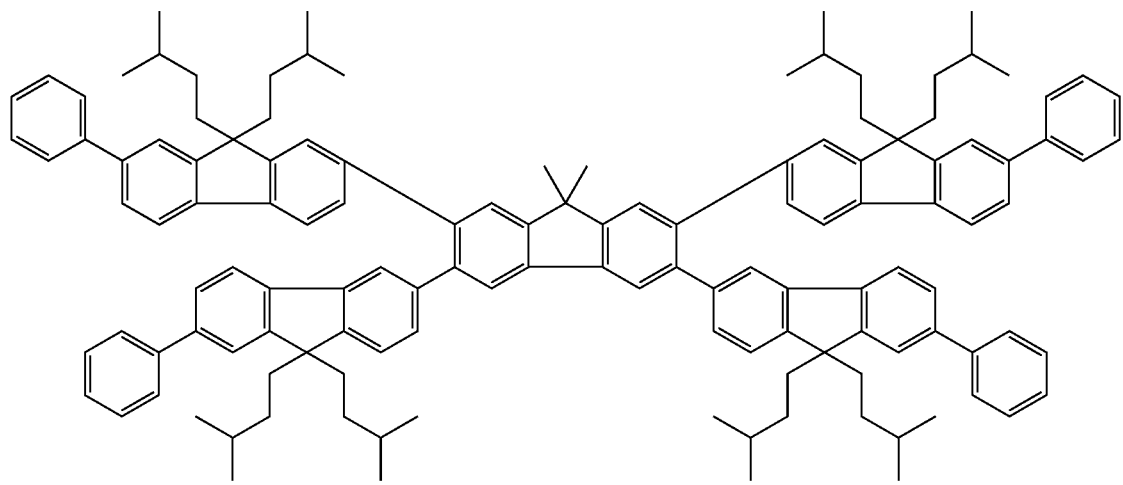
(No. 53)
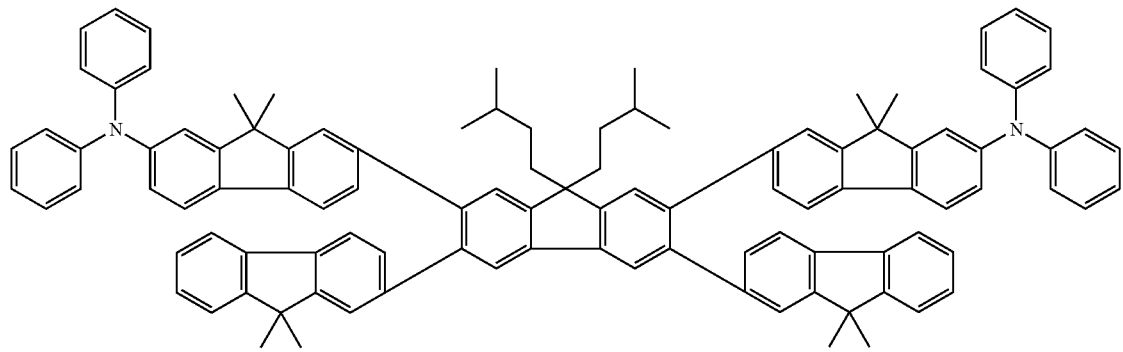
(No. 54)
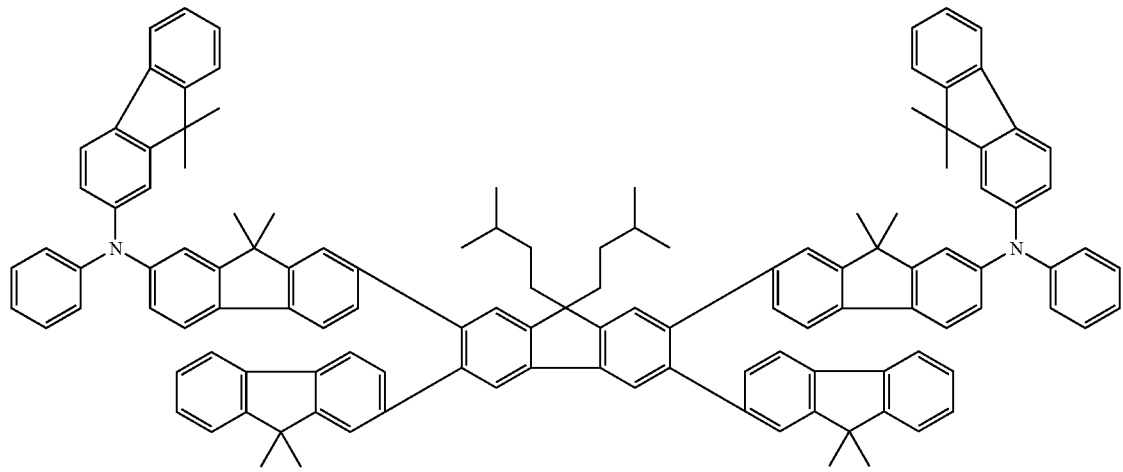
(No. 55)
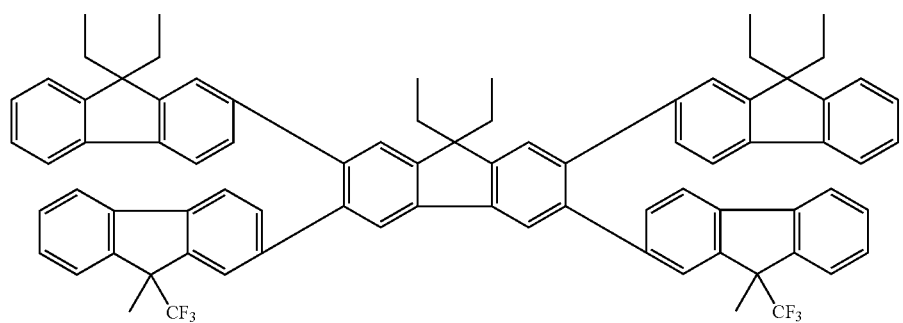

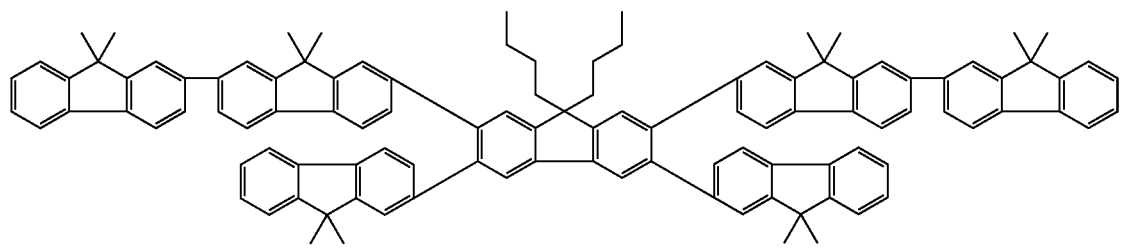
(No. 56)
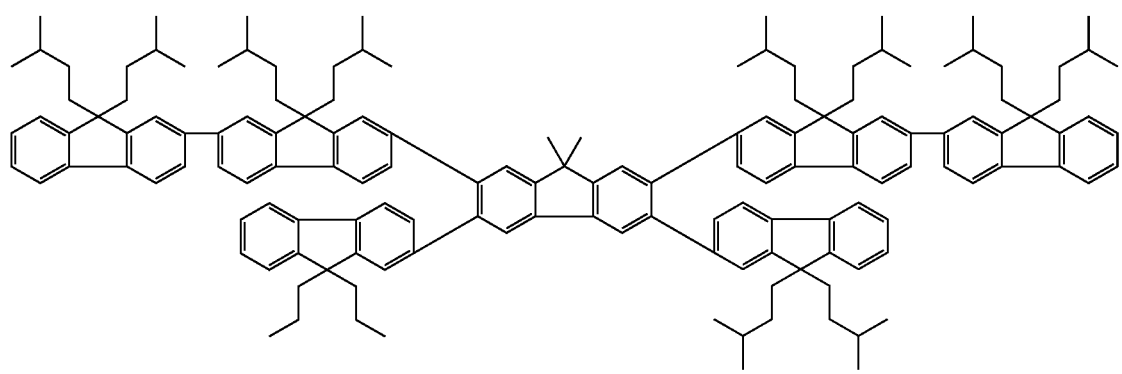
(No. 57)
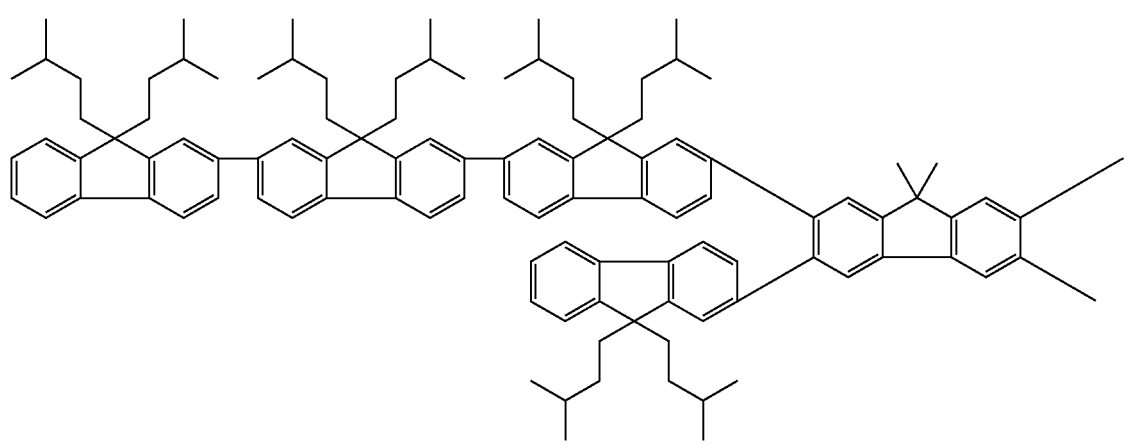
(No. 58)
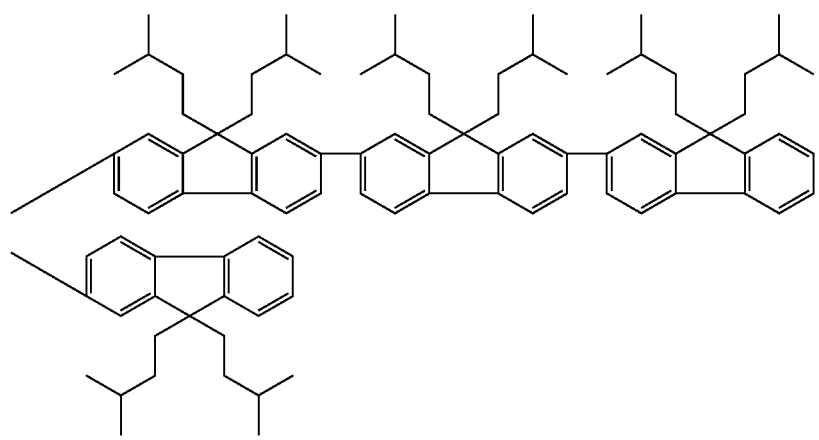

(No. 59)
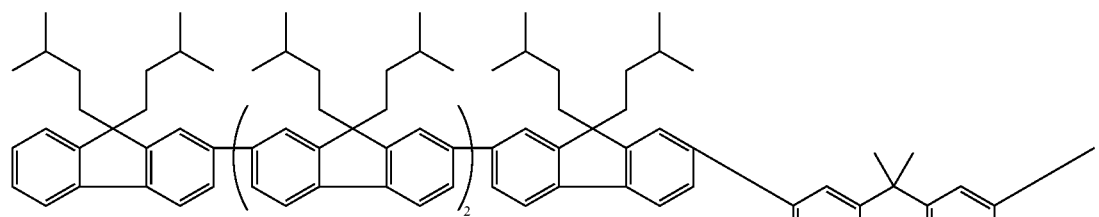
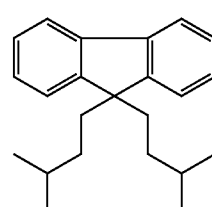
(No. 60)
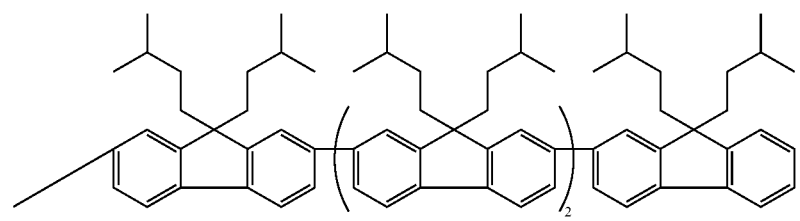
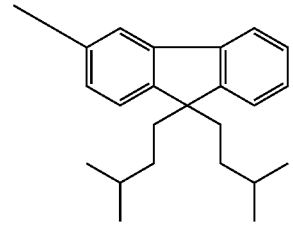
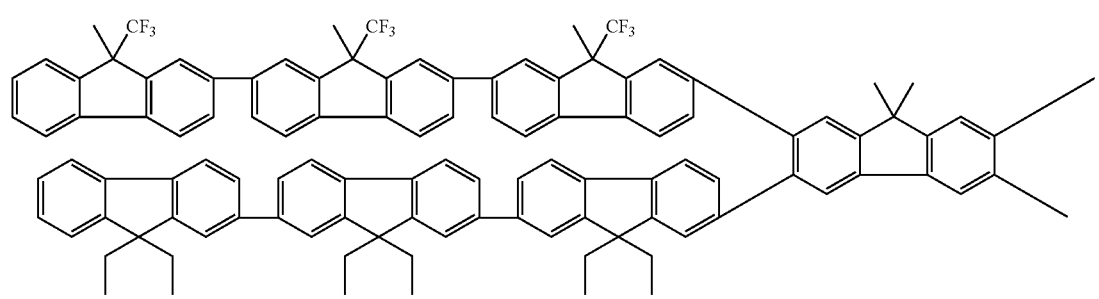
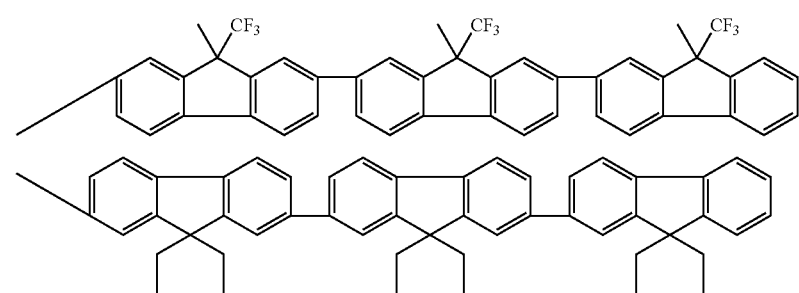

(No. 61)
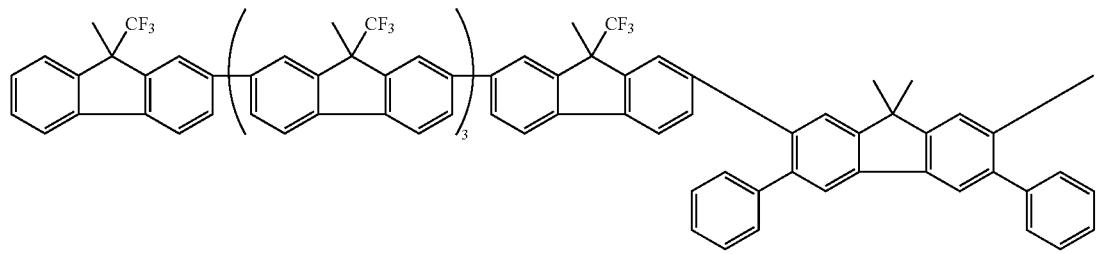
(No. 62)
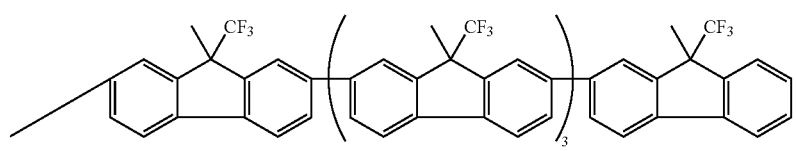
(No. 63)
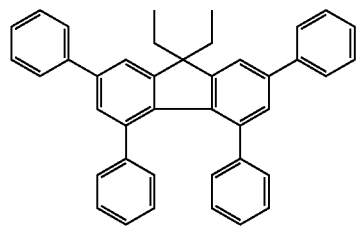
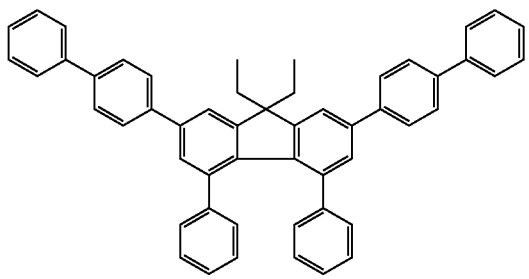
(No. 64)
(No. 65)
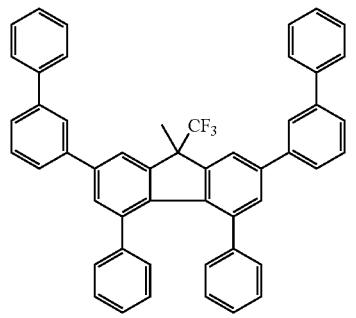
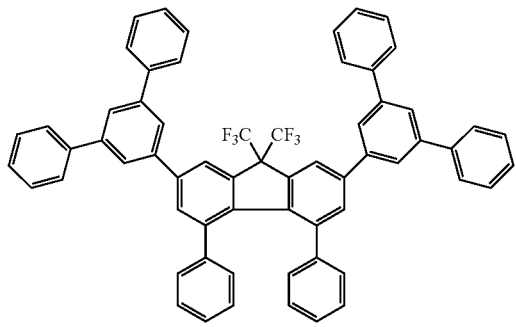
(No. 66)
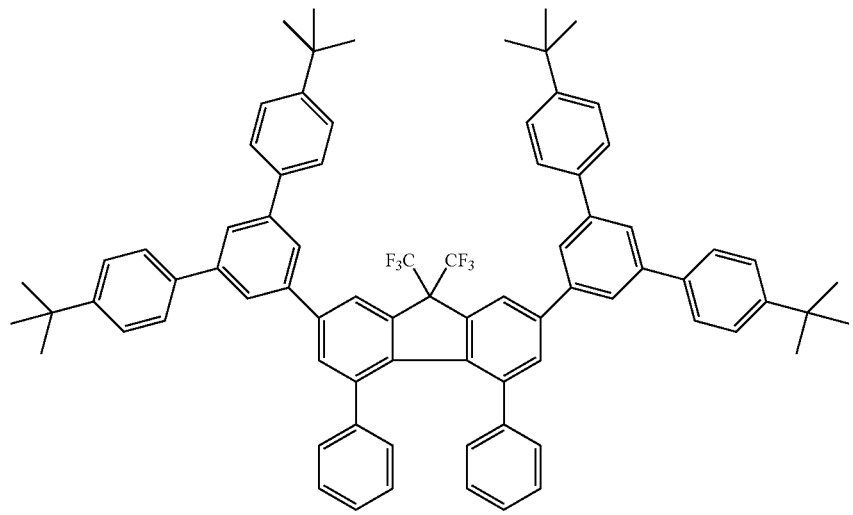

-continued
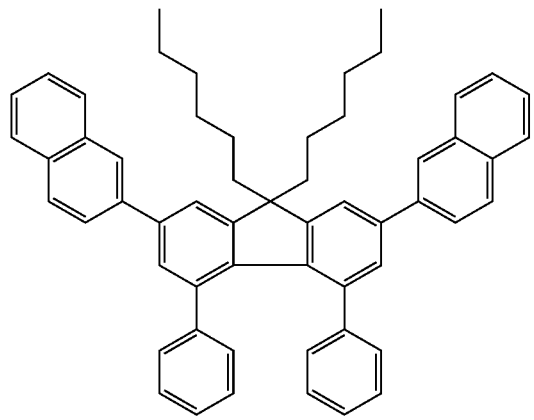
(No. 67)
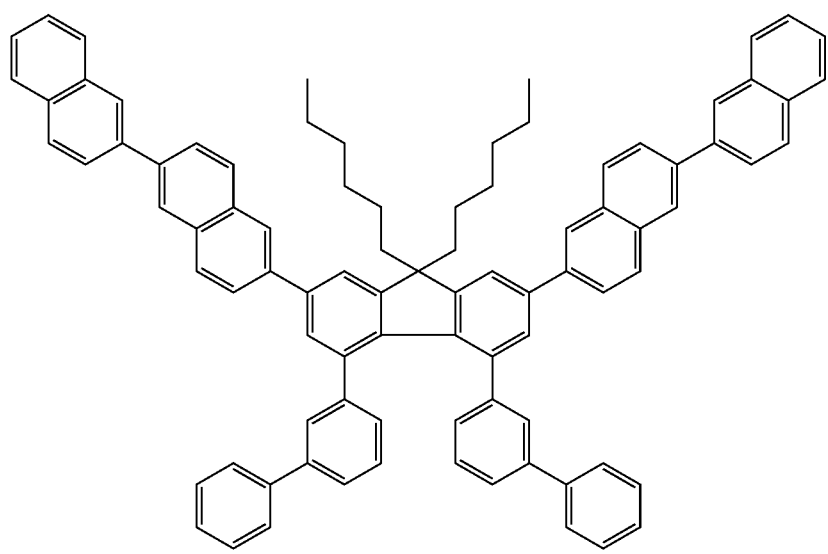
(No. 68)
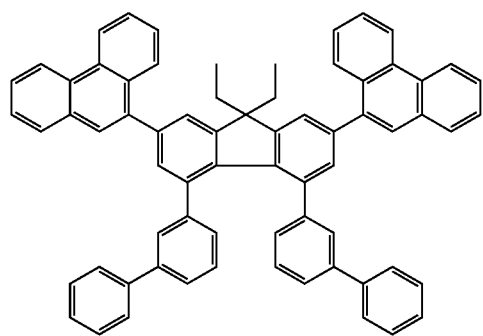
(No. 69)
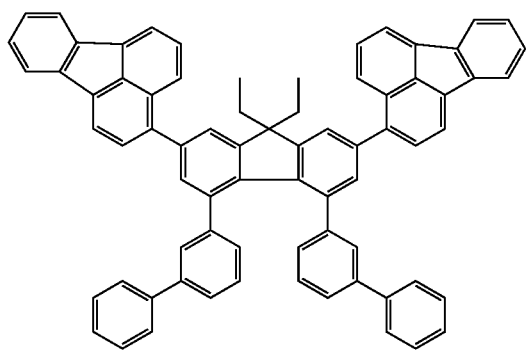
(No. 70)

(No. 71)
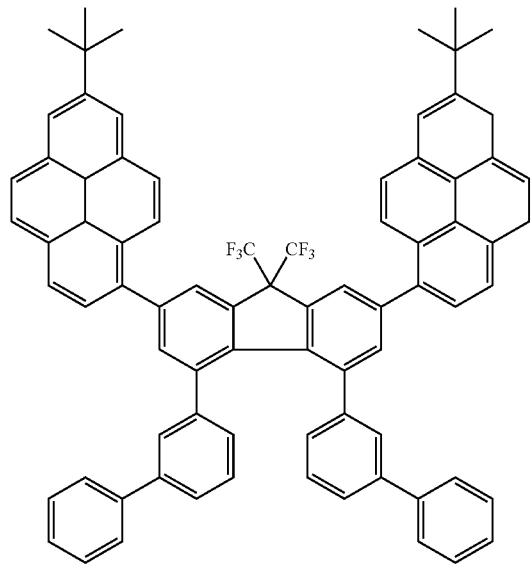
(No. 72)
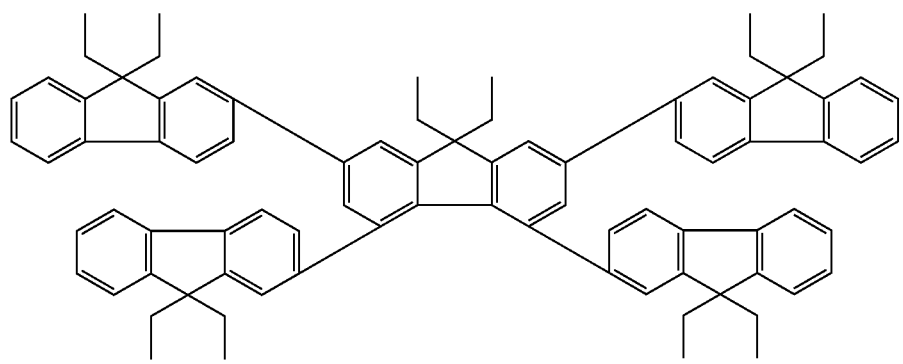
(No. 73)
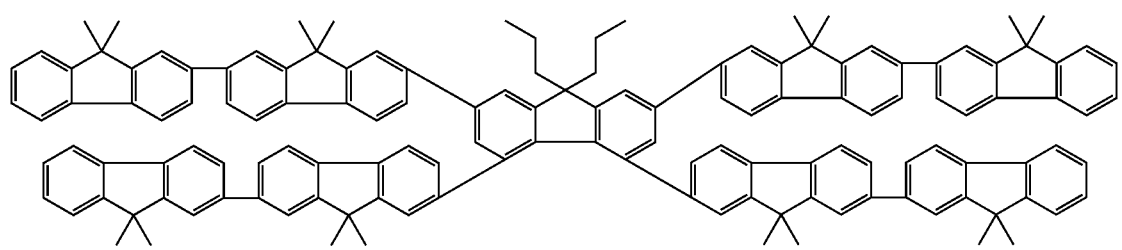
(No. 74)
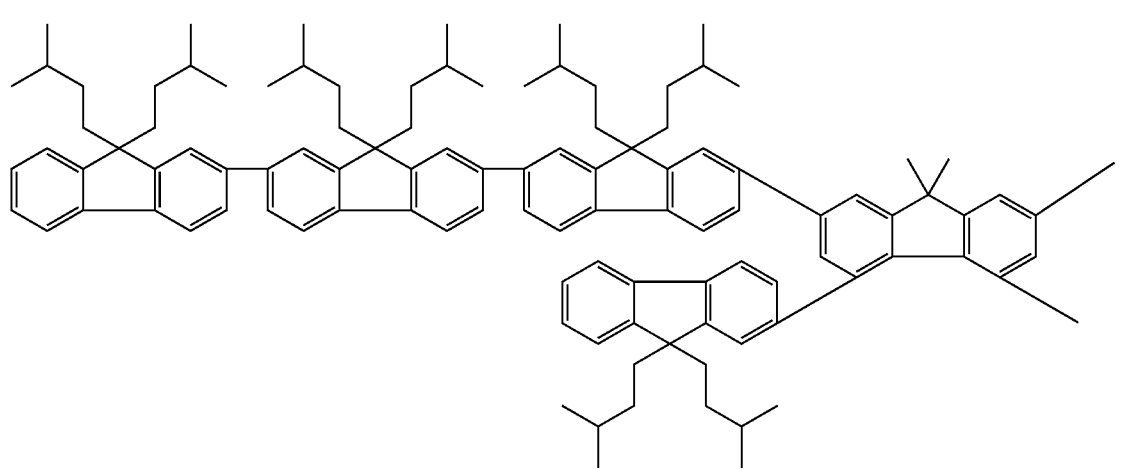

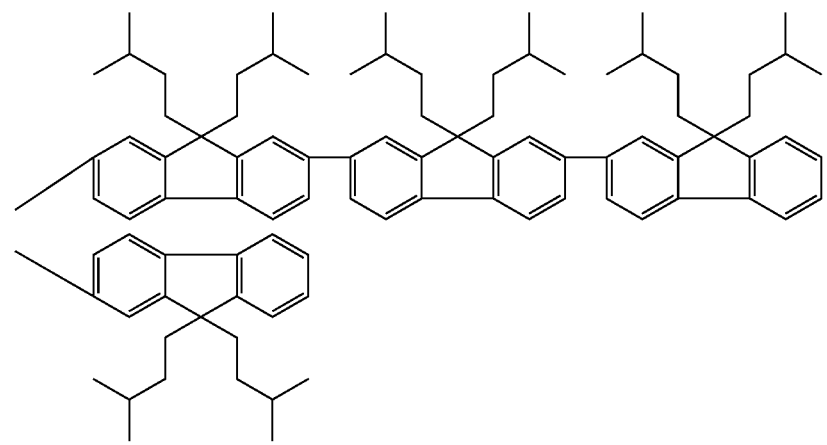
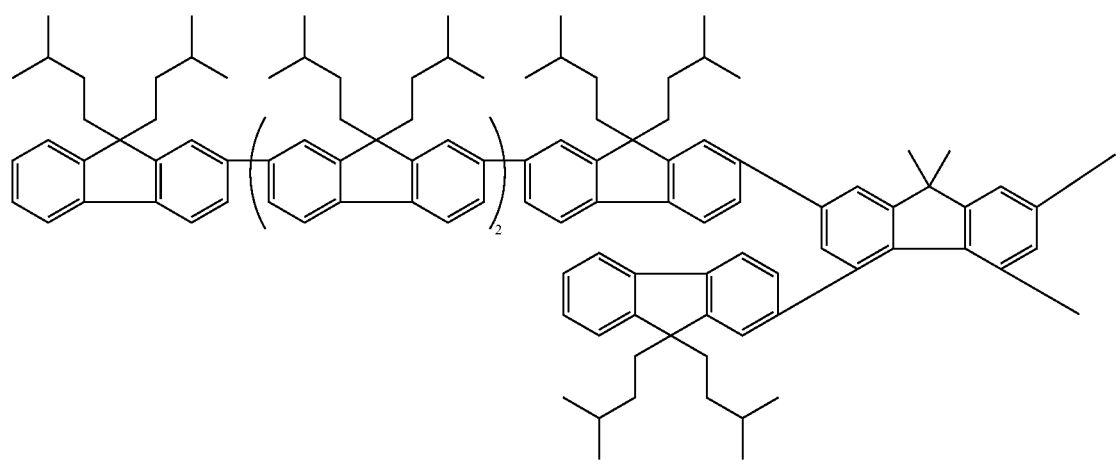
(No. 75)
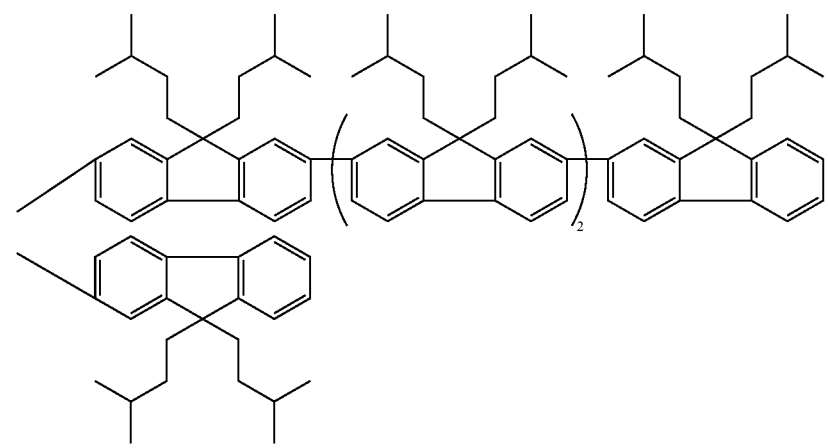

(No. 76)
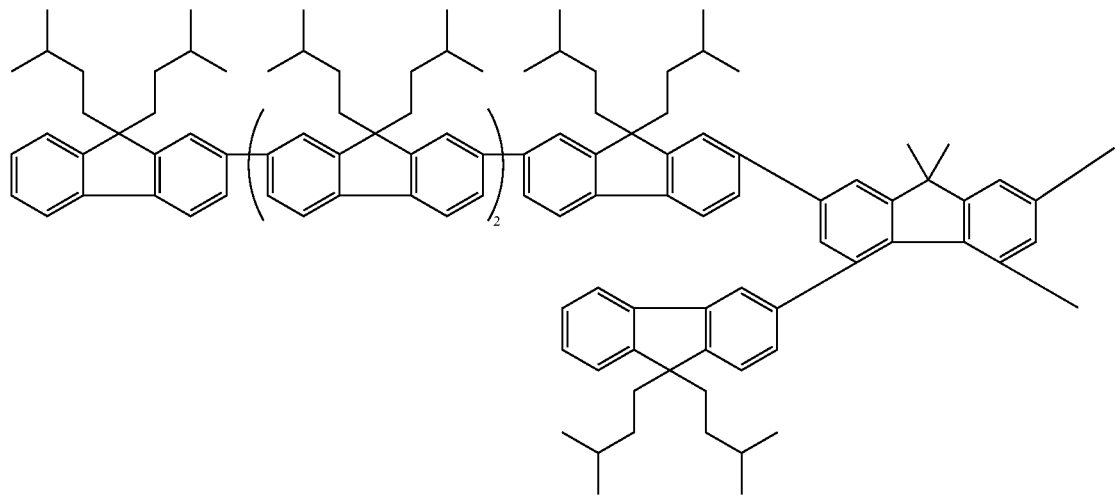
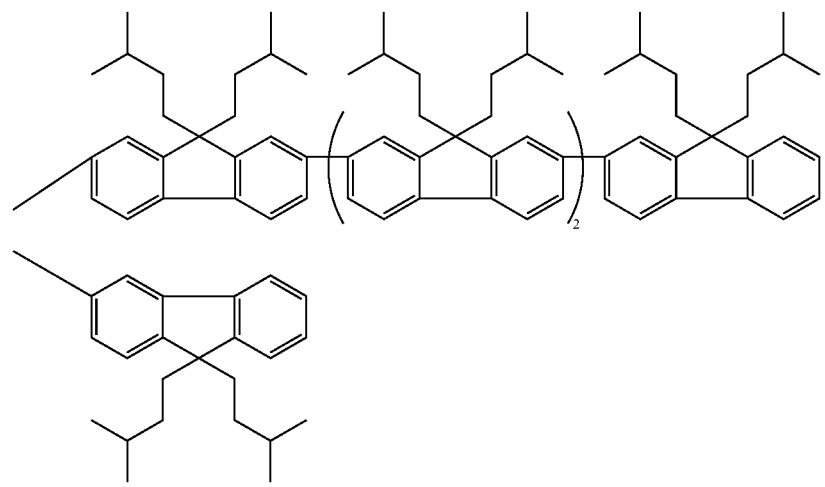
(No. 77)
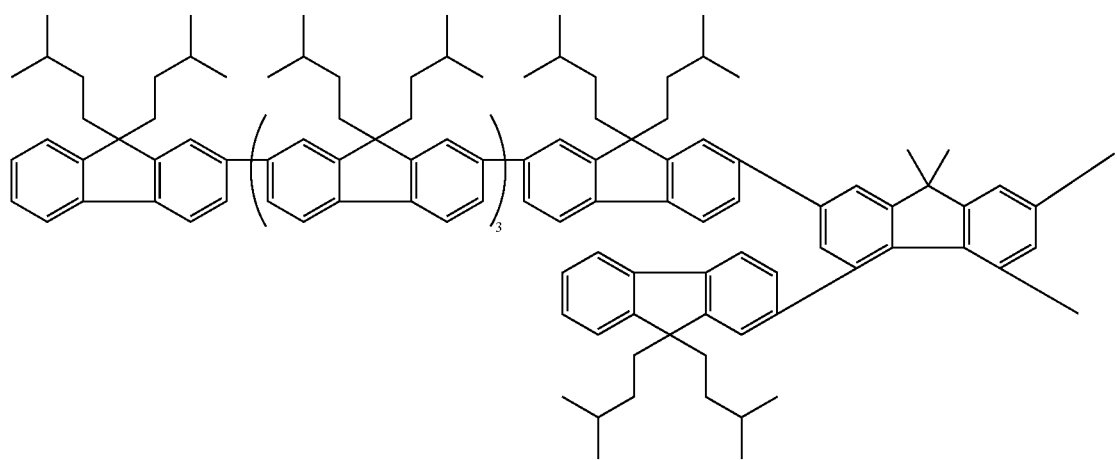

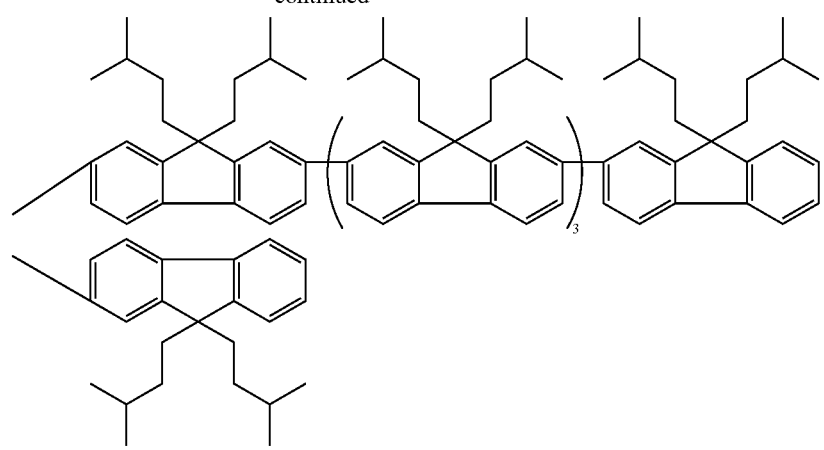
(No. 78)
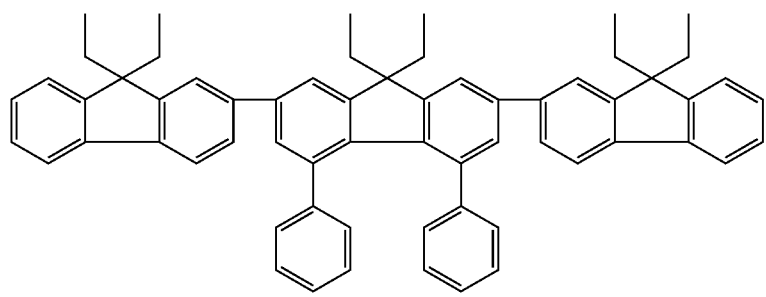
(No. 79)
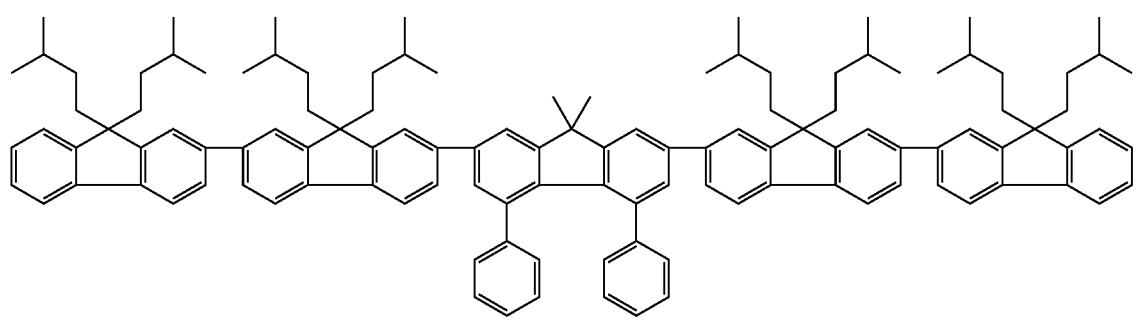
(No. 80)
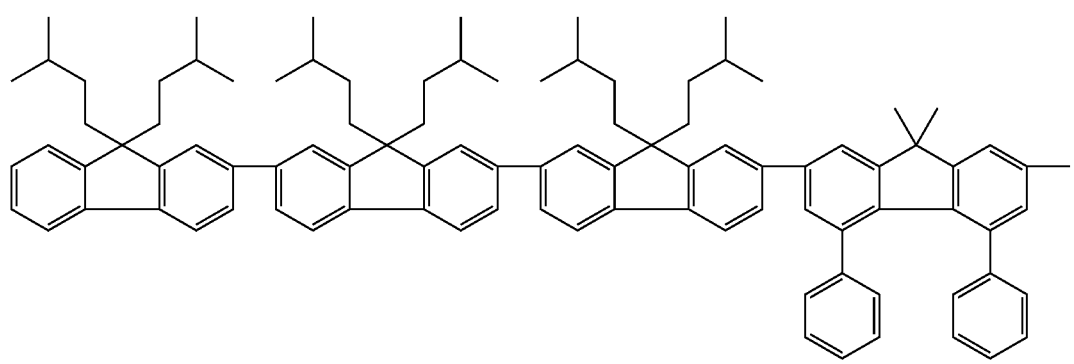
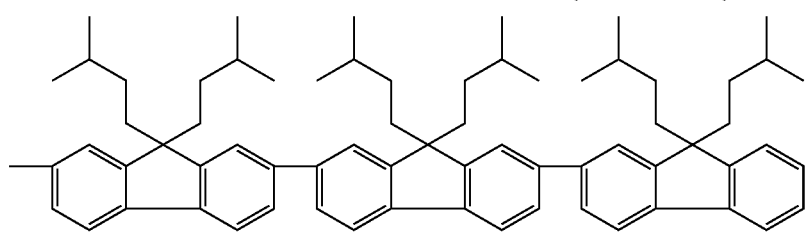

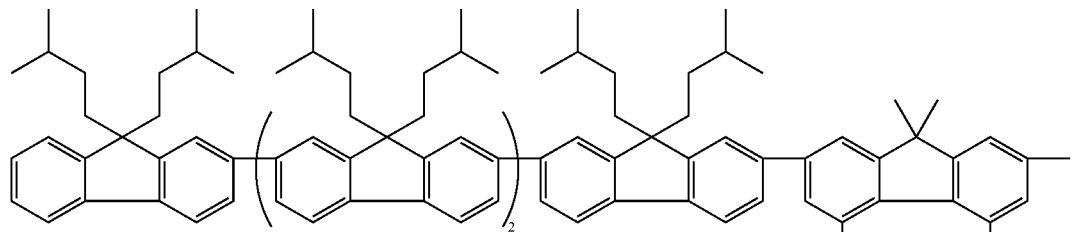
(No. 81)
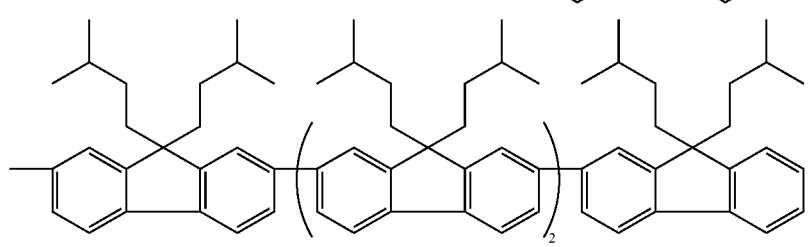
(No. 82)
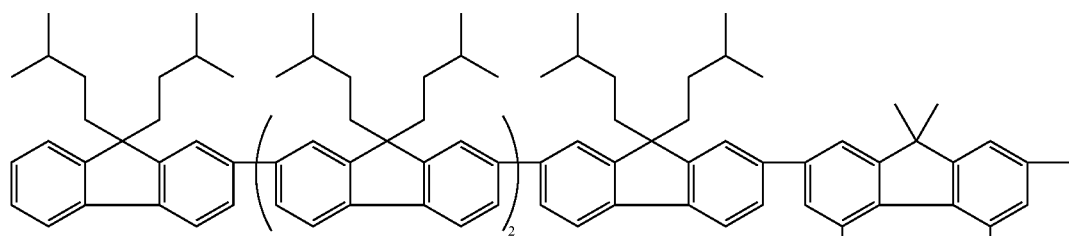
(No. 83)
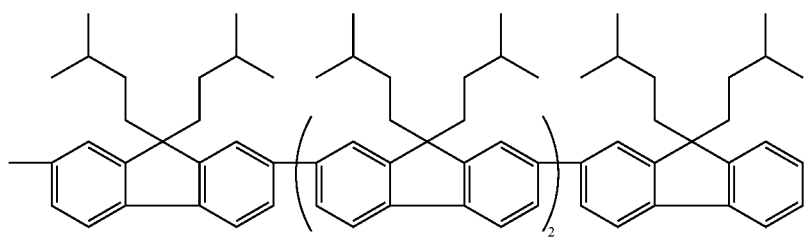
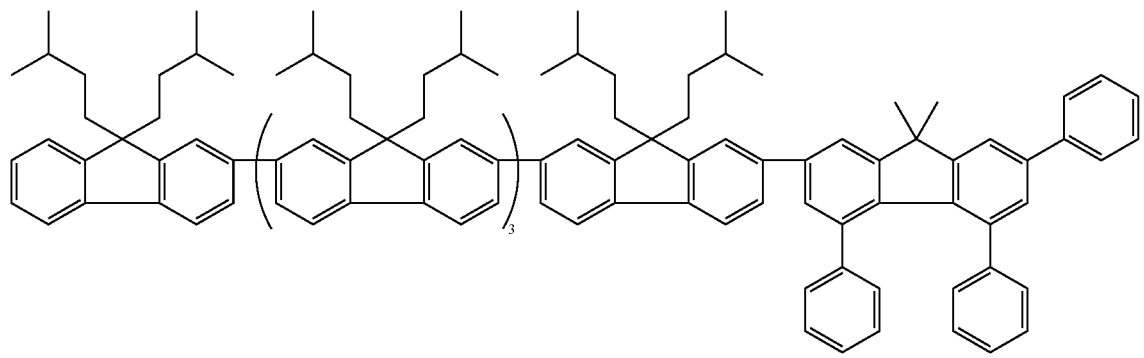

(No. 84)

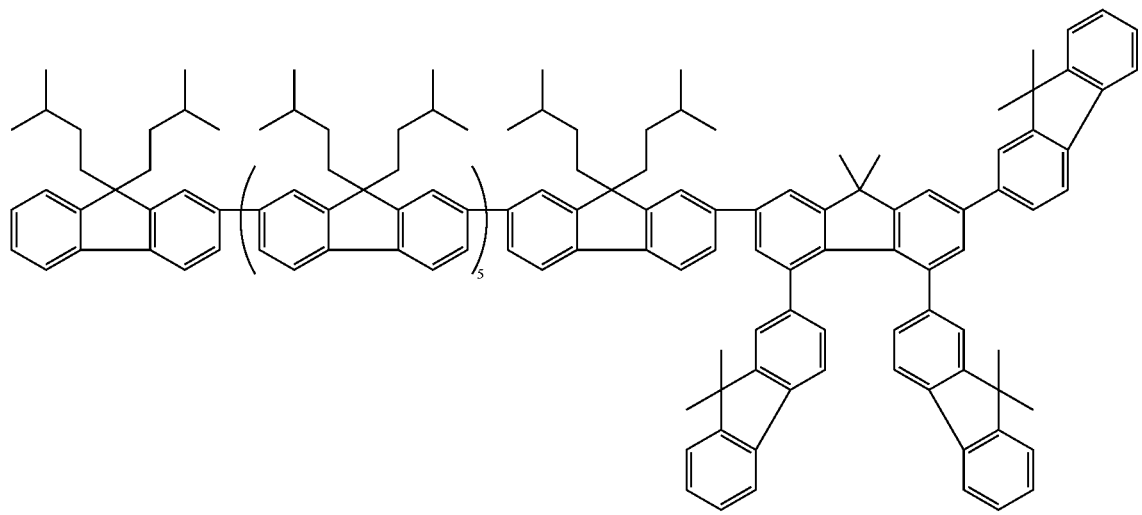

The fluorene compound of the present invention is preferably synthesized from a reaction precursor of the present invention represented by the following general formula (VI) or (VII).

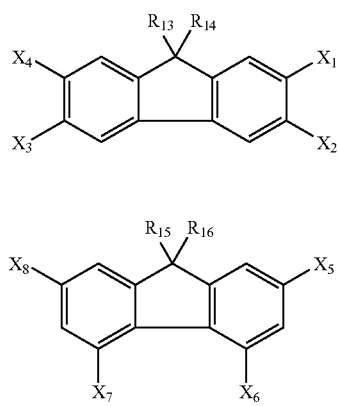

In the formulae (VI) and (VII), $R_{13}$ to $R_{16}$ each represent an alkyl group, a fluorinated alkyl group, a substituted or unsubstituted aralkyl group, or a substituted or unsubstituted aryl group.

Specific examples of an alkyl group, a fluorinated alkyl group, an aralkyl group, and an aryl group, and a substituent which an aralkyl group and an aryl group may have, represented by $R_{13}$ to $R_{16}$, are similar to $R_1$ to $R_4$ in the formulae (I) and (II).

In the formulae (VI) and (VII), $X_1$ to $X_8$ each represent bromine or iodine.

Although the synthesis method of the reaction precursors represented by the general formulae (VI) and (VII) are not particularly limited, for example, the reaction precursors can be obtained in good yield according to the following reaction synthesis route.

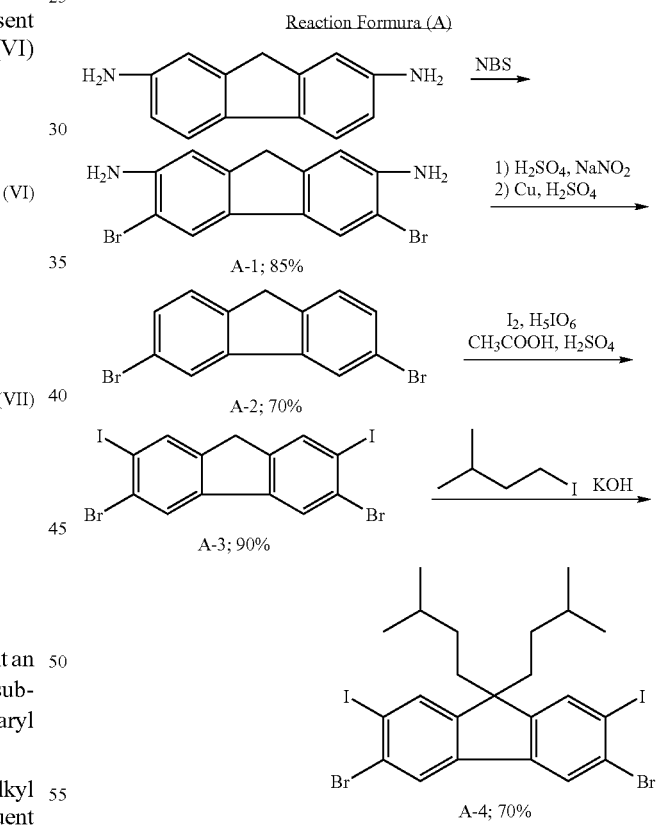

The reaction formula (A) shows an example of a method of synthesizing a 2,7-diiodo-3,6-dibromofluorene derivative in which both two hydrogen atoms at a 9-position of a fluorene unit are substituted by an isopentyl group. According to the reaction formula (A), a precursor represented by the general formula (VI) for synthesizing the fluorene compound represented by the general formulae (I) and (II) is obtained. The reaction formula (A) is a reaction route including a selective bromination of diaminofluorene to 3-position and 6-position, a deamination due to a Sandmeyer reaction, and a selective iodination to 2-position and 7-position.

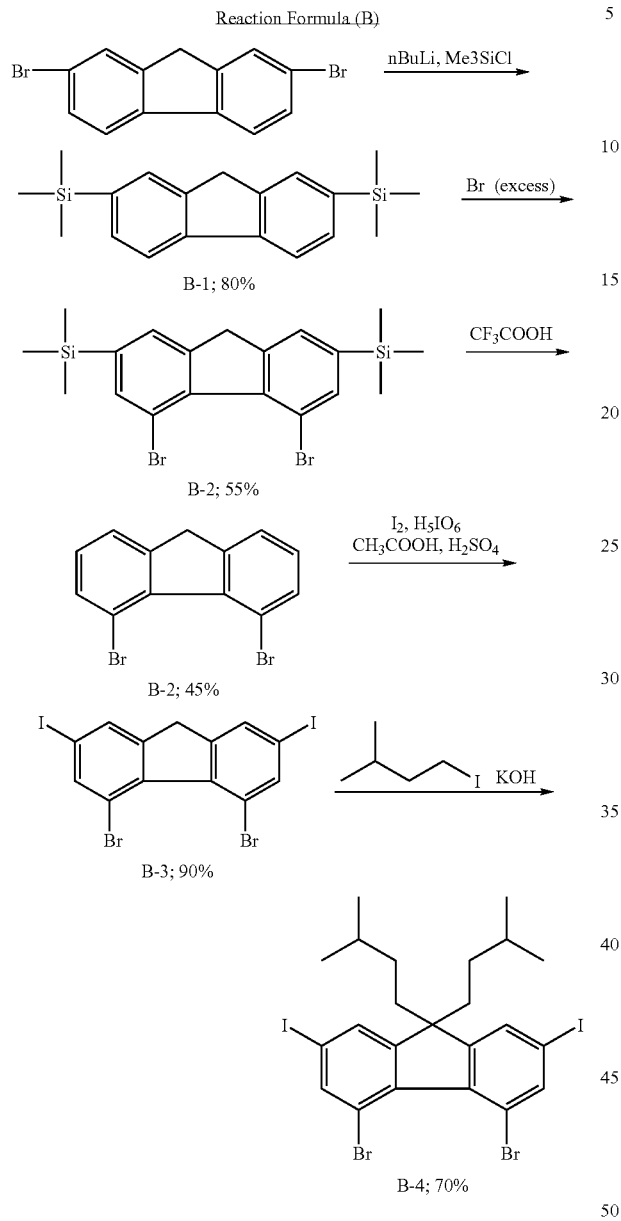

The reaction formula (B) shows an example of a method of synthesizing a 2,7-diiodo-4,5-dibromofluorene derivative in which both two hydrogen atoms at a 9-position of a fluorene unit are substituted by an isopentyl group. According to the reaction formula (B), a precursor represented by the general formula (VII) for synthesizing the fluorene compound represented by the general formulae (II) and (VI) is obtained. The reaction formula (B) is a reaction route including a selective bromination of 2,7-(trimethylsilyl)fluorene to 4-position and 5-position, a desilylation with trifluoroacetic acid, and a selective iodization to 2-position and 7-position.

The specific configuration of the reaction precursor of the present invention is as represented by the following formulae. It should be noted that the present invention is not limited thereto.

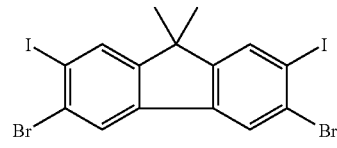
PRECURSOR 1

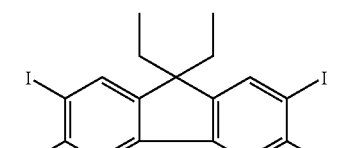
PRECURSOR 2

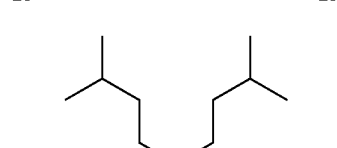
PRECURSOR 3

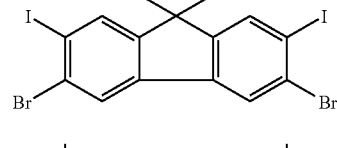
PRECURSOR 4

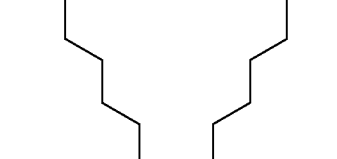
PRECURSOR 5

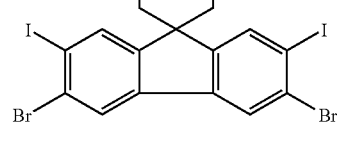
PRECURSOR 6

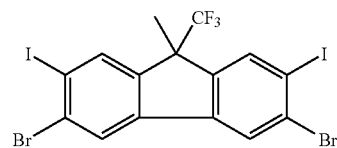
PRECURSOR 7

PRECURSOR 8

-continued

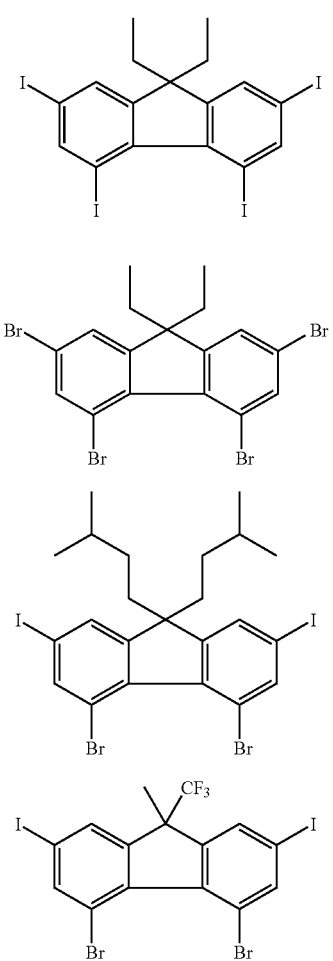

PRECURSOR 9

PRECURSOR 10

PRECURSOR 11

PRECURSOR 12

The fluorene compound of the present invention can be synthesized by a generally known method, using the reaction precursor of the present invention. For example, the fluorene compound of the present invention can be synthesized by a Suzuki Coupling method (for example, Chem. Rev., 95, 2457, 1995) using a palladium catalyst, a Yamamoto method (for example, Bull. Chem. Soc. Jpn. 51, 2091, 1978) using a nickel catalyst.

Next, an organic light emitting device of the present invention will be described in detail.

The organic light emitting device of the present invention includes an anode, a cathode, and a layer formed of an organic compound, the layer being interposed between the anode and the cathode.

Hereinafter, an organic light emitting device of the present invention will be described in detail with reference to the drawings.

In FIGS. 1A to 4, reference numerals 1a, 1b, 1c, and 34 each denote organic light emitting device, 10 denotes a metal electrode (cathode), 11 denotes an electron injecting/transporting layer, 12 denotes a light emitting layer, 13 denotes a hole injecting/transporting layer, 14 denotes a transparent electrode (anode), 15 denotes a transparent substrate, 16 denotes an interlayer layer, 17 denotes a multifunctional light emitting layer, 20 and 40 each denote display apparatus, 21 denotes a scanning signal driver, 22 denotes an information signal driver, 23 denotes a current supply source, 24 and 30 each denote pixel circuit, 31 denotes a first thin film transistor (TFT), 32 denotes a capacitor ($C_{add}$), 33 denotes a second thin film transistor (TFT), 41 denotes a substrate, 42 denotes a moisture-proof layer, 43 denotes a gate electrode, 44 denotes a gate insulating film, 45 denotes a semiconductor film, 46 denotes a drain electrode, 47 denotes a source electrode, 48 denotes a TFT element, 49 denotes an insulating film, 50 denotes a contact hole (through-hole), 51 denotes an anode, 52 denotes an organic layer, 53 denotes a cathode, 54 denotes a first protective layer, and 55 denotes a second protective layer.

FIGS. 1A to 10 are cross-sectional views each showing an example of an embodiment of an organic light emitting device of the present invention.

FIG. 1A is a cross-sectional view showing a first embodiment of the organic light emitting device of the present invention. In an organic light emitting device 1a in FIG. 1A, a laminated body in which the metal electrode 10, the electron injecting/transporting layer 11, the light emitting layer 12, the hole injecting/transporting layer 13, and the transparent electrode 14 are formed in this order from above is provided on the transparent substrate 15.

The organic light emitting device 1a in FIG. 1A exhibits an electrical rectifying property. When an electric field is applied to the organic light emitting device 1a so that the metal electrode 10 functions as a cathode and the transparent electrode 14 functions as an anode, electrons are injected from the metal electrode 10 to the light emitting layer 12 and holes are injected to the light emitting layer 12 from the transparent electrode 14. The injected holes and electrons are recombined in the light emitting layer 12 to generate excitons to emit light. At this time, the hole injecting/transporting layer 13 also functions as a layer blocking electrons. This enhances the recombination efficiency of the holes and electrons at an interface between the light emitting layer 12 and the hole injecting/transporting layer 13, so an light emitting efficiency is enhanced.

Figure 1B:
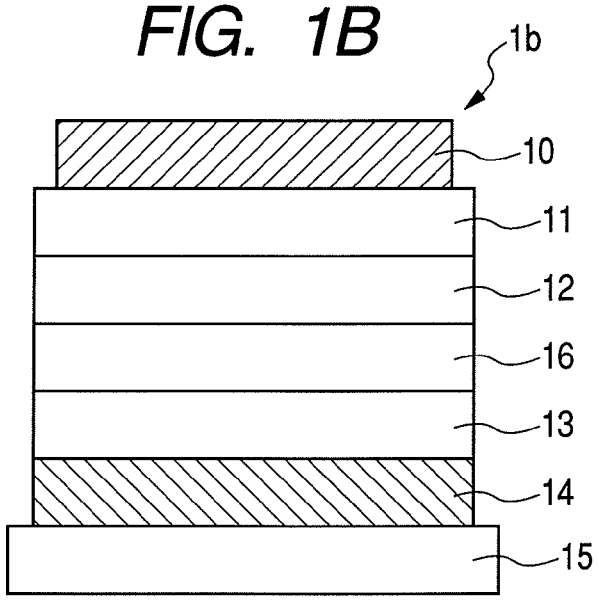

FIG. 1B is a cross-sectional view showing a second embodiment of an organic light emitting device of the present invention. An organic light emitting device 1b in FIG. 1B corresponds to the organic light emitting device in FIG. 1A in which the interlayer layer 16 is provided between the light emitting layer 12 and the hole injecting/transporting layer 13. By providing the interlayer layer 16, the electrons moving from the light emitting layer 12 to the hole injecting/transporting layer 16 can be blocked effectively. Further, the interlayer layer 16 also has an effect of blocking diffusion ions seeping from the hole injecting/transporting layer 13. Therefore, the light emitting efficiency of a device is enhanced, and the durability is also enhanced.

Figure 1C:
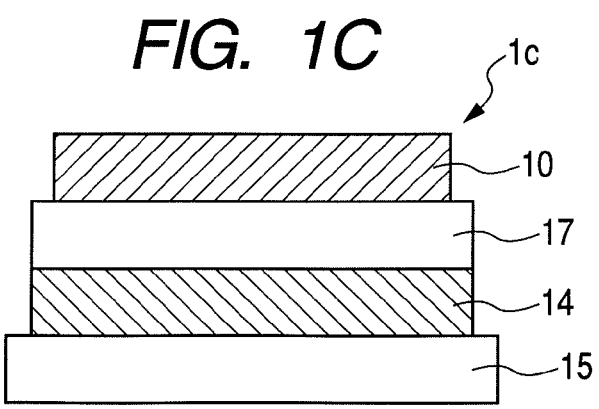

FIG. 1C is a cross-sectional view showing a third embodiment of the present invention. In an organic light emitting device 1c in FIG. 1C, a laminated body in which a metal electrode 10, a multifunctional light emitting layer 17, and a transparent electrode 14 are laminated from above, is formed on a transparent substrate 15. As illustrated in FIG. 1C, in the organic light emitting device of the present invention, only one organic layer may be formed. In the organic light emitting device 1c in FIG. 1C, the multifunctional light emitting layer 17 refers to a light emitting layer having both a charge injecting function and a charge transporting function. Further, the multifunctional light emitting layer 17 is formed of a light emitting material having both a charge injecting function and a charge transporting function, or a mixture of a plurality of materials having any of a charge injecting function, a charge transporting function, and a light emitting function. In the latter case, the multifunctional light emitting layer 17 is formed of, for example, a mixture of the fluorene compound of the present invention and another organic compound.

It should be noted that the device structures according to FIGS. 1A to 10 are each merely very basic one, and the structure of the organic light emitting device of the present invention is not limited to those. For example, an insulating layer may be provided onto an interface between an electrode and an organic layer, an adhesive layer or an interference layer may be provided thereonto, and a hole injecting/transporting layer may be formed of two layers having different ionization potentials or energy band gaps. Thus, the organic light emitting device can be formed of various layers.

In the organic light emitting device of the present invention, at least one kind of the fluorene compound of the present invention is included in a layer formed of an organic compound. Here, a layer formed of an organic compound specifically refers to the electron injecting/transporting layer 11, the light emitting layer 12, the hole injecting/transporting layer 13, and the multifunctional organic layer 17 illustrated in FIG. 1. Preferably, the layer formed of an organic compound is the light emitting layer 12.

Next, the member forming the organic light emitting device of the present invention will be described in detail.

The organic light emitting device of the present invention contains the fluorene compound of the present invention as a constituent member, as described above. Here, the fluorene compound of the present invention has the following features.

(i) Molecules themselves exhibit a high amorphous property, and in the case where the fluorene compound is formed into a thin film and stored for a long period of time and while being heated, the thin film is not whitened (crystallized, coagulated, etc.).

(ii) The fluorene compound exhibits an excellent solubility with respect to various kinds of solvents, and has a high adaptability to a coating method (Wet process).

(iii) Since an excited triplet energy level ($T_1$) is higher (2.5 eV or more) than $T_1$ of a green phosphorescence emitting material, the fluorene compound can be used as a host material of a green phosphorescence material.

(iv) A glass transition temperature is high.

Note that in (iii), $T_1$ is an energy level calculated from a light emitting end on a short wavelength side of a phosphorescence spectrum. Further, $T_1$ can be calculated according to a method described in Journal of the American Chemical Society, 125, 15310 (2003).

Therefore, the fluorene compound of the present invention can be used preferably as a host of a light emitting layer. Here, when the fluorene compound of the present invention is used as a host, the fluorene compound of the present invention is doped with a light emitting material that is a guest. In the organic light emitting device of the present invention, a mixture of the fluorene compound of the present invention and a charge transporting organic compound may be used as a host. Examples of the charge transporting organic compound include known electron or hole transporting organic compounds described later. Further, the light emitting material that is a guest may be fluorescent or phosphorescent.

Examples of the fluorescent light emitting material include benzooxazole and a derivative thereof, benzoimidazole and a derivative thereof, benzothiazole and a derivative thereof, styrylbenzene and a derivative thereof, polyphenyl and a derivative thereof, diphenylbutadiene and a derivative thereof, tetraphenylbutadiene and a derivative thereof, naphthalimide and a derivative thereof, coumarin and a derivative thereof, a polycondensed aromatic compound, perinone and a derivative thereof, oxadiazole and a derivative thereof, oxadine and a derivative thereof, aldazine and a derivative thereof, pyraridine and a derivative thereof, cyclopendadiene and a derivative thereof, bisstyryl anthracene and a derivative thereof, quinacridon and a derivative thereof, pyrrolopyridine and a derivative thereof, thiadiazoropyridine and a derivative thereof, cyclopentadiene and a derivative thereof, styrylamine and a derivative thereof, diketopyrrolopyrrole and a derivative thereof, an aromatic dimethylidene compound, 8-quinolinol and a metal complex that is a derivative thereof, pyrromethene and a metal complex that is a derivative thereof, a rare earth complex, various kinds of metal complexes such as a transition metal complex, polymer compounds such as polythiophene, polyphenylene, and polyphenylenevinylene, and an organic silane and a derivative thereof. Preferably, a polycondensed aromatic compound, a quinacridon derivative, diketopyrrolopyrole derivative, a metal complex of a pyrromethene derivative, a rare earth complex, and a transition metal complex are used, and more preferably, polycondensed aromatic compound and a transition metal complex are used.

On the other hand, considering an efficiency (external quantum efficiency of an organic light emitting device), it is preferred to use a phosphorescent light emitting material.

The phosphorescent light emitting material is preferably a transition metal complex. In the case of using a transition metal complex as a phosphorescent light emitting material, although center metal of a complex is not particularly limited, iridium, platinum, rhenium, or ruthenium is preferably used. Iridium or platinum is more preferably used, and iridium is particularly preferred. Here, as a transition metal complex, specifically, an ortho-metallized complex disclosed by the following listed documents can be used.

1. Written by Akio Yamamoto, "Organic metal, base and application" p. 150 and 232, Shokabo Publishing Co., Ltd. (1982)

2. Written by H. Yersin, "Photochemistry and Photophysics of Coordination Compound", p. 71 to 77, and 135 to 146, Springer-Verlag (1987)

3. Japan Society for the Promotion of Science, "Organic Materials for Telecommunication Technology, $142^{th}$ commission" C meeting (Organic electronics), $9^{th}$ research meeting document, items 25 to 32 (2005)

In addition to the above, suitably used phosphorescent light-emitting materials are disclosed in Patent Documents such as U.S. Pat. Nos. 6,303,231 and 6,097,147, International Publication Nos. WO00/57676, WO00/70655, WO01/08230, WO01/39234, WO01/41512, WO02/02714 and WO02/15645, Japanese Patent Application Laid-Open No. 2001-247859, Japanese Patent Application Nos. 2000-33561, 2001-189539, 2001-248165, 2001-33684, 2001-239281, and 2001-219909, European Patent No. 1211257A Japanese Patent Application Laid-Open Nos. 2002-226495, 2002-234894, 2001-247859, 2001-298470, 2002-173674, 2002-203678, and 2002-203679.

In addition, suitably used phosphorescent light-emitting materials are disclosed in Non-patent Documents such as Nature, Vol. 395, p. 151 (1998), Applied Physics Letters, Vol. 75, p 4 (1999), Polymer Preprints, Vol. 41, p. 770 (2000), Journal of American Chemical Society, Vol. 123, p. 4304 (2001), and Applied Physics Letters, Vol. 79, p 2082 (1999).

The organic light emitting device 1a in FIG. 1A contains the fluorene compound of the present invention mainly as a constituent material of the light emitting layer 12. In the embodiment illustrated in FIG. 1A, in the case where the fluorene compound of the present invention is used as a constituent material of the light emitting layer 12, the fluorene compound of the present invention can be used as a host in combination with the above fluorescent or phosphorescent material that is a guest. Further, the host of the light emitting layer 12 may be a combination of the fluorene compound of the present invention and an organic compound that is a third material.

Here, examples of the organic compound that is a third material include known charge transporting materials (a hole transporting material and an electron transporting material). Specific examples of the charge transporting material will be described later.

The content of the organic compound that is a third material is preferably 1% by weight or more to 50% by weight or less, and more preferably 5% by weight or more to 30% by weight or less with respect to the total weight of the material constituting the light emitting layer. When the content is smaller than 1% by weight, the effect of the added organic compound that is a third material (i.e., desired hole transportability in the case of the hole transporting compound and desired electron transportability in the case of an electron transporting compound) cannot be obtained. On the other hand, when the content is larger than 50% by weight, the characteristics of the added organic compound that is a third material become excessive, and there is a possibility that the film stability, a high efficiency, high durability, and the like of the fluorene compound of the present invention may not be exhibited sufficiently.

The material constituting the interlayer layer 16 illustrated in FIG. 1B is not particularly limited as long as it has a wide gap and charge transportability, and is excellent in film stability (electrical, chemical, or thermal stability). Specific examples of the material include polyvinyl carbazole (PVK).

The material used for the hole injecting/transporting layer 13 is not particularly limited, but the material can be selected from the hole transporting material or charge transporting material that can be used as the material constituting the organic light emitting device of the present invention. Specifically, triarylamine derivatives, phenylene diamine derivatives, triazole derivatives, oxadiazole derivatives, imidazole derivatives, pyrazoline derivatives, pyrazolone derivatives, oxazole derivatives, fluorenone derivatives, hydrazone derivatives, stilbene derivatives, phthalocyanine derivatives, porphyrin derivatives, poly(vinylcarbazole), poly(silylene), poly(thiophene), and the like are mentioned. Those compounds may be contained, as an organic compound which is the above third material and is a host of the light emitting layer, in a light emitting layer.

The material used for the electron injecting/transporting layer 11 is not particularly limited, but the material can be selected from the electron transporting material or the charge transporting material that can be used as the material constituting the organic light emitting device of the present invention. Specific examples thereof include organic compounds such as oxadiazole derivatives, oxazole derivatives, thiazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives, and an organic metal complex such as a quinolinol aluminum complex. Metal elements such as lithium, sodium, potassium, cesium, calcium, magnesium, aluminum, indium, silver, lead, tin, and chromium, a metal fluoride such as lithium fluoride, or a metal carbonate such as cesium carbonate can also be used. The above metal element, metal fluoride, and metal carbonate may be used alone, or in combination with an organic compound that is an electron transporting material or a charge transporting material. Further, these compounds may be contained in the light emitting layer in the form of the above organic compound that is a third material, which is one host of the light emitting layer.

A desirable material which forms the anode has as large a work function as possible. Examples of available materials include: metal elements such as gold, silver, platinum, nickel, palladium, cobalt, selenium, and vanadium; alloys combining those metal elements; and metal oxides such as tin oxide, zinc oxide, indium tin oxide (ITO), and indium zinc oxide. Further, conductive polymers such as polyaniline, polypyrrole, polythiophene, and polyphenylene sulfide may also be used. Each of those electrode substances may be used singly. Alternatively, two or more of them may also be used in combination. Further, the anode may be formed of a single layer or multiple layers.

On the other hand, a desirable cathode material has as small a work function as possible. Examples of available materials include: metal elements such as lithium, sodium, potassium, cesium, calcium, magnesium, aluminum, indium, silver, lead, tin, and chromium; alloys formed of multiple metal elements in combination; and salts thereof. Further, metal oxides such as indium tin oxide (ITO) may also be used. Further, the cathode may be formed of a single layer or multiple layers.

Substrates which may be used in the organic light emitting device of the present invention include: opaque substrates such as metallic substrates and ceramics substrates; and transparent substrates such as glass, quartz, and plastic sheet substrates, but are not particularly limited to these materials. In addition, a color filter film, a fluorescent color converting film, a dielectric reflection film, or the like may be used in the substrate to control emitted light.

It is preferred that the organic light emitting device of the present invention be finally covered with a protective layer. As a material for the protective layer, those which have a function of preventing a substance that promotes the degradation in a device, such as moisture and oxygen, from entering the device may be used. Specific examples thereof include: metal elements such as In, Sn, Pb, Au, Cu, Ag, Al, Ti, and Ni; metal oxides such as MgO, SiO, $SiO_2$, $Al_2O_3$, GeO, NiO, CaO, BaO, $Fe_2O_3$, $Y_2O_3$, and $TiO_2$; metal fluorides such as $MgF_2$, LiF, $AlF_3$, and $CaF_2$; nitrides such as $SiN_x$ and $SiO_xN_y$; polyethylene; polypropylene; polymethylmethacrylate; polyimide; polyurea; polytetrafluoroethylene; polychlorotrifluoroethylene; polydichlorodifluoroethylene; a copolymer of chlorotrifluoroethylene and dichlorodifluoroethylene; a copolymer obtained by copolymerizing a monomer mixture containing tetrafluoroethylene and at least one kind of comonomer; a fluorene-containing copolymer having a cyclic structure in a copolymer main chain; a water-absorbing material with a water-absorbing ratio of 1% or more; and a moistureproof material with a water-absorbing ratio of 0.1% or less.

In the organic light emitting device of the present invention, as a layer containing the fluorene compound of the present invention, a thin film is generally formed by vacuum vapor deposition or coating of a fluorene compound dissolved in an appropriate solvent. Specific examples of the method of forming a thin film by coating include a spin coating, a slit coater method, a printing, an ink-jet method, and a spray method. Among the fluorene compounds of the present invention, a compound having a molecular weight exceeding 2000 tends to have a high sublimation temperature. Therefore, preferably, in such a case, a thin film is formed by coating.

A specific method of forming a layer containing the fluorene compound of the present invention will be described by using the organic light emitting device in FIG. 1A as a specific example. In the case of forming a light emitting layer containing the fluorene compound of the present invention by coating (Wet process), the light emitting layer is formed specifically by the following method. First, as the hole injecting/transporting layer 13, the hole injecting/transporting layer 13 is formed on an ITO substrate by using an aqueous solution containing water-soluble polyethylenedioxythiophene/polystyreneslufonate (PDOT/PSS). Next, on the hole injecting/transporting layer 13, a light emitting layer is formed using ink for coating composed of the fluorene compound of the present invention, a fluorescent or phosphorescent light emitting material, an organic compound that is a third material in some cases, and an organic solvent.

In the case of forming a layer containing the fluorene compound of the present invention by coating, a film can also be formed in combination with an appropriate binder resin.

The above binder resins can be selected from a wide variety of binder resins. Examples thereof include, but are not limited to, a polyvinylcarbazole resin, a polycarbonate resin, a polyester resin, a polyallylate resin, a polystyrene resin, an acrylic resin, a methacrylic resin, a butyral resin, a polyvinyl acetal resin, a diallyl phthalate resin, a phenol resin, an epoxy resin, a silicone resin, a polysulfone resin, and a urea resin. Further, those binder resins may be a homopolymer or may be a copolymer. Each of those resins may also be used singly or, two or more of them may be used in combination.

There is no particular limit to the method of forming a protective layer covering the organic light emitting device, and for example, a vacuum vapor deposition, a sputtering, a reactive sputtering, a molecular beam epitaxy (MBE) method, a cluster ion beam method, an ion plating, a plasma polymerization (high-frequency excitation ion plating), a plasma CVD, a laser CVD, a thermal CVD, a gas source CVD, a coating, a printing, and a transfer method can be applied.

The thickness of the layer containing the fluorene compound of the present invention is smaller than 10 μm, preferably 0.5 μm or less, and more preferably 0.01 μm or more to 0.5 μm or less.

Next, an ink composition of the present invention will be described.

The ink composition of the present invention contains at least one kind of the fluorene compound of the present invention. When the ink composition of the present invention is used, the layer constituting the organic light emitting device, in particular, the light emitting layer can be produced by a coating, and hence, a device with a large area can be produced easily at a low cost. In particular, the fluorene compound having a molecular weight of 2000 or more tends to have a high sublimation temperature, so the fluorene compound is preferably used as an ink composition in the form of being dissolved in a solvent.

Here, examples of the solvent include toluene, xylene, mesitylene, dioxane, tetralin, methylnaphthalene, tetrahydrofuran, and diglyme.

In the ink composition of the present invention, the amount of a solid component of the fluorene compound of the present invention and another organic compound is preferably 0.05% by weight or more to 20% by weight or less, and more preferably 0.1% by weight or more to 10% by weight or less with respect to the total weight of the ink composition. When the amount is smaller than 0.05% by weight, the concentration of a mixture of the fluorene compound and another organic compound that is a solid component in ink is extremely small, so there is a possibility that stability of a produced film may be impaired. When the amount is larger than 10% by weight, there is a possibility that the solid component in ink is precipitated without being dissolved completely, and a produced film may be enlarged in thickness.

In the organic light emitting device of the present invention, light extraction efficiency, a color purity, and the like can be enhanced due to various known means. For example, by forming the shape of a substrate surface (for example, form a fine uneven pattern), controlling the refractive indices of a substrate/an ITO layer/an organic layer, controlling the thicknesses of a substrate/an ITO layer/an organic layer, and the like, the light extraction efficiency and the external quantum efficiency can be enhanced. It is also possible to enhance a color purity by a method of reducing an excessive wavelength component using a micro-cavity structure (micro resonator structure), obtaining a desired color with a color filter, and the like.

The organic light emitting device of the present invention may be a so-called top emission system in which light is extracted from an anode side for the purpose of enhancing an opening ratio, or a cavity structure of adjusting the color purity by optical buffer.

The organic light emitting device of the present invention is applicable to a product which requires energy conservation and high luminance. As application examples, an image display apparatus, a light source of a printer, an illumination apparatus, a backlight of a liquid crystal display apparatus, and the like are conceivable.

An example of the image display apparatus includes an energy-efficient and light-weight flat panel display with high visibility.

Further, as the light source of a printer, for example, a laser light source portion of a laser beam printer that has been currently used widely can be replaced by the organic light emitting device of the present invention. An example of a replacement method includes a method of placing an organic light emitting device that can be addressed independently on an array. Even if the laser light source portion is replaced by the organic light emitting device of the present invention, there is no particular difference in the formation of an image from a conventional example by conducting desired light exposure to a photosensitive drum. The volume of an apparatus can be reduced remarkably by using the organic light emitting device of the present invention.

Regarding the illumination apparatus and the backlight, the effect of saving energy can be expected by using the organic light emitting device of the present invention.

Next, the display apparatus of the present invention will be described. The display apparatus of the present invention uses the organic light emitting device of the present invention. Hereinafter, the display apparatus of the present invention will be described in detail by exemplifying an active matrix system with reference to the drawings.

Figure 2:
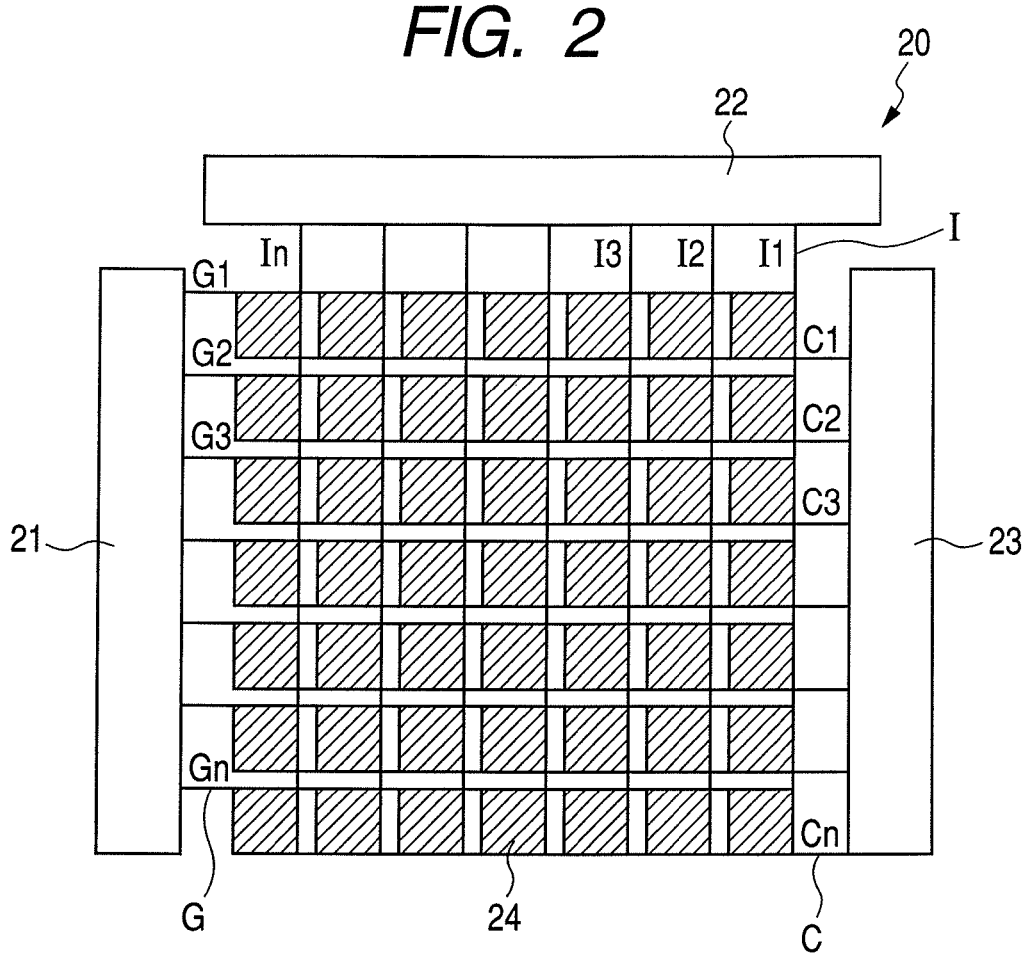
FIG. 2 is a view schematically illustrating an exemplary constitution of an image display apparatus having an organic light emitting device and a driving unit of the present invention.

FIG. 2 is a view schematically illustrating a configuration of a display apparatus according to an embodiment of the present invention including the organic light emitting device of the present invention and a driving unit. In a display apparatus 20 illustrated in FIG. 2, a scanning signal driver 21, an information signal driver 22, and a current supply source 23 are placed, which are each connected to gate selection lines G, information signal lines I, and current supply lines C. A pixel circuit 24 is placed at a crossing point of the gate selection line G and the information signal line I. The scanning signal driver 21 successively selects gate selection lines G1, G2, G3, ... or Gn, and in synchronization therewith, an image signal is applied from the information signal driver 22 to the pixel circuit 24 through any of the information signal lines I1, I2, I3, ... or In.

Figure 3:
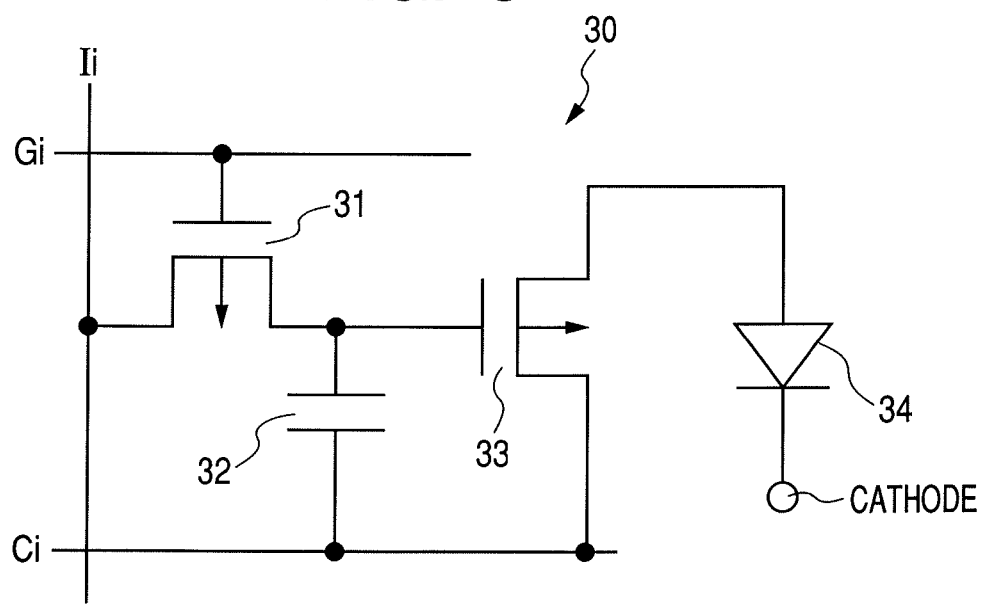
FIG. 3 is a circuit diagram showing a circuit constituting one pixel placed in the display apparatus in FIG. 2.

Next, the behavior of the pixels will be described. FIG. 3 is a circuit diagram illustrating a circuit constituting one pixel placed in the image display apparatus in FIG. 2. In a pixel circuit 30 in FIG. 3, when a selection signal is applied to the gate selection line $G_i$, a first thin film transistor (TFT1) 31 is turned on, and an image signal $I_i$ is supplied to a capacitor ($C_{add}$) 32, whereby a gate voltage of a second thin film transistor (TFT2) 33 is determined. A current is supplied to an organic light emitting device 34 from a current supply line $C_i$ in accordance with a gate voltage of the second thin film transistor (TFT2) 33. The gate potential of the second thin film transistor (TFT2) 33 is held at the capacitor ($C_{add}$) 32 until the first thin film transistor (TFT1) 31 is scanned and selected next. Therefore, a current continues to flow through the organic light emitting device 34 until the subsequent scanning is conducted. This enables the organic light emitting device 34 to emit light at all times during one frame.

Figure 4:
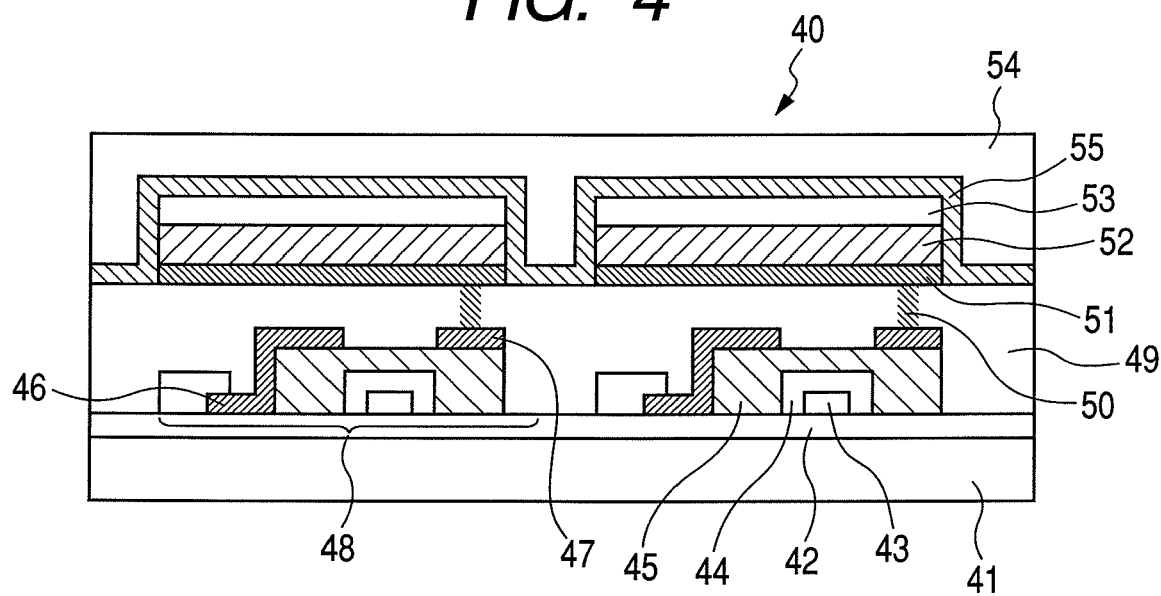
FIG. 4 is a schematic view illustrating an example of a cross-sectional configuration of a TFT substrate.

FIG. 4 is a schematic view illustrating an example of a cross-sectional configuration of a TFT substrate used in the display apparatus of the present invention. The detail of the configuration will be described by way of an example of the production process of a TFT substrate. When the display apparatus 40 in FIG. 4 is produced, a substrate 41 formed of glass or the like is coated with the moisture-proof film 42 for protecting a member (a TFT or an organic layer) formed in an upper portion. As a material constituting the moisture-proof film 42, silicon oxide, a composite of silicon oxide and silicon nitride, or the like is used. Next, metal such as Cr is formed into a film by sputtering and patterned to a predetermined circuit shape, whereby a gate electrode 43 is formed. Subsequently, silicon oxide or the like is formed into a film by a plasma CVD, a catalyst chemical vapor deposition (cat-CVD), or the like, and patterned to form a gate insulating film 44. Next, a silicon film is produced by plasma CVD (by annealing at a temperature of 290° C. or higher in some cases), and patterned in accordance with a circuit shape, whereby a semiconductor layer 45 is formed.

Further, a drain electrode 46 and a source electrode 47 are provided on the semiconductor film 45 to produce a TFT element 48, whereby a circuit as illustrated in FIG. 3 is formed. Next, an insulating film 49 is formed in an upper portion of the TFT element 48. Next, a contact hole (through-hole) 50 is formed so that an anode 51 for an organic light emitting device formed of metal comes into contact with a source electrode 47.

A multi-layer or signal-layer organic layer 52 and a cathode 53 are successively laminated on the anode 51, whereby a display apparatus 40 can be obtained. At this time, in order to prevent the degradation of the organic light emitting device, a first protective layer 54 and a second protective layer 55 may be provided. By driving the display apparatus using the fluorene compound of the present invention, a display of a satisfactory quality, which is stable for a display for a long period of time, can be conducted.

In the display apparatus of the present invention, there is no particular limit to a switching device, and any switching device can be easily applied to a single crystal silicon substrate, an MIM device, an a-Si type, and the like.

Hereinafter, although the present invention will be described more specifically by way of examples, the present invention is not limited thereto.

EXAMPLE 1

Synthesis of a Precursor 1

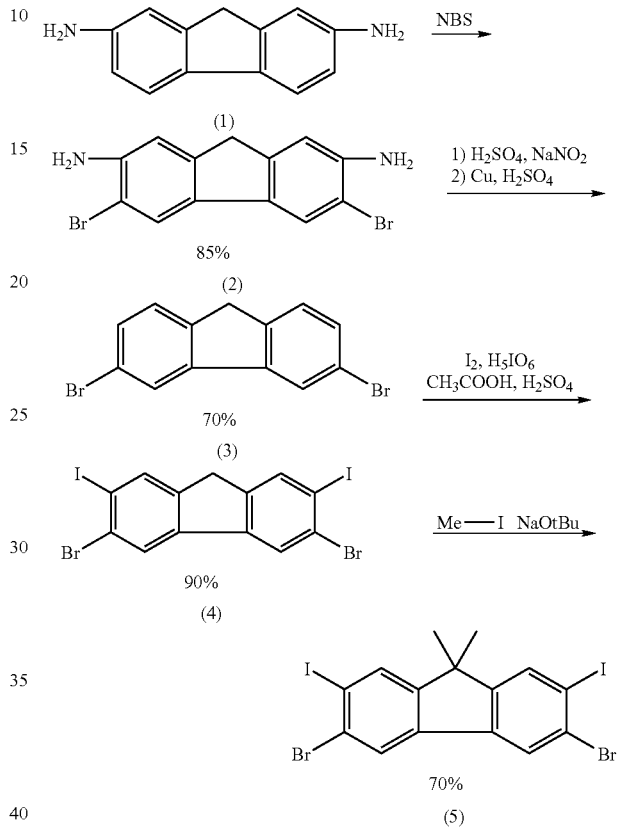

(1) 5 g (25.5 mmol) of a diaminofluorene compound that was a compound (1) and 200 ml of dimethyl sulfoxide were placed in a 500 ml three-necked flask, and the inside of the flask was set to be a nitrogen atmosphere. Next, while the reaction solution was kept at 25° C. or lower, 9.1 g (51 mmol) of NBS (N-bromosuccinimide) was placed over 30 minutes, and then, the reaction solution was stirred for 4 hours while it was kept at 25° C. or lower. After the completion of the reaction, the reaction solution was placed in ice water, and an organic layer was extracted with toluene. Next, the organic layer was washed with water, followed by drying, and thereafter, a solvent was evaporated under reduced pressure. Next, an obtained crude product was recrystallized with toluene, whereby 7.7 g (yield 85%) of an intermediate (2) was obtained.

(2) 7 g (19.8 mmol) of an intermediate (2) and 50 ml of ethanol were placed in a 300 ml three-necked flask. The reaction solution was cooled to −10° C. to 0° C., and 5 ml of concentrated sulfuric acid was dropped. After that, while the reaction solution was kept at −10° C. to 0° C., the reaction solution was stirred overnight. Next, the reaction solution was set to be 5° C. or lower, and thereafter, a sodium nitrite aqueous solution prepared from 4 g (59.3 mmol) of sodium nitrite was dropped onto the reaction solution. Then, the reaction solution was stirred for 2 hours while being kept at 5° C. or lower, whereby a diazonium salt solution was obtained from the reaction solution. On the other hand, in another reaction container, 2.8 g (44.1 mmol) of copper, 30 ml of ethanol, and 3 ml of concentrated sulfuric acid were mixed, and thereafter, the solution was refluxed. Next, the diazonium salt solution prepared previously was added slowly, and thereafter, the reaction solution was stirred for 3 hours while being refluxed. After the completion of the reaction, the reaction solution was placed in 100 ml of distilled water at room temperature. Next, an organic layer was extracted with chloroform, washed with water, and dried, and thereafter, a solvent was evaporated under reduced pressure. The obtained crude product was purified by silica gel column chromatography (developing solvent: hexane), whereby 4.5 g (yield 70%) of an intermediate (3) was obtained.

(3) The following reagents and solvents were placed in a 100 ml three-necked flask.

Intermediate (3): 3 g (9.3 mmol)

Iodine: 2.1 g (16.5 mmol as an iodine atom)

Orthoperiodic acid: 1.1 g (4.8 mmol)

Acetic acid: 100 ml

Water: 10 ml

Concentrated sulfuric acid: 3 ml

Next, the reaction solution was stirred at 80° C. for 5 hours while being set at a nitrogen atmosphere. After the completion of the reaction, the reaction solution was placed in 100 ml of water, and the generated precipitate was filtered. Next, the precipitate was purified by silica gel column chromatography (developing solvent: a mixed solvent of toluene and ethyl acetate), whereby 4.8 g (yield 90%) of an intermediate (4) was obtained.

(4) The following reagents and solvent were placed in a 100-ml three-necked flask.

Intermediate (4): 4.5 g (7.8 mmol)

Iodomethane: 4.4 g (31.3 mmol)

Sodium t-butoxide: 1.6 g (19.6 mmol)

Dimethylformamide: 40 ml

Next, the temperature of the reaction solution was set at room temperature to 50° C., and thereafter, the reaction solution was stirred for 8 hours. After the completion of the reaction, water was added to the reaction solution, and then, an organic layer was extracted with chloroform and dried. Next, the solution was concentrated under reduced pressure, methanol was placed in the concentrated solution, and the precipitated crystal was filtered. Thus, 3.3 g (yield 70% of 2,7-diiodo-3,6-dibromofluorene (compound (5)) that was a precursor 1 was obtained as a white crystal.

EXAMPLE 2

Synthesis of a Precursor 11

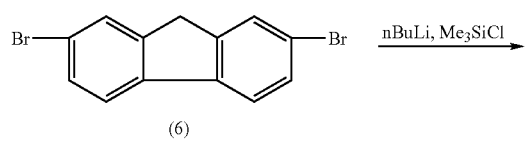

(6)

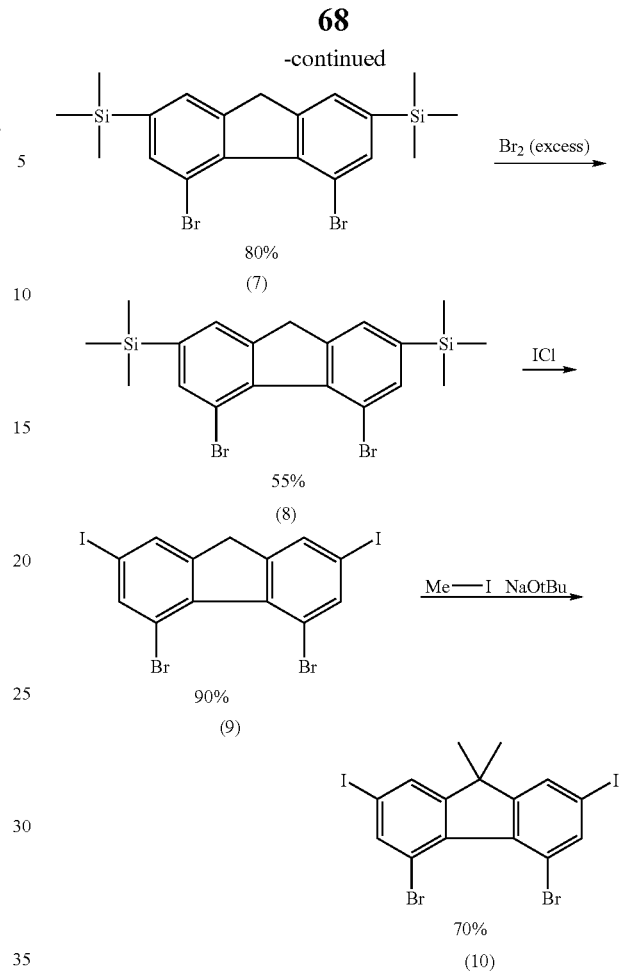

(1) 5 g (15.4 mmol) of bromofluorene that was a compound (6) and 250 ml of dehydrated THF were placed in a 500-ml three-necked flask, and the inside of the flask was set to a nitrogen atmosphere. Then, the reaction solution was cooled to −50° C., and then, 20 ml (32.4 mmol) of 1.6 mol/l solution of n-butyl lithium was dropped. Next, the reaction solution was stirred for 3 hours while being kept at −50° C., and thereafter, 3.7 g (33.9 mmol) of trimethylsilyl chloride was placed. Then, the reaction solution was slowly increased in temperature to room temperature. After the completion of the reaction, the solvent was evaporated under reduced pressure, and the obtained crude product was purified by silica gel column chromatography (developing solvent: hexane), whereby 3.8 g (yield 80%) of an intermediate (7) was obtained.

(2) After 3.5 g (11.3 mmol) of the intermediate (7) and 100 ml of carbon tetrachloride were placed in a 500 ml three-necked flask, 3.6 g (45 mmol, excess amount) of bromine was placed at room temperature. Next, the reaction solution was heated to 65° C. and stirred for 27 hours. After the completion of the reaction, the reaction solution was placed in 200 ml of water, and an organic layer was extracted. The organic layer was washed with water. Next, a crude product obtained by evaporating a solvent under reduced pressure was purified by silica gel column (developing solvent: hexane), whereby 2.9 g (yield 55%) of an intermediate (8) was obtained.

(3) 2.8 g (6 mmol) of an intermediate (8) and 100 ml of carbon tetrachloride were placed in a 500 ml three-necked flask, and the reaction solution was cooled to −70° C. Then, 3.9 g (24 mmol) of iodochloride was dropped slowly onto the reaction solution, and the reaction solution was stirred for 1 hour while being kept at −70° C. Next, the reaction solution was slowly increased in temperature to 0° C., and stirred for further 1 hour. Next, the reaction solution was increased in temperature to 40° C. and stirred for further 48 hours. After the completion of the reaction, the reaction mixed solution was placed little by little to 50 ml of cold water, and an organic layer was extracted with chloroform. Next, a solvent was evaporated under reduced pressure, and the obtained crude product was purified by silica gel column chromatography (developing solvent: hexane), whereby 3.1 g (yield 90%) of an intermediate (9) was obtained.

(4) 3 g (52.1 mmol) of an intermediate (9), 2.2 g (15.6 mmol) of methyl iodide, and 40 ml of dimethylsulfoxide were placed in a 100 ml three-necked flask, and the inside of the flask was set to be a nitrogen atmosphere. Next, the reaction solution was cooled to −60 to −50° C., and 1.1 g (13 mmol) of sodium t-butoxide was added. After that, the resultant reaction solution was returned to room temperature and stirred overnight. After the completion of the reaction, the reaction solution was placed in 100 ml of water, and an organic layer was extracted with toluene. Next, the solvent was evaporated under reduced pressure, and the obtained crude product was purified by silica gel column chromatography (developing solvent: hexane). Thus, 2.2 g (yield 70%) of 2,7-diiodo-4,5-dibromofluorene (compound (10)) that was a precursor 11 was obtained as a white crystal.

EXAMPLE 3

Synthesis of an Exemplified Compound No. 6

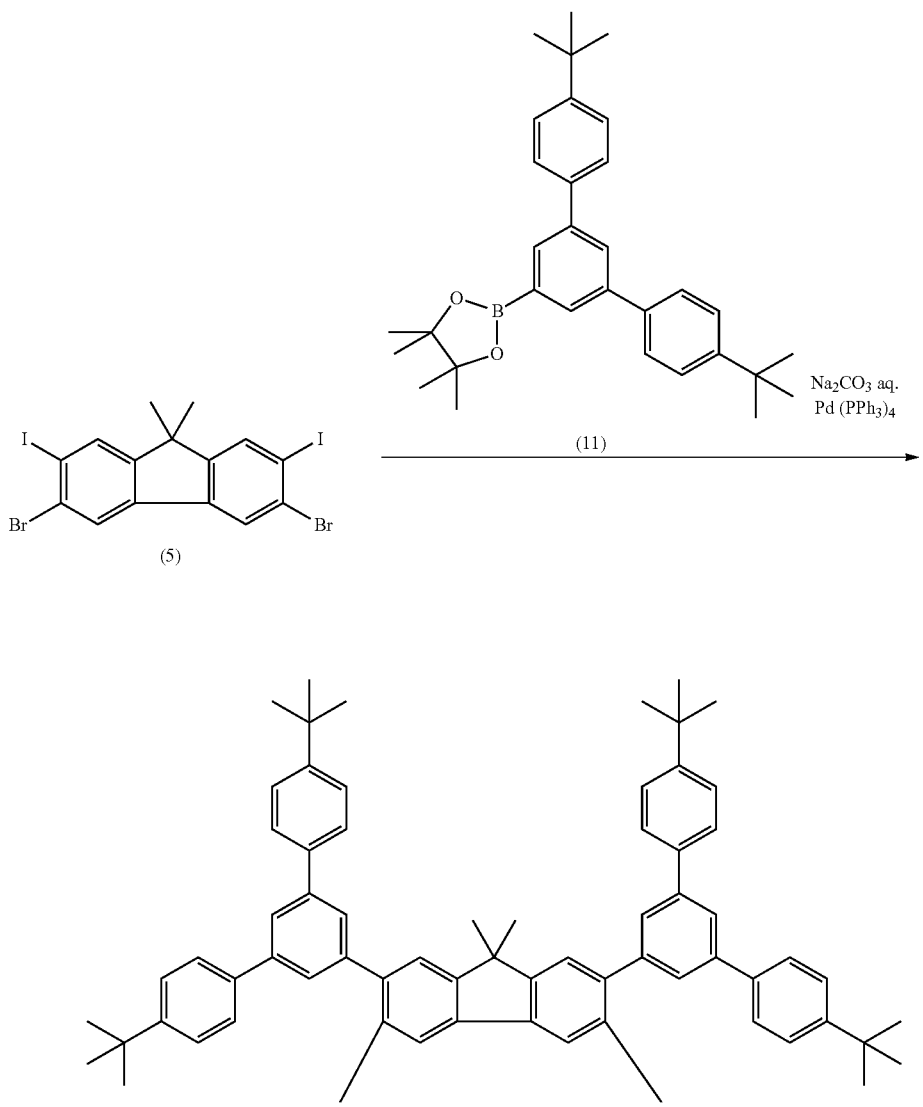

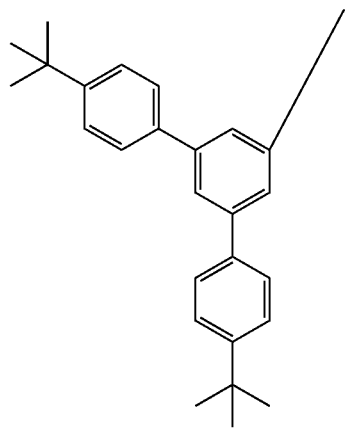

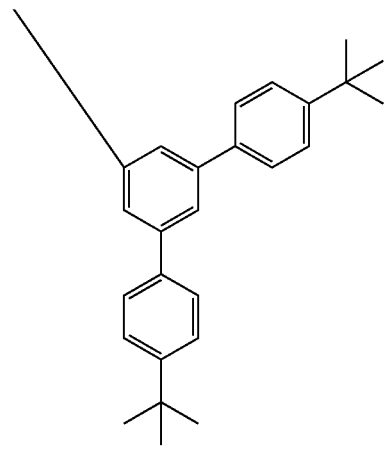

(12)

The following reagents and solvents were placed in a 200 ml three-necked flask.

2,7-diiodo-3,6-dibromofluorene (precursor 1): 0.5 g (0.83 mmol)

Pinacolborane compound (compound (11)): 1.7 g (3.7 mmol)

Toluene: 80 ml

Ethanol: 20 ml

Next, the inside of the flask was set to be a nitrogen atmosphere, and 20 ml of a saturated sodium carbonate solution was placed, and then, 0.19 g (0.17 mmol) of tetrakis(triphenylphosphine)palladium(0) was added to the reaction solution, while the reaction solution was stirred at room temperature. Next, the reaction solution was stirred for further 30 minutes at room temperature, and stirred for 18 hours while being refluxed. After the completion of the reaction, an organic layer was extracted with chloroform, and a solvent was evaporated under reduced pressure. Next, the obtained crude product was purified by silica gel column chromatography (developing solvent: a mixed solvent of hexane and chloroform), whereby 0.45 g (yield 35%) of an exemplified compound No. 6 that was a compound (12) was obtained as a white solid.

EXAMPLE 4

Synthesis of an Exemplified Compound No. 17

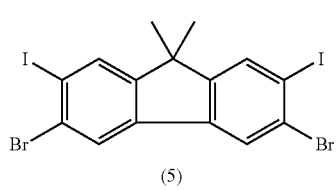

(5)

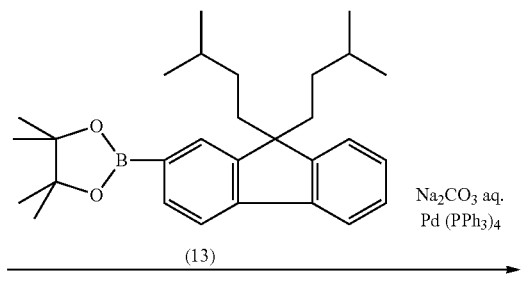

(13)

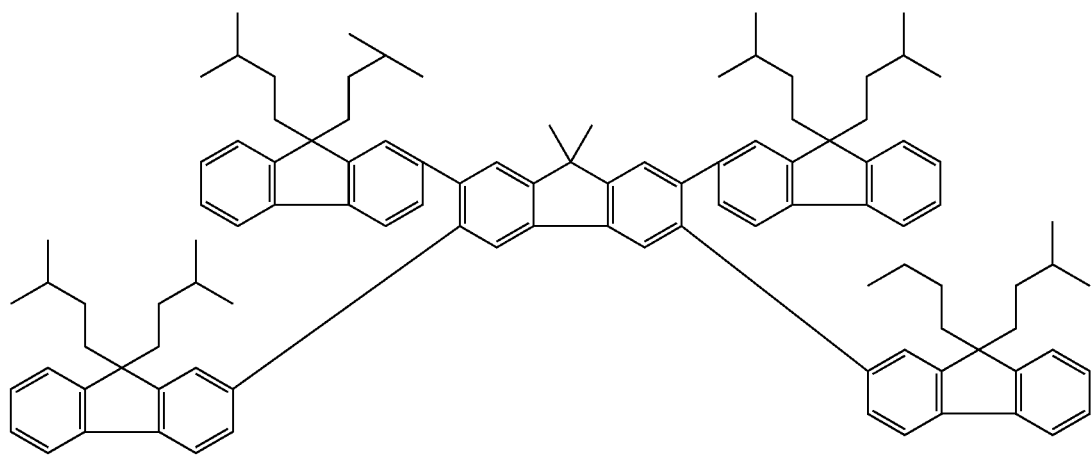
(14)
0.29 g (yield 25%) of an exemplified compound No. 17 that was a compound (14) was obtained as a white solid by the same reaction method as that of Example 3, except that a pinacolborane compound that was a compound (13) was used in place of the compound (11).

EXAMPLE 5
Synthesis of an exemplified compound No. 24
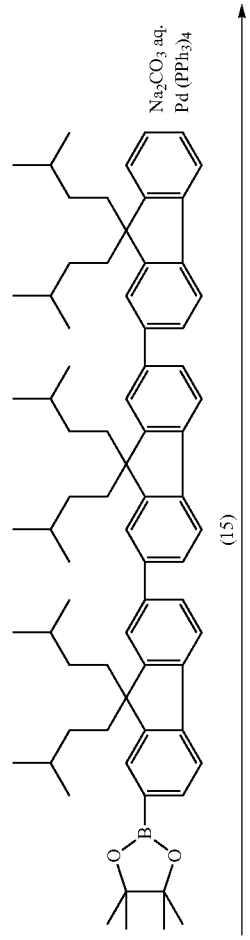
(15)
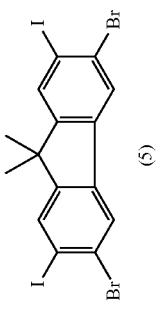
(5)
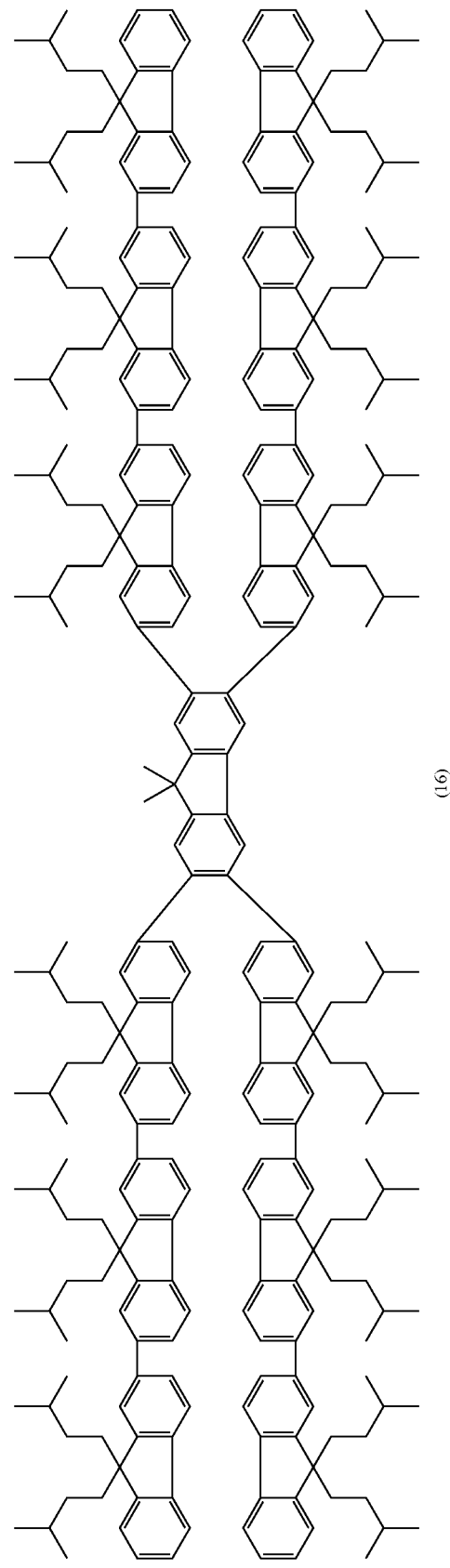
(16)

0.57 g (yield 18%) of an exemplified compound No. 24 that was a compound (16) was obtained as a white solid by the same reaction method as that of Example 3, except that a pinacolborane compound that was a compound (15) was used in place of the compound (11).

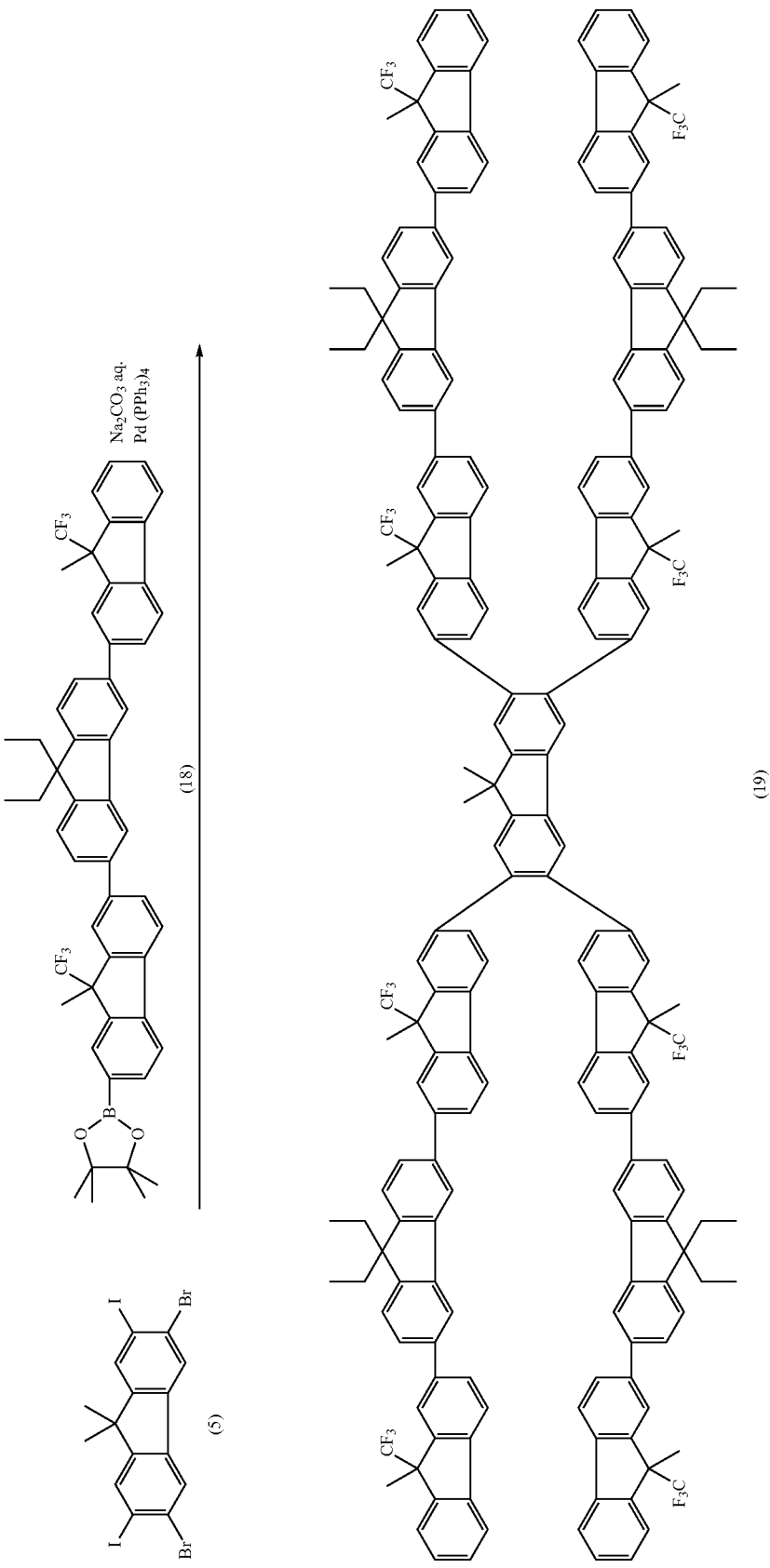
EXAMPLE 6
Synthesis of an exemplified compound No. 26

0.48 g (yield 19%) of an exemplified compound No. 26 that was a compound (19) was obtained as a white solid by the same reaction method as that of Example 3, except that a pinacolborane compound that was a compound (18) was used in place of the compound (11).

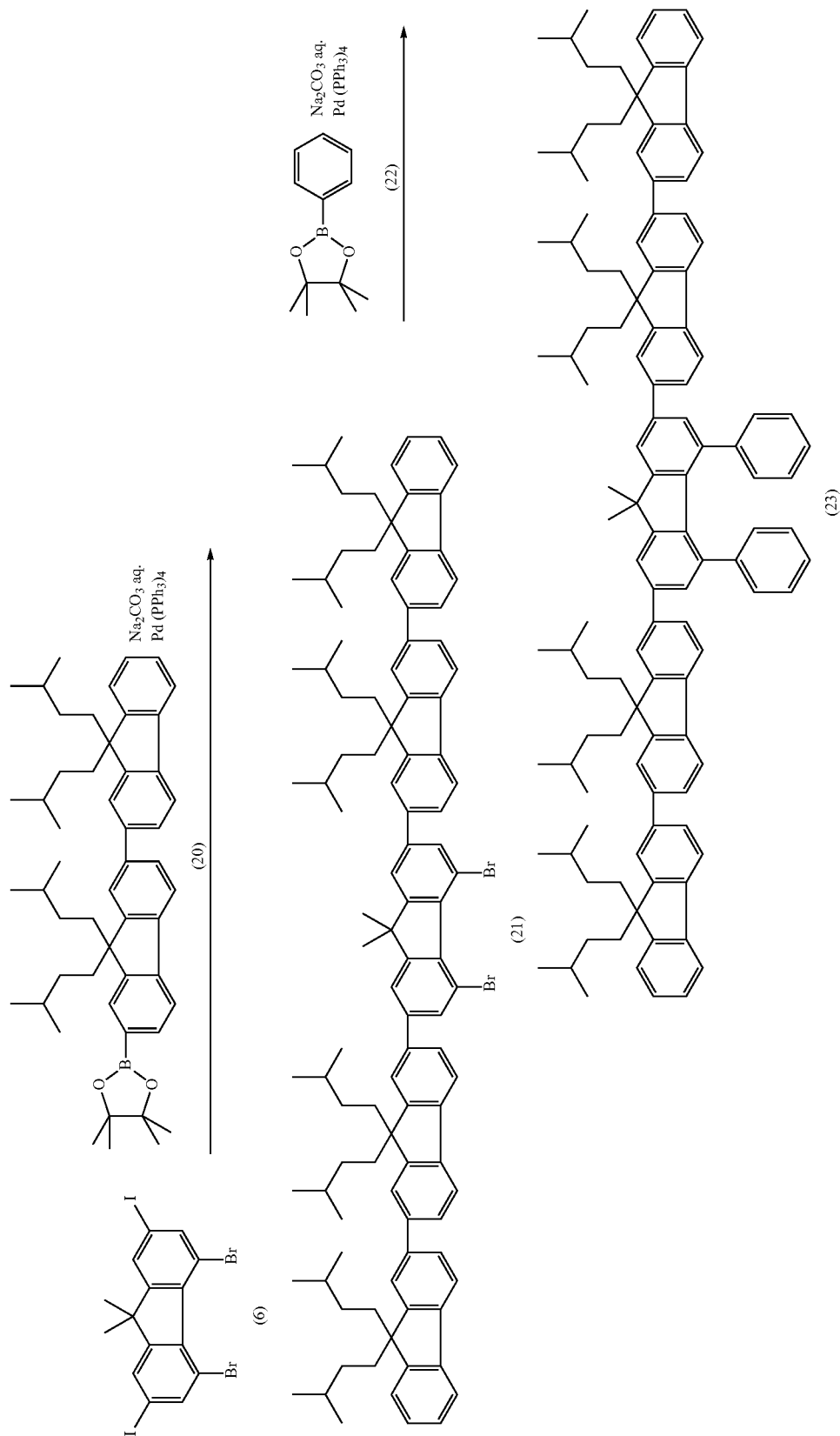

(1) The following reagents and solvents were placed in a 200 ml three-necked flask.

2,7-diiodo-4,5-dibromofluorene (precursor 11): 0.5 g (0.59 mmol)

Pinacolborane compound (compound (20)): 1.3 g (1.8 mmol)

Toluene: 80 ml

Ethanol: 20 ml

Next, the inside of the flask was set to be a nitrogen atmosphere, and 20 ml of a saturated sodium carbonate solution was dropped and then, 0.19 g (0.17 mmol) of tetrakis(triphenylphosphine)palladium(0) was added to the reaction solution, while the reaction solution was stirred at room temperature. Next, the reaction solution was stirred for 30 minutes at room temperature, and stirred for 18 hours while being refluxed. After the completion of the reaction, an organic layer was extracted with chloroform, and a solvent was evaporated under reduced pressure. Next, the obtained crude product was purified by silica gel column chromatography (developing solvent: a mixed solvent of hexane and chloroform), whereby 1.1 g (yield 94%) of an intermediate (21) was obtained as a white solid.

(2) To a 200 ml three-necked flask, 0.5 g (0.35 mmol) of an intermediate (21), 0.16 g (0.78 mmol) of a pinacolborane compound (compound (22)), 40 ml of toluene, and 10 ml of ethanol were placed. The inside of the flask was set to be a nitrogen atmosphere, and thereafter, 12 ml of a saturated sodium carbonate solution was dropped while the reaction solution was stirred at room temperature. Then, 0.08 g (0.07 mmol) of tetrakis(triphenylphosphine)palladium(0) was added. Then, the reaction solution was stirred at room temperature for 30 minutes, and thereafter, the reaction solution was stirred for 24 hours while being refluxed. After the completion of the reaction, an organic layer was extracted with chloroform, and a solvent was evaporated under reduced pressures. Next, the obtained crude product was purified by silica gel column chromatography (developing solvent: a mixed solvent of hexane and chloroform), whereby 0.22 g (yield 40%) of an exemplified compound No. 79 that was a compound (23) was obtained as a white solid.

EXAMPLE 8

Production of Organic Light Emitting Device

An organic light emitting device having the structure illustrated in FIG. 1B was produced.

First, as a transparent substrate 14, a film of indium tin oxide (ITO) having a film thickness of 120 nm was formed on a glass substrate (transparent substrate 15) by a sputtering method. Next, the substrate was subjected to ultrasonic cleaning with acetone and isopropyl alcohol (IPA) subsequently. Then, the resultant was washed in boiling IPA, followed by drying. Further, the resultant was subjected to UV/ozone cleaning. The thus-treated substrate was used as a transparent conductive supporting substrate.

A polymer shown below was formed into a film having a film thickness of 50 nm on the above transparent conductive support substrate by spin coating, whereby a hole injecting/transporting layer 13 was formed.

Poly(3,4-ethylenedioxythiophene)/poly(styrenesulfonate) (PEDOT/PSS, Baytron® P Al-4083, manufactured by Starck Ltd.)

Next, as the interlayer layer 16, a chloroform solution of polyvinyl carbazole (PVK, manufactured by Aldrich) was formed into a film on PEPOT/PSS by spin coating. The spin coating was conducted in a nitrogen atmosphere at a rotation number of 2000 rpm and a rotation time of 2 minutes. Further, the formed film was dried at 200° C. Here, the thickness of the interlayer layer 16 was set to be 200 Å.

Next, the exemplified compound No. 6 that was a host and an Ir complex (compound (24), hereinafter, referred to as Ir(mppy)$_3$) that was a guest having an emission peak at 509 nm shown below were placed in toluene, whereby 1% by weight of a toluene solution was prepared. At this time, the toluene solution was prepared so that the weight concentration ratio between Ir(mppy)$_3$ and the exemplified compound No. 6 was 2:98. A thin film having a thickness of 60 nm was formed by spin coating, using the toluene solution, whereby a light emitting layer 12 was formed. Note that Ir(mppy)$_3$ is a compound synthesized according to a synthesis method disclosed by Advanced Materials, 13, 1245 (2001).

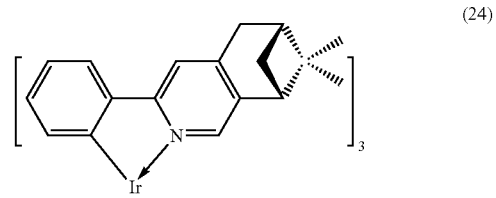

(24)

Next, as the electron injecting/transporting layer 11, calcium was vapor-deposited on the above light emitting layer 12 by vacuum vapor deposition to form a thin film. The thickness of the calcium film was set to be 1 nm, the vacuum degree during the vapor deposition was set to be $1.0 \times 10^{-4}$ Pa, and the film formation rate was set to be 0.1 nm/sec.

Next, as the metal electrode 10, an aluminum layer having a thickness of 150 nm was formed by vacuum vapor deposition. The vacuum degree during vapor deposition was set to be $1.0 \times 10^{-4}$ Pa, and the film formation rate was set to be 1.0 nm/sec or more to 1.2 nm/sec or less.

Finally, the metal electrode 10 was covered with a glass plate for protection in a nitrogen atmosphere, and sealed with an acrylic resin based adhesive. Thus, an organic light emitting device was obtained.

When a DC voltage of 8 V was applied to the device thus obtained, with an ITO electrode (transparent electrode 14) being an anode and an Al electrode (metal electrode 10) being a cathode, a current flows through the device at a current density of 30 mA/cm$^2$, and a green light emission of a luminance of 8600 cd/m$^2$ was observed. Further, in the device, a current efficiency was 38 cd/A, a peak of a light emission spectrum was 509 nm, and CIE chromaticity coordinates were x=0.27 and y=0.63.

Further, a luminance durability test was conducted. According to the luminance durability test, a time (luminance half-life period) required for a previously set initial luminance to become a half of the initial luminance is measured. In the present example, the initial luminance was set to be 1000 cd/m$^2$. As a result of the luminance durability test, it was found that the luminance half-life period (a time required for the luminance to become 500 cd/m$^2$ in the present example) was 101 hours.

EXAMPLE 9

A device was produced in the same way as in Example 8 except that the exemplified compound No. 17 was used in place of the exemplified compound No. 6 as the host of the light emitting layer 12. The obtained device was evaluated in the same way as in Example 8. Table 1 shows the results.

COMPARATIVE EXAMPLE 1

A device was produced in the same way as in Example 8 except that a comparative compound No. 1 represented by the following formula was used in place of the exemplified compound No. 6 as the host of the light emitting layer 12. The obtained device was evaluated in the same way as in Example 8. Table 1 shows the results. Note that a comparative compound No. 1 refers to poly(9,9-dioctyl)fluorene (manufactured by American Dye Source Inc.) and has a molecular weight Mw of 80000.

Comparative Compound No. 1

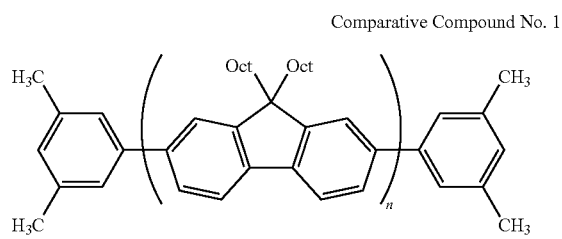

COMPARATIVE EXAMPLE 2

A device was produced in the same way as in Example 8 except that as the host of the light emitting layer 12 a comparative compound No. 2 represented by the following formula was used in place of the exemplified compound No. 6. The obtained device was evaluated in the same way as in Example 8. Table 1 shows the results. Note that a comparative compound No. 2 refers to oligofluorene.

Comparative Compound No. 2

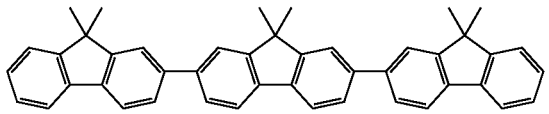

As shown in Table 1 described later, the following was found: when the fluorene compound of the present invention as a host is used together with a green Ir complex as a guest, the light emitting efficiency and durability of an obtained device are satisfactory. On the other hand, the following was also found: when the polyfluorene compound and oligofluorene compound shown in Comparative Examples 1 and 2 as hosts are used together with a green Ir complex as a guest, the light emitting efficiency and durability are degraded.

EXAMPLE 10

A device was produced in the same way as in Example 8, except for forming the light emitting layer 12 only of an exemplified compound No. 24. The obtained device was evaluated in the same way as in Example 8. Table 1 shows the results. Note that in a luminance durability test, an initial luminance was set to be 200 cd/m$^2$ in the present example.

EXAMPLE 11

A device was produced in the same way as in Example 8, except for forming the light emitting layer 12 only of an exemplified compound No. 26. The obtained device was evaluated in the same way as in Example 8. Table 1 shows the results. Note that in a luminance durability test, an initial luminance was set to be 200 cd/m$^2$ in the present example.

EXAMPLE 12

A device was produced in the same way as in Example 8, except for forming the light emitting layer 12 only of an exemplified compound No. 79. The obtained device was evaluated in the same way as in Example 8. Table 1 shows the results. Note that in a luminance durability test, an initial luminance was set to be 200 cd/m$^2$ in the present example.

EXAMPLE 13

An organic light emitting device having the structure illustrated in FIG. 1B was produced.

First, the compound (25) represented below was formed into a film having a thickness of 30 nm on a transparent conductive support substrate subjected to the same treatment as that in Example 8 by vapor deposition, whereby a hole injecting/transporting layer 13 was formed.

(25)

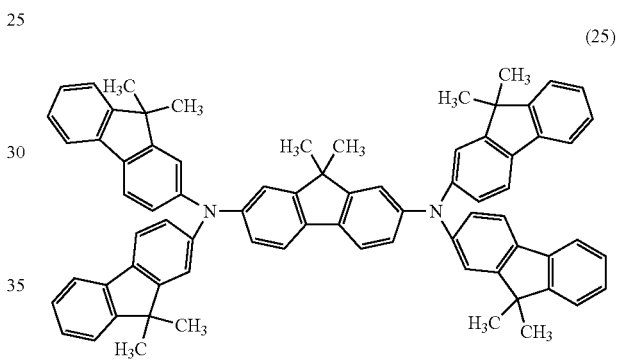

Next, the exemplified compound No. 6 as a host and an Ir complex as a guest (compound (26)), hereinafter, referred to as Ir(ppy)$_3$) represented below were co-deposited so that a vapor deposition rate ratio was 5 nm/sec: 0.1 nm/sec. At this time, the thickness of the light emitting layer 12 was set to be 50 nm, and the vacuum degree during vapor deposition was set to be 1.0×10$^{-4}$ Pa.

(26)

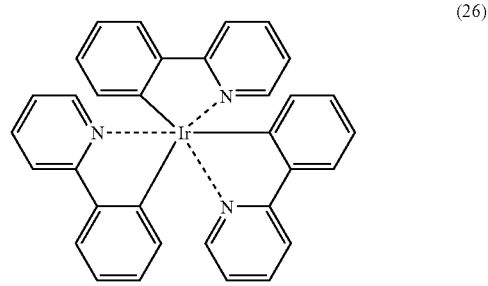

Next, as the electron injecting/transporting layer 11, BCP (a sublimed and purified product commercially available from Basocuproine, Aldrich) was vapor-deposited to form a thin film having a thickness of 25 nm.

Next, as the metal electrode 10, a vapor deposition material that was a mixture made of aluminum and lithium (the concentration of lithium is 1 atomic % based on the total amount)

was formed into a metal layer film having a thickness of 50 nm on the above electron injecting/transporting layer 11 by vacuum vapor deposition. Next, an aluminum layer having a thickness of 150 nm was formed by vacuum vapor deposition. The vacuum degree during vapor deposition was set to be $1.0 \times 10^{-4}$ Pa and a film formation rate of 1.0 nm/sec to 1.2 nm/sec.

Further, the device was sealed by the same method as that in Example 8. Thus, an organic light emitting device was obtained.

When a DC voltage of 6 V was applied to the device thus obtained, with an ITO electrode (transparent electrode 14) being an anode and an Al electrode (metal electrode 10) being a cathode, a current flows through the device at a current density of 30 mA/cm$^2$, and the green light emission of a luminance of 12000 cd/m$^2$ was observed. Further, in the device, a current efficiency was 42 cd/A, a peak of a light emission spectrum was 515 nm, and CIE chromaticity coordinates were x=0.32 and y=0.63. Further, a luminance durability test was conducted in the same way as in Example 8. The initial luminance in the present example was 1000 cd/m$^2$. As a result of the test, a luminance half-life period (a time required for a luminance to reach 500 cd/m$^2$ in the present example) was 112 hours.

EXAMPLE 14

A device was produced by the same method as that of Example 13, except for using an exemplified compound No. 17 in place of the exemplified compound No. 6 as a host of a light emitting layer. Regarding the device thus obtained, initial characteristics were evaluated and a luminance durability test was conducted by the same method as that in Example 13. Table 1 shows the results. Note that the initial luminance for conducting a luminance durability test was set to be 1000 cd/m$^2$.

EXAMPLE 15

A device having a configuration illustrated in FIG. 1A was produced.

First, a polymer shown below was formed into a film on a transparent conductive support substrate subjected to the same treatment as that in Example 8 by spin coating, whereby a hole injecting/transporting layer 13 was formed. Here, the thickness of the hole injecting/transporting layer 13 was set to be 50 nm. Poly(3,4-ethylenedioxythiophene)/poly(styrenesulfonate) (PEDOT/PSS, Baytron® P Al-4083, manufactured by Starck Ltd.)

Next, an exemplified compound No. 6 as a host and an Ir complex (compound (27), hereinafter, referred to as Ir(C8-piq)$_3$) having an emission peak at 618 nm as a guest represented below were placed in toluene, whereby 1% by weight of a toluene solution was prepared. At this time, the toluene solution was prepared so that the weight concentration ratio between the host and the guest was 98:2. A light emitting layer 12 having a thickness of 60 nm was formed by spin coating, using the toluene solution.

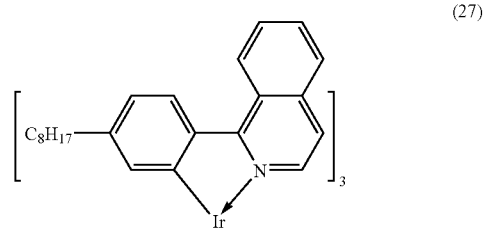

(27)

Next, as the electron injecting/transporting layer 11, calcium was vapor-deposited on the above light emitting layer 12 by vacuum vapor deposition to form a thin film. The thickness of the calcium film was set to be 1 nm, the vacuum degree during the vapor deposition was set to be $1.0 \times 10^{-4}$ Pa, and the film formation rate was set to be 0.1 nm/sec.

Next, as the metal electrode 10, an aluminum layer having a thickness of 150 nm was formed by vacuum vapor deposition. Here, the vacuum degree during vapor deposition was set to be $1.0 \times 10^{-4}$ Pa, and the film formation rate was set to 1.0 nm/sec or more to 1.2 nm/sec or less.

Finally, the metal electrode 10 was sealed in the same way as in Example 1. Thus, an organic light emitting device was obtained.

When a DC voltage of 5.5 V was applied to the device thus obtained, with an ITO electrode (transparent electrode 14) being an anode and an Al electrode (metal electrode 10) being a cathode, a current flows through the device at a current density of 30 mA/cm$^2$, and the red light emission of a luminance of 1500 cd/m$^2$ was observed. Further, in the device, a current efficiency was 8 cd/A, a peak of a light emission spectrum was 618 nm, and CIE chromaticity coordinates were x=0.67 and y=0.32.

Further, a luminance durability test was conducted in the same way as in Example 8. The initial luminance in the present example was 500 cd/m$^2$. As a result of the test, a luminance half-life period (a time required for a luminance to reach a half of the initial luminance, 250 cd/m$^2$ in the present example) was 325 hours.

EXAMPLE 16 to EXAMPLE 19

A device was produced in the same way as in Example 15, except for using exemplified compounds No. 17, No. 24, No. 26, and No. 79 in place of the exemplified compound No. 6 as a host of the light emitting layer 12. Regarding the obtained device, initial characteristics were evaluated in the same way as in Example 15. Further, regarding the obtained device, a luminance durability test was conducted. Note that the initial luminance for the luminance durability test was set to be 500 cd/m$^2$. Table 1 shows the results.

EXAMPLE 20

A device was produced in the same way as in Example 15, except for using a mixture of the exemplified compound No. 6 and the compound (25) (weight concentration ratio: compound No. 6/compound (25)=4/1) in place of the exemplified compound No. 6 as a host of the light emitting layer 12. Further, regarding the obtained device, initial characteristics were evaluated in the same way as in Example 15. Further, regarding the obtained device, a luminance durability test was conducted. Note that the initial luminance for the luminance durability test was set to be 500 cd/m². Table 1 shows the results.

EXAMPLE 21

A device was produced in the same way as in Example 15, except for using a mixture of the exemplified compound No. 17 and the compound (25) (weight concentration ratio: compound No. 17/compound (25)=4/1) in place of the exemplified compound No. 6 as a host of the light emitting layer 12. Further, regarding the obtained device, initial characteristics were evaluated in the same way as in Example 15. Further, regarding the obtained device, a luminance durability test was conducted. The initial luminance for the luminance durability test was set to 500 cd/m². Table 1 shows the results.

EXAMPLE 22

A device was produced in the same way as in Example 15, except for using a mixture of the exemplified compound 6 and polyvinyl carbazole (PVK, manufactured by Aldrich) (weight concentration ratio: compound No. 6/PVK=4/1) in place of the exemplified compound No. 6 as a host of the light emitting layer 12. Further, regarding the obtained device, initial characteristics were evaluated in the same way as in Example 15. Further, regarding the obtained device, a luminance durability test was conducted. Note that the initial luminance for the luminance durability test was set to be 500 cd/m². Table 1 shows the results.

EXAMPLE 23

A device was produced in the same way as in Example 15, except for using a mixture of the exemplified compound 17 and PVK (weight concentration ratio: compound No. 17/PVK=4/1) in place of the exemplified compound No. 6 as a host of the light emitting layer 12. Further, regarding the obtained device, initial characteristics were evaluated in the same way as in Example 15. Further, regarding the obtained device, a luminance durability test was conducted. Note that the initial luminance for the luminance durability test was set to be 500 cd/m². Table 1 shows the results.

EXAMPLE 24

A device having a configuration illustrated in FIG. 1C was produced.

A transparent conductive support substrate subjected to the same treatment as that in Example 8 was prepared, and thereafter, compounds (i) to (iv) shown below were placed in toluene, whereby 1% by weight of a toluene solution was prepared.

(i) Compound (27) (IR(C8-piq)₃) used in Example 15
(ii) Exemplified compound No. 6
(iii) Compound (28) that is a hole transporting compound represented by the following formula
(iv) Compound (29) that is an electron transporting compound represented by the following formula

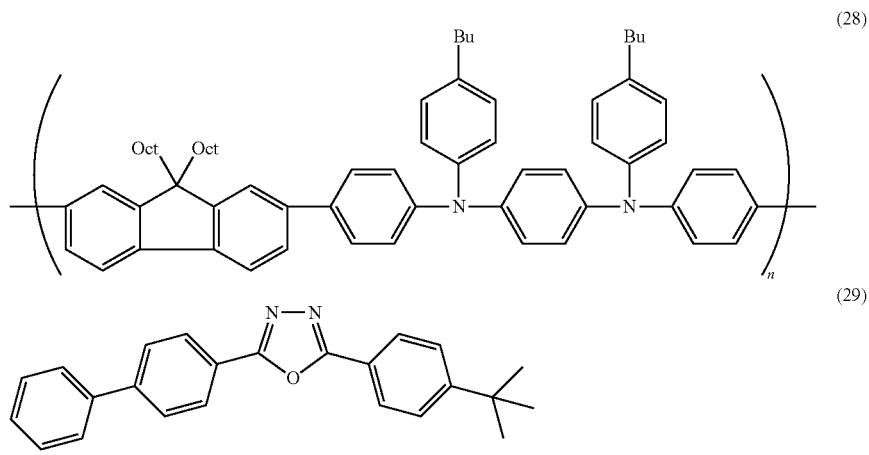

Note that the compound (28) was obtained by purifying a commercially available product (Mw=100000, manufactured by John Wiley & Sons, Inc.). Further, the compound (29) was obtained by subliming and purifying a commercially available product (manufactured by Aldrich). Here, the weight concentration ratio among (ii), (iii), and (iv) was 2:5:3, and the weight concentration ratio between (i) and total of (ii) to (iv) was 2:98.

A thin film corresponding to the light emitting layer 12 was formed on the above transparent conductive support substrate by spin coating, using the toluene solution. In this case, the thickness of the light emitting layer 12 was 60 nm.

Next, as the metal electrode 10, using a vapor deposition material that was a mixture made of aluminum and lithium (the concentration of lithium is 1 atomic %) a metal layer film having a thickness of 50 nm was formed on the above light emitting layer 12 by vacuum vapor deposition. Further, an aluminum layer having a thickness of 150 nm was formed by vacuum vapor deposition. In this case, the vacuum degree during vapor deposition was set to $1.0 \times 10^{-4}$ Pa and a film formation rate of 1.0 nm/sec to 1.2 nm/sec.

Further, the device was sealed in the same way as in Example 8. Thus, an organic light emitting device was obtained.

When a DC voltage of 6 V was applied to the device thus obtained, with an ITO electrode (transparent electrode 14) being an anode and an Al electrode (metal electrode 10) being a cathode, a current flows through the device at a current density of 30 mA/cm², and the red light emission of a luminance of 10000 cd/m² was observed. Further, in the device, a current efficiency was 4.5 cd/A, a peak of a light emission spectrum was 623 nm, and CIE chromaticity coordinates were x=0.68 and y=0.32.

Further, a luminance durability test was conducted in the same way as in Example 8. The initial luminance in the present example was 500 cd/m². As a result of the test, a luminance half-life period (a time required for a luminance to reach a half of the initial luminance, 250 cd/m² in the present example) was 10 hours.

EXAMPLE 25

A device was produced in the same way as in Example 24, except for using the exemplified compound No. 17 in place of the exemplified compound No. 6 as the above (ii). Regarding the obtained device, initial characteristics were evaluated in the same way as in Example 24. Further, regarding the obtained device, a luminance durability test was conducted. The initial luminance for the luminance durability test was set to be 500 cd/m². Table 1 shows the results.

TABLE 1

|  | EXEMPLIFIED COMPOUND No. | CURRENT EFFICIENCY (cd/A) | PEAK (nm) | CIE CHROMATICITY COORDINATES (x, y) | LUMINANCE HALF-LIFE (h) |
|---|---|---|---|---|---|
| EXAMPLE 8 (WET DEVICE) | 6 | 38 | 509 (GREEN) | (0.27, 0.63) | 101 |
| EXAMPLE 9 (WET DEVICE) | 17 | 42 | 510 (GREEN) | (0.27, 0.63) | 97 |
| COMPARATIVE EXAMPLE 1 (WET DEVICE) | COMPARATIVE COMPOUND 1 | 5 | 510 (GREEN) | (0.29, 0.64) | 8 |
| COMPARATIVE EXAMPLE 2*1 (WET DEVICE) | COMPARATIVE COMPOUND 2 | 1 | 513 (GREEN) | (0.32, 0.63) | <3*2 |
| EXAMPLE 10 (WET DEVICE) | 24 | 5.5 | 450 (BLUE) | (0.17, 0.22) | 85 |
| EXAMPLE 11 (WET DEVICE) | 26 | 5.8 | 449 (BLUE) | (0.17, 0.21) | 75 |
| EXAMPLE 12 (WET DEVICE) | 79 | 5.3 | 448 (BLUE) | (0.16, 0.20) | 68 |
| EXAMPLE 13 (WET DEVICE) | 6 | 42 | 515 (GREEN) | (0.32, 0.63) | 112 |
| EXAMPLE 14 (WET DEVICE) | 17 | 35 | 516 (GREEN) | (0.32, 0.63) | 126 |
| EXAMPLE 15 (WET DEVICE) | 6 | 8 | 618 (RED) | (0.67, 0.32) | 325 |
| EXAMPLE 16 (WET DEVICE) | 17 | 7.5 | 618 (RED) | (0.67, 0.32) | 310 |
| EXAMPLE 17 (WET DEVICE) | 24 | 8 | 617 (RED) | (0.67, 0.32) | 280 |
| EXAMPLE 18 (WET DEVICE) | 26 | 8.5 | 618 (RED) | (0.67, 0.32) | 250 |
| EXAMPLE 19 (WET DEVICE) | 79 | 7 | 619 (RED) | (0.67, 0.32) | 312 |
| EXAMPLE 20 (WET DEVICE) | 6 | 12 | 618 (RED) | (0.67, 0.32) | 524 |
| EXAMPLE 21 (WET DEVICE) | 17 | 13 | 619 (RED) | (0.67, 0.33) | 605 |
| EXAMPLE 22 (WET DEVICE) | 6 | 9.5 | 618 (RED) | (0.67, 0.32) | 68 |
| EXAMPLE 23 (WET DEVICE) | 17 | 10 | 619 (RED) | (0.67, 0.33) | 72 |
| EXAMPLE 24 (WET DEVICE) | 6 | 4.5 | 623 (RED) | (0.68, 0.32) | 10 |
| EXAMPLE 25 (WET DEVICE) | 7 | 4.3 | 620 (RED) | (0.68, 0.32) | 15 |

*1When a light emitting layer was formed, whitening of a film was recognized visually.
*2Measurement starting luminance was set to be 500 cd/m². Light was extinguished (device was short-circuited) at a luminance of 790 cd/m².

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-140160, filed May 28, 2007, which is hereby incorporated by reference in its entirety.

The invention claimed is:
1. An oligofluorene compound represented by the following general formula (III):

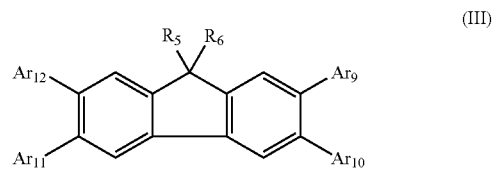

wherein $R_5$ and $R_6$ each represent an alkyl group, a fluorinated alkyl group, or a substituted or unsubstituted aryl group; $Ar_9$ to $Ar_{12}$ each represent a substituted or unsubstituted fluorenyl group or a substituted or unsubstituted oligofluorenyl group represented by the following general formula (V):

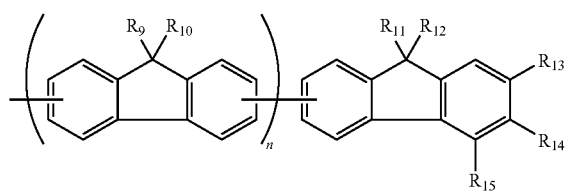

(V)

wherein $R_9$ to $R_{12}$ each represent an alkyl group, a fluorinated alkyl group, or a substituted or unsubstituted aryl group; $R_{13}$ to $R_{15}$ each represent a hydrogen atom, an alkyl group, a substituted or unsubstituted alkyl group, or a substituted or unsubstituted arylamino group; and n represents an integer of 0 to 10.

2. An organic light emitting device comprising: an anode, a cathode and a layer formed of an organic compound interposed between the anode and the cathode,
wherein a layer formed of the organic compound contains at least one kind of the fluorene compound according to claim 1.

3. The organic light emitting device according to claim 2, wherein the fluorene compound is contained in a light emitting layer.

4. An ink composition comprising at least one kind of the fluorene compound according to claim 1.

5. A display apparatus using the organic light emitting device according to claim 2.

\* \* \* \* \*